(12) United States Patent  (10) Patent No.: US 7,671,058 B2
Tokuyama et al.  (45) Date of Patent: Mar. 2, 2010

(54) N-(3,4-DISUBSTITUTED PHENYL) SALICYLAMIDE DERIVATIVES

(75) Inventors: Ryukou Tokuyama, Tokyo (JP); Toshifumi Wakamatsu, Tokyo (JP); Tatsurou Ichige, Tokyo (JP); Susumu Muto, Tokyo (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 67 days.

(21) Appl. No.: 11/765,011

(22) Filed: Jun. 19, 2007

(65) Prior Publication Data

US 2008/0227784 A1  Sep. 18, 2008

Related U.S. Application Data

(60) Provisional application No. 60/815,574, filed on Jun. 22, 2006.

(30) Foreign Application Priority Data

Jun. 21, 2006  (JP) .............................. 2006-171221

(51) Int. Cl.
A01N 43/42 (2006.01)
A61K 31/44 (2006.01)
C07D 241/04 (2006.01)
C07D 295/00 (2006.01)

(52) U.S. Cl. ........................... 514/255.01; 514/255.03; 544/382; 544/383; 544/393

(58) Field of Classification Search ............ 514/255.01, 514/255.03; 544/382, 383, 393
See application file for complete search history.

(56) References Cited

U.S. PATENT DOCUMENTS

| 3,041,236 | A | 6/1962 | Stecker |
| 3,331,874 | A | 7/1967 | Stecker |
| 3,332,996 | A | 7/1967 | Zerweck et al. |
| 3,382,145 | A | 5/1968 | Chupp et al. |
| 3,823,236 | A | 7/1974 | Buchel et al. |
| 3,906,023 | A | 9/1975 | Buchel et al. |
| 4,358,443 | A | 11/1982 | Coburn et al. |
| 4,560,549 | A | 12/1985 | Ritchey |
| 4,725,590 | A | 2/1988 | Ritchey |
| 4,742,083 | A | 5/1988 | Ritchey |
| 5,905,090 | A | 5/1999 | Bertolini et al. |
| 5,958,911 | A | 9/1999 | Evans et al. |
| 6,117,859 | A | 9/2000 | Evans et al. |
| 6,174,887 | B1 | 1/2001 | Haruta et al. |
| 6,465,455 | B1 | 10/2002 | Brown et al. |
| 6,492,425 | B1 | 12/2002 | Callahan et al. |
| 2003/0083386 | A1 | 5/2003 | Yuan et al. |
| 2004/0259877 | A1 | 12/2004 | Muto et al. |
| 2005/0227959 | A1 | 10/2005 | Yoshida et al. |
| 2006/0014811 | A1 | 1/2006 | Muto et al. |
| 2006/0019958 | A1 | 1/2006 | Muto et al. |
| 2006/0035944 | A1 | 2/2006 | Muto et al. |
| 2006/0089395 | A1 | 4/2006 | Muto et al. |
| 2006/0094718 | A1 | 5/2006 | Muto et al. |
| 2006/0100257 | A1 | 5/2006 | Muto et al. |

(Continued)

FOREIGN PATENT DOCUMENTS

| EP | 0 081 782 | 6/1983 |
| EP | 0 221 211 | 5/1987 |
| EP | 0 221 346 | 5/1987 |
| EP | 0 931 544 | 7/1999 |
| EP | 1 008 346 | 6/2000 |

(Continued)

OTHER PUBLICATIONS

Thawani, et al., STAT6-mediated suppression of erythropoiesis in an experimental model of malarial anemia, Haematologica, 94(2) 195-204 (2008).*

(Continued)

Primary Examiner—James O Wilson
Assistant Examiner—Erich A Leeser
(74) Attorney, Agent, or Firm—Greenblum & Bernstein, P.L.C.

(57) ABSTRACT

A compound represented by the following formula (I) or a salt thereof:

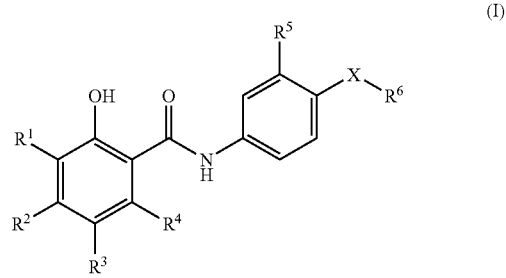

wherein $R^1$, $R^2$, $R^3$ and $R^4$ represent hydrogen atom, a halogen atom, cyano group, nitro group, a $C_{1-4}$ alkyl group, a halogenated $C_{1-4}$ alkyl group or a $C_{1-4}$ alkoxy group, $R^5$ represents a halogen atom, cyano group, a $C_{1-4}$ alkyl group, a halogenated $C_{1-4}$ alkyl group or a $C_{1-4}$ alkoxy group, $R^6$ represents a $C_{5-7}$ cycloalkyl group, a substituted $C_{5-7}$ cycloalkyl group, a 5 to 7-membered completely saturated heterocyclic group or a substituted 5 to 7-membered completely saturated heterocyclic group, X represents a single bond, oxygen atom, sulfur atom, $NR^7$, —O—$CH_2$— or —N($R^8$)—$CH_2$—, $R^7$ represents hydrogen atom or a $C_{1-4}$ alkyl group, or $R^7$ may combine with a substituent of $R^6$ to represent a single bond, methylene group or ethylene group, $R^8$ represents hydrogen atom, a $C_{1-4}$ alkyl group or a $C_{7-12}$ aralkyl group, which is useful as an active ingredient of a medicament for prophylactic and/or therapeutic treatment of diseases caused by an activation of STAT6 and/or NF-κB.

5 Claims, No Drawings

U.S. PATENT DOCUMENTS

| | | |
|---|---|---|
| 2006/0111409 A1 | 5/2006 | Muto et al. |
| 2006/0122243 A1 | 6/2006 | Muto et al. |
| 2007/0042997 A1 | 2/2007 | Itai et al. |
| 2007/0185059 A1 | 8/2007 | Muto et al. |
| 2007/0185110 A1 | 8/2007 | Muto et al. |
| 2007/0254956 A1 | 11/2007 | Shudo et al. |

FOREIGN PATENT DOCUMENTS

| | | |
|---|---|---|
| EP | 1 018 514 | 7/2000 |
| EP | 1 130 016 | 5/2001 |
| EP | 1 113 000 | 7/2001 |
| EP | 1 314 712 | 5/2003 |
| EP | 1 344 525 | 9/2003 |
| EP | 1 346 987 | 9/2003 |
| EP | 1 352 650 | 10/2003 |
| EP | 1 382 603 | 1/2004 |
| EP | 1 510 207 | 3/2005 |
| EP | 1 518 855 | 3/2005 |
| EP | 1 535 609 | 6/2005 |
| GB | 996 074 | 6/1965 |
| JP | 37-000225 | 1/1962 |
| JP | 57-112360 | 7/1982 |
| JP | 62-99329 | 5/1987 |
| JP | 9-227561 | 9/1997 |
| JP | 10-45738 | 2/1998 |
| JP | 10-87491 | 4/1998 |
| JP | 10-175964 | 6/1998 |
| JP | 10-175965 | 6/1998 |
| JP | 11-21225 | 1/1999 |
| JP | 11-029475 | 2/1999 |
| JP | 11-106340 | 4/1999 |
| JP | 11-116481 | 4/1999 |
| JP | 11-158164 | 6/1999 |
| JP | 2000-229959 | 8/2000 |
| JP | 2002-249473 | 9/2002 |
| WO | 94/01113 | 1/1994 |
| WO | 97/09315 | 3/1997 |
| WO | 98/32017 | 7/1998 |
| WO | 99/40907 | 8/1999 |
| WO | 99/46236 | 9/1999 |
| WO | 99/46244 | 9/1999 |
| WO | 99/46267 | 9/1999 |
| WO | 99/51580 | 10/1999 |
| WO | 99/55663 | 11/1999 |
| WO | 99/65449 | 12/1999 |
| WO | WO 99/65449 * | 12/1999 |
| WO | 00/01349 | 1/2000 |
| WO | 00/35442 | 6/2000 |
| WO | 02/14321 | 2/2002 |
| WO | 02/16633 | 2/2002 |
| WO | 02/38107 | 5/2002 |
| WO | 02/49632 | 6/2002 |
| WO | 02/067919 | 9/2002 |
| WO | 02/076918 | 10/2002 |
| WO | 02/076926 | 10/2002 |
| WO | 02/079165 | 10/2002 |
| WO | 03/103647 | 12/2003 |
| WO | 03/103648 | 12/2003 |
| WO | 03/103654 | 12/2003 |
| WO | 03/103655 | 12/2003 |
| WO | 03/103656 | 12/2003 |
| WO | 03/103657 | 12/2003 |
| WO | 2004/002964 | 1/2004 |
| WO | 2004/006906 | 1/2004 |
| WO | 2005/007151 | 1/2005 |

OTHER PUBLICATIONS

Kojocaru A.F. et al., "Action of New Class of Substituted Salicylanilides on Ion Conductivity of Lipid Membranes", Biofizika, vol. 26, No. 6, pp. 995-998, 1981.

Cojocaru A.F. et al., "Effect of a New Class of Substituted Salicylanilides on the Ionic Conductivity of Lipid Membranes", Cell Biophysics, vol. 26, No. 6, pp. 1017-1020, 1981.

Shen et al., "Interaction of Stat6 and NF-κB: Direct Association and Synergistic Activation of Interleukin-4-Induced Transcription", Molecular and Cellular Biology, vol. 18, No. 6, pp. 3395-3404, 1998.

English Language Abstract of JP 10-175964.

English Language Abstract of JP10-175965.

English Language Abstract of JP 11-029475.

English language abstract of JP 11-106340.

Darnell et al., "Jak-STAT Pathways and Transcriptional Activation in Response to IFNs and Other Extracellular Signaling Proteins", Science, vol. 264, No. 5164, pp. 1415-1421, 1994.

Lin et al., "The Role of Shared Receptor Motifs and Common Stat Proteins in the Generation of Cytokine Pleiotropy and Redundancy by IL-2, IL-4, IL-7, IL-13, and IL-15", Immunity, vol. 2, No. 4, pp. 331-339, 1995.

McKenzie, "Regulationof T helper type 2 cell immunity by interleukin-4 and interleukin-13", Pharmacology & Therapeutics, vol. 88, No. 2, pp. 143-151, 2000.

Takeda et al., "Impaired IL-13-Mediated Functions of Macrophages in STAT6-Deficient Mice", The Journal of Immunology, vol. 157, No. 8, pp. 3220-3222, 1996.

Tekkanat et al., "IL-13-Induced Airway Hyperreactivity during Respiratory Syncytial Virus Infection is STAT6 Dependent", The Journal of Immunology, vol. 166, No. 8, pp. 3542-3548, 2001.

Shimoda et al., "Lack of IL-4-induced Th2 response and IgE class switching in mice with disrupted Stat6 gene", Nature, vol. 380, No. 6575, pp. 630-633, 1996.

Hou et al., "An Interleukin-4-Induced Transcription Factor: IL-4 Stat", Science, vol. 265, No. 5179, pp. 1701-1706, 1994.

Miyata et al., "STAT6 deficiency in a mouse model of allergen-induced airways inflammation abolishes eosinophilia but induces infiltration of CD8+ T cells", Clinical and Experimental Allergy, vol. 29, No. 1, pp. 114-123, 1999.

Clark et al., "Genomic sequence for human prointerleukin 1 beta: possible evolution from a reverse transcribed prointerleukin 1 alpha gene", Nucleic Acids Research, vol. 14, No. 20, pp. 7897-7914, 1986.

Nedospasov et al. "Tandem Arrangement of Genes Coding for Tumor Necrosis Factor (TNF-α) and Lymphotoxin (TNF-β) in the Human Genome", Cold Springs Harbor Symposia on Quantitative Biology, vol. 51, Pt. 1, pp. 611-624, 1986.

Baldwin, "The NF-κB and IκB Proteins: New Discoveries and Insights", Annual Reviews in Immunology, vol. 14, pp. 649-681, 1996.

Verma et al., "Rel/NF-κB/IκB family: intimate tales of association and dissociation", Genes & Development, vol. 9, No. 22, pp. 2723-2735, 1995.

Baeuerle et al., "Function and Activation of NF-κB in the Immune System", Annual Reviews in Immunololgy, vol. 12, pp. 141-179, 1994.

Baeuerle et al., "NF-κB: Ten Years After", Cell, vol. 87, No. 1, pp. 13-20, 1996.

Kumar et al., "Nuclear factor-κB: its role in health and disease", J. Mol. Med., vol. 82, No. 7, pp. 434-448, 2004.

Baldwin, "The transcription factor NF-κB and human disease", The Journal of Clinical Investigation, vol. 107, No. 1, pp. 3-6, 2001.

Singh et al., "Synthesis of 5-Chloro-3'-nitro-4'-substituted Salicylanilides, a New Series of Anthelmintic and Antimicrobial Agents", Journal of Medicinal Chemistry, vol. 20, No. 6, pp. 826-829, 1977.

Singh et al., "5-chloro-3'-nitro-4'-cyclohexylaminosalicylanilide: A New Cestocidal Agent", Indian Journal of Experimental Biology, vol. 14, No. 3, pp. 332-333, 1976.

Tokuyama et al., "Structure-Activity Relationship (SAR) Studies on Oxazolidinone Antibacterial Agents. 2.[1])Relationship between Lipophilicity and Antibacterial Activity in 5-Thiocarbionyl Oxazolidinones", Chem. Pharm. Bull., vol. 49, No. 4, pp. 353-360, 2001.

Brickner et al., "Synthesis and Antibacterial Activity of U-100592 and U-100766. Two Oxazolidinone Antibacterial Agents for the Potential Treatment of Multidrug- Resistant Gram-Positive Bacterial Infection", Journal Medicinal Chemistry, vol. 39, No. 3, pp. 673-679, 1996.

Prugh et al., "A Simple Method of Protecting a Secondary Amine with tert Butyloxycarbonyl (BOC) in the Presence of a Primary Amine", Synthetic Communications, vol. 22, No. 16, pp. 2357-2360, 1992.

Yamamoto et al., "Synthesis and Biological Activity of Novel 1,3-Benzoxazine Derivatives as K+ Channel Openers", Chem. Pharm. Bull., vol. 44, No. 4, pp. 734-745, 1996.

Ehret et al., "DNA Binding Specificity of Different STAT Proteins", The Journal of Biological Chemistry, vol. 276, No. 9, pp. 6675-6688, 2001.

U.S. Appl. No. 11/835,978 to Susumu Muto et al., filed Aug. 8, 2007.
U.S. Appl. No. 11/835,997 to Susumu Muto et al., filed Aug. 8, 2007.
English language Abstract of JP 11-116481.
English language Abstract of JP 2000-229959.
U.S. Appl. No. 10/433,619, filed Dec. 18, 2001.
U.S. Appl. No. 10/515,341, filed Jun. 5, 2003.
U.S. Appl. No. 10/515,343, filed Jun. 5, 2003.
U.S. Appl. No. 10/515,342, filed Jun. 5, 2003.
U.S. Appl. No. 10/515,623, filed Jun. 5, 2003.
U.S. Appl. No. 11/783,324, filed Apr. 9, 2007.
U.S. Appl. No. 11/783,325, filed Apr. 9, 2007.
U.S. Appl. No. 10/515,622, filed Jun. 5, 2003.
U.S. Appl. No. 10/516,294, filed Jun. 5, 2003.
U.S. Appl. No. 10/516,292, filed Jun. 5, 2003.
U.S. Appl. No. 10/516,293, filed Jun. 5, 2003.
U.S. Appl. No. 10/564,407, filed Jul. 16, 2004.
U.S. Appl. No. 10/577,487, filed Oct. 28, 2004.

Yamamoto et al., "Role of the NF-κB Pathway in the Pathogenesis of Human Disease States" *Current Molecular Medicine* 1:287-296, 2001.

Chen et al., "New Insights in the Role of Nuclear Factor κB, a Ubiquitous Transcription Factor in the Initiation of Diseases" *Clinical Chemistry* 45(1):7-17, 1999.

MacNee et al., "Oxidants and Antioxidants as Therapeutic Targets in Chronic Obstructive Pulmonary Disease" *American Journal of Respiratory and Critical Care Medicine* 160:S58-S65, 1999.

Wang et al., "Lipopolysaccharide-induced *MCP*-1 Gene Expression in Rat Tubular Epithelial Cells is Nuclear Factor- κB Dependent" *Kidney International* 57:2011-2022, 2000.

Aupperle et al., "NF- κB Regulation by IκB Kinase is Primary Fibroblast-Like Synoviocytes" *The Journal of Immunology* 163:427-433, 1999.

Liu et al., "Extracellular Signal-Regulated Kinase 1/Extracellular Signal-Regulated Kinase 2 Mitogen-Activated Protein Kinase Signaling and Activation of Activator Protein 1 and Nuclear Factor κB Transcription Factors Play Central Roles in Interleukin-8 Expression Stimulated by Monosodium Urate Monohydrate and Calcium Pyrophosphate Crystals in Monocytic Cells" *Arthritis & Rheumatism* 43(5):1145-1155, 2000.

Baldwin et al., "Control of Oncogenesis and Cancer Therapy Resistance by the Transcription Factor NF-κB" *The Journal of Clinical Investigation* 107(3):241-246, 2001.

Suzuki et al., "Decoy Against Nuclear Factor-Kappa B Attenuates Myocardial Cell Infiltration and Arterial Neointimal Formation in Murine Cardiac Allografts" *Gene Therapy* 7:1847-1852, 2000.

Jobin et al., "The IκB/NF-κB System: A Key Determinant of Mucosal Inflammation and Protection" *Am. J. Physiol. Cell Physiol.* 278:C451-C462, 2000.

Piscopo et al., "Biological Activity of 4-Hydroxyisophthalic Acid Derivatives. III. Variously Substituted Anilides with Antimicrobial Activity" *Bollettino—Societa Italiana di Biologia Sperimentale* 61(2):199-204, 1985 (Abstract).

Marking et al., "Comparative Toxicity of 29 Nitrosalicylanilides and Related Compounds to Eight Species of Fish" *Invest. Fish Contr.* No. 36-38, 37, 11 pp., 1970 (Abstract).

Lang et al., "Cyclic Salicylanilides as Antibacterial Agents" *Journal of the Society of Cosmetic Chemists* 17:355-360, 1966 (Abstract).

Schraufstaetter et al., "A New Molluscicide. I. Relations Between Structure and Activity" *Zeitschrift fuer Naturforschung* 16b:95-108, 1961 (Abstract).

Didonato et al., "A Cytokine-Responsive IκB Kinase that Activates the Transcription Factor NF-κB" *Nature* 388:548-554, 1997.

Regnier et al., "Identification and Characterization of an IκB Kinase" *Cell* 90:373-383, 1997.

Woronicz et al., "IκB Kinase-β: NF-κB Activation and Complex Formation with IκB Kinase-α and NIK" *Science* 278:866-869, 1997.

Zandi et al., "The IκB Kinase Complex (IKK) Contains Two Kinase Subunits, IKKα and IKKβ, Necessary for IκB Phosphorylation and NF-κB Activation" *Cell* 91:243-252, 1997.

Kopp et al., "Inhibition of NF-κB by Sodium Salicylate and Aspirin" *Science* 265: 956-959, 1994.

Yin et al., "The Anti-Inflammatory Agents Aspirin and Salicylate Inhibit the Activity of IκB Kinase-β" *Nature* 396:77-80, 1998.

Scheinman et al., "Role of Transcriptional Activation of IκBα in Mediation of Immunosuppression by Glucocorticoids" *Science* 270:283-286, 1995.

Manna et al., "Immunosupressive Leflunomide Metabolite (A77 1726) Blocks TNF-Dependent Nuclear Factor-κB Activation and Gene Expression" *The Journal of Immunology* 162:2095-2102, 1999.

Sullivan et al., "2-Chloro-4(trifluoromethyl)pyrimidine-5-$N$-(3',5'-bis(trifluromethyl)phenyl)-carboxamide: A Potent Inhibitor of NF-κB and AP-1-Mediated Gene Expression Identified Using Solution-Phase Combinatorial Chemistry" *J. Med. Chem.* 41:413-419, 1998.

Matsumoto et al., "Synthesis of NF-κB Activation Inhibitors Derived from Epoxyquinomicin C" *Bioorganic & Medicinal Chemistry Letters* 10:865-869, 2000.

Okamoto, "NF-κB-Mediated Mechanism of Action of Antirheutmatic Drugs, Specifically DMARDS" 18th Meeting of Japanese Inflammatory Society, pp. 57, 2000, along with an English language translation thereof.

Macielag et al., "Substituted Salicylanilides as Inhibitors of Two-Component Regulatory Systems in Bacteria" *J. Med. Chem.* 41:2939-2945, 1998.

Zwaagstra et al., "Synthesis of Carboxylated Flavonoids as New Leads for $LTD_4$ Antagonists" *Eur. J. Med. Chem.* 31:861-874, 1996.

Zh. Org. Khim., vol. 16, pp. 2185-2188, 1980, along with a partial English translation.

South et al., Reactions of a 4-(Trifluoromethyl)thizaole Dianion *J. Heterocyclic Chem.* 28:1017-1024, 1991.

Tajika, "Studies on the Synthesis of the 2-Aminothiazole Derivatives. IV. Reactions of the 1,1'-Dithiodiformamidine Hydrohalide with the Ketones" *Yakugaku Zasshi*, vol. 81, pp. 1456-1459, 1961, accompanied by a partial English translation.

Nihon Kagaku Zasshi, vol. 83, pp. 209-211, 1962, along with a partial English language translation.

Yura et al., Studies on Acetylenic Compounds. XXII.[1)] Ring Closure. (4). New Synthesis of Thiazoles and Imidazole *Chem. Pharm. Bull.* 10:376-382, 1962.

Diez-Barra et al., "On the π-π Interaction of the Benzylation of Ketones" *Tetrahedron* 53(33):11437-11448, 1997.

Hill et al., "Functional Analysis of a Growth Factor-Responsive Transcription Factor Complex" *Cell* 73:395-406, 1993.

Madan et al., "2'-Hydroxychalcone Inhibits Nuclear Factor-κB and Blocks Tumor Necrosis Factor-α- and Lipopolysacchardie-Induced Adhesion of Neutrophils to Human Umbilical Vein Endothelial Cells" *Molecular Pharmacology* 58(3):526-534, 2000.

Berking et al., "Basic Fibroblast Growth Factor and Ultraviolet B Transform Melanocytes in Human Skin" *American Journal of Pathology* 158(3):943-953, 2001.

Singh et al., "IL-8 Expression in Malignant Melanoma: Implications in Growth and Metastasis" *Histology and Histopathology* 15:843-849, 2000.

Recio et al., "Ink4a/Arf Deficiency Promotes Ultraviolet Radiation-induced Melanomagenesis" *Cancer Research* 62(22):6724-6730, 2002.

Lehmann et al., "Inhibition of the Progression of Multiple Sclerosis by Linomide is Associated with Upregulation of CD4+/CD45RA+ Cells Downregulation of CD4+/CD45RO+ Cells" *Clinical Immunology and Immunopathology* 85(2):202-209, 1997 (Abstract).

Kakutani et al., "JTE-607, A Novel Inflammatory Cytokine Synthesis Inhibitor without Immunosupression, Protects from Endotoxin Shock in Mice" *Inflammation Research* 48(8):461-468, 1999 (Abstract).

Chung et al., "Primary Sensitization Potentials of Some Halogenated Salicylanides and their Cross-Sensitivity in Guinea-Pigs" *Food and Cosmetics Toxicology* 15(4):325-330, 1977 (Abstract).

Matsuzaki et al., "Increased Mast Cell Density in Peritoneal Endometriosis Compared with Eutopic Endometrium Endometriosis" *Amer. J. Reproductive Immunol.* 40:291-294, 1998.

Chegini, "Peritoneal Molecular Environment, Adhesion Formation and Clinical Implication" *Frontiers in Bioscience* 7:e91-115, 2002.

Uchiide et al., Nikkei Medical, No. 415, p. 28, 2002, with English translation.

Uchiide et al., "Pathological Evaluation of the Rat Endometriosis Model" *Fertility and Sterility* 78(4):782-786, 2002.

* cited by examiner

US 7,671,058 B2

N-(3,4-DISUBSTITUTED PHENYL) SALICYLAMIDE DERIVATIVES

CROSS-REFERENCE TO RELATED APPLICATIONS

This application claims the benefit of U.S. Provisional Application No. 60/815,574, filed Jun. 22, 2006, and also claims priority of Japanese Patent Application No. 2006-171221, filed on Jun. 21, 2006, the entire contents of which are expressly incorporated in their entireties.

FIELD OF INVENTION

The present invention relates to compounds having inhibitory activity against activation of STAT6 and/or NF-κB. More specifically, the present invention relates to compounds which are salicylanilide compounds wherein the benzene ring which binds to the nitrogen atom is 3,4-disubstituted, and wherein the substituent in the 4-position is a group including a $C_{5-7}$ cycloalkyl group, a substituted $C_{5-7}$ cycloalkyl group, a 5 to 7-membered completely saturated heterocyclic group or a substituted 5 to 7-membered completely saturated heterocyclic group, which compounds have inhibitory activity against activation of STAT6 and/or NF-κB and are useful for prophylactic and/or therapeutic treatment of diseases caused by an activation of STAT6 and/or NF-κB.

BACKGROUND ART

Due to the progress of gene analysis of cytokines and cell adhesion factors, it has been revealed that these substances are controlled by variety of transcription factors (also called as transcription regulatory factors)

STAT (Signal Transduction and Activator of Transcription) is an intracellular protein containing an SH2 (Src Homology 2) region and transmits signals from cytokine receptor into nucleus, and functions per se as an anscriptional factor. Among STAT proteins, STAT6 is known as an important transcriptional factor transmitting signals of interleukin-4 (IL-4) and interleukin-13 (IL-13). STAT6 is bound to GYKXF (SEQ ID NO: 3) motif of IL-4 receptor α chain (IL-4R α) which is a constituting factor of IL-4 receptor and IL-13 receptor, and a JAK family kinase is also bound to these receptors. When IL-4 or IL-13 is bound to a receptor, STAT6 is dimerized by undergoing tyrosine-phosphorylation by the JAK family kinase and translocated into the nucleus where it exerts a function as the transcription factor (refer to Non-patent Documents 1-7).

It is known that IL-4 and IL-13 are related to allergic diseases such as asthma (refer to Non-Patent Documents 3, 4, 5 and 8). Therefore, inhibition of activation of STAT6 is considered to be effective for prophylactic and/or therapeutic treatment of diseases caused by an activation of STAT6.

NF-κB (Nuclear Factor-κB) belongs to a family of closely related homodimeric or heterodimeric transcriptional factor complexes consisting of various combinations of the Rel/NF-κB family of polypeptides. In most cell types, NF-κB exists as a heterodimer (p50/RelA) comprising a 50 kDa and a 65 kDa subunit. The heterodimer is sequestered in the cytoplasm in association with inhibitor of NF-κB (IκB) family of proteins to be kept in an inactive state. Upon stimulation of cells with cytokines (for example, tumor necrosis factor-α (TNF-α) and interleukin-1 (IL-1)), CD40 ligand, lipopolysaccharide (LPS), oxidants, mitogens (for example, phorbol ester), viruses, ultraviolet, or the like, IκB proteins are phosphorylated at specific serine residues, poly-ubiquitinated, and then degraded through a proteasome-dependent pathway. Activated form of NF-κB separated from IκB immediately move into nucleus, and exhibits functions as a transcription factor by binding to promoter region which has recognition sequence of NF-κB. Examples of genes of which expressions are under the control with NF-κB include, for example, inflammatory cytokines (for example, IL-1, interleukin-6 (IL-6), interleukin-8 (IL-8) and TNF-α), cell adhesion molecules (for example, intracellular cell adhesion molecule-1 (ICAM-1), vascular cell adhesion molecule-1 (VCAM-1) and E-selectin) and inducible nitric oxide synthase (iNOS) (see, Non-Patent Documents 9-14).

It is known that NF-κB is related to various kinds of diseases (see, Non-Patent Documents 15 and 16). Therefore, inhibition of activation of NF-κB is considered to be effective for prophylactic and/or therapeutic treatment of diseases caused by an activation of NF-κB.

As for salicylanilide compounds wherein the benzene ring which binds to the nitrogen atom is 3,4-disubstituted, and wherein the substituent in the 4-position is a group including a $C_{5-7}$ cycloalkyl group, a substituted $C_{5-7}$ cycloalkyl group, a 5 to 7-membered completely saturated heterocyclic group or a substituted 5 to 7-membered completely saturated heterocyclic group, they compounds are described in Patent Document 1 and Non-Patent Documents 17 and 18. However, the compounds encompassed within the scope of the present invention are not described in these documents. Furthermore, these documents do not disclose any information of inhibitory activity against activation of STAT6 and/or NF-κB, and the intended uses of the compounds described in the aforementioned documents are completely different from those of the present invention.

As for compounds having inhibitory activity against activation of STAT6, such compounds are described in, for example, Patent Documents 2-14. However, the compounds described in these documents have completely different chemical structures from those of the compounds of the present invention.

As for compounds having inhibitory activity against activation of NF-κB, such compounds are described in, for example, Patent Documents 15-18. However, the specific compounds encompassed within the present invention are not described in those documents. Furthermore, these documents do not describe any information about the inhibitory activity against activation of STAT6.

[Patent Document 1] The pamphlet of International Publication No. WO94/01113

[Patent Document 2] Japanese Patent Unexamined Publication (KOKAI) No. 10-175964

[Patent Document 3] Japanese Patent Unexamined Publication (KOKAI) No. 10-175965

[Patent Document 4] Japanese Patent Unexamined Publication (KOKAI) No. 11-029475

[Patent Document 5] Japanese Patent Unexamined Publication (KOKAI) No. 11-106340

[Patent Document 6] Japanese Patent Unexamined Publication (KOKAI) No. 11-116481

[Patent Document 7] Japanese Patent Unexamined Publication (KOKAI) No. 2000-229959

[Patent Document 8] The pamphlet of International Publication No. WO02/14321

[Patent Document 9] The pamphlet of International Publication No. WO02/38107

[Patent Document 10] U.S. Patent Application Publication No. US 2005/0227959

[Patent Document 11] European Patent Publication No. EP 1346987

[Patent Document 12] European Patent Publication No. EP 1377553

[Patent Document 13] European Patent Publication No. EP 1382603

[Patent Document 14] European Patent Publication No. EP 1518855

[Patent Document 15] European Patent Publication No. EP 1085848

[Patent Document 16] European Patent Publication No. EP 1314712

[Patent Document 17] European Patent Publication No. EP 1352650

[Patent Document 18] European Patent Publication No. EP 1535609

[Non-Patent Document 1] Science, vol. 264, No. 5164, pp. 1415-1421 (1994).

[Non-Patent Document 2] Immunity, vol. 2, No. 4, pp. 331-339 (1995).

[Non-Patent Document 3] Pharmacol. Ther., vol. 88, No. 2, pp. 143-151 (2000).

[Non-Patent Document 4] J. Immunol., vol. 157, No. 8, pp. 3220-3222 (1996).

[Non-Patent Document 5] J. Immunol., vol. 166, No. 8, pp. 3542-3548 (2001).

[Non-Patent Document 6] Nature, vol. 380, No. 6575, pp. 630-633 (1996).

[Non-Patent Document 7] Science, vol. 265, No. 5179, pp. 1701-1706 (1994).

[Non-Patent Document 8] Clin. Exp. Allergy, vol. 29, No. 1, pp. 114-123 (1999).

[Non-Patent Document 9] Nucl. Acids Res., vol. 14, No. 20, pp. 7898-7914 (1986).

[Non-Patent Document 10] Cold Spring Harb. Symp. Quant. Biol., vol. 51, Pt. 1, pp. 611-624 (1986).

[Non-Patent Document 11] Ann. Rev. Immunol., vol. 14, pp. 649-681 (1996).

[Non-Patent Document 12] Genes Dev., vol. 9, No. 22, pp. 2723-2735 (1995).

[Non-Patent Document 13] Ann. Rev. Immunol., vol. 12, pp. 141-179 (1994).

[Non-Patent Document 14] Cell, Vol. 87, No. 1, pp. 13-20 (1996).

[Non-Patent Document 15] J. Mol. Med., vol. 82, No. 7, pp. 434-448 (2004).

[Non-Patent Document 16] J. Clin. Invest., vol. 107, No. 1, pp. 3-6 (2001).

[Non-Patent Document 17] J. Med. Chem., vol. 20, No. 6, pp. 826-829 (1977).

[Non-Patent Document 18] Ind. J. Exp. Biol., vol. 14, No. 3, pp. 332-333 (1976).

DISCLOSURE OF THE INVENTION

Problems to be Solved by the Invention

An object of the present invention is to provide a medicament for prophylactic and/or therapeutic treatment of diseases caused by an activation of STAT6 and/or NF-κB.

Means to Solve the Problems

The inventors of the present invention conducted various studies to solve the aforementioned objects. As a result, they found that salicylanilide compounds having structural features wherein the benzene ring which binds to the nitrogen atom is 3,4-disubstituted, and wherein the substituent in the 4-position is a group including a $C_{5-7}$ cycloalkyl group, a substituted $C_{5-7}$ cycloalkyl group, a 5 to 7-membered completely saturated heterocyclic group or a substituted 5 to 7-membered completely saturated heterocyclic group have strong inhibitory activity against activation of STAT6 and/or NF-κB and achieved the present invention.

The present invention thus provides:

(1) a compound represented by the following formula (I) or a salt thereof, or a hydrate thereof or a solvate thereof:

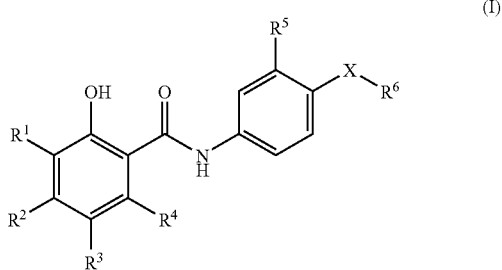

wherein $R^1$, $R^2$, $R^3$ and $R^4$ independently represent hydrogen atom, a halogen atom, cyano group, nitro group, a $C_{1-4}$ alkyl group, a halogenated $C_{1-4}$ alkyl group or a $C_{1-4}$ alkoxy group, $R^5$ represents a halogen atom, cyano group, a $C_{1-4}$ alkyl group, a halogenated $C_{1-4}$ alkyl group or a $C_{1-4}$ alkoxy group, $R^6$ represents a $C_{5-7}$ cycloalkyl group, a substituted $C_{5-7}$ cycloalkyl group, a 5 to 7-membered completely saturated heterocyclic group or a substituted 5 to 7-membered completely saturated heterocyclic group, X represents a single bond, oxygen atom, sulfur atom, $NR^7$, —O—$CH_2$— or —N($R^8$)—$CH_2$—, $R^7$ represents hydrogen atom or a $C_{1-4}$ alkyl group, or $R^7$ may combine with a substituent of $R^6$ to represent a single bond, methylene group or ethylene group, $R^8$ represents hydrogen atom, a $C_{1-4}$ alkyl group or a $C_{7-12}$ aralkyl group.

According to preferred embodiments of the present invention, provided are:

(2) the compound according to the aforementioned (1) or a salt thereof, or a hydrate thereof or a solvate thereof, wherein X is a single bond, oxygen atom, sulfur atom, $NR^7$, —O—$CH_2$— or —N($R^8$)—$CH_2$—, $R^6$ is a group represented by the following formula (II):

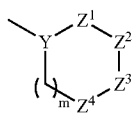

wherein Y represents CH or nitrogen atom, m represents 0, 1 or 2, $Z^1$, $Z^2$, $Z^3$ and $Z^4$ independently represent oxygen atom, sulfur atom, $NR^9$, $C(R^{10})(R^{11})$ or C=O, $R^9$ represents hydrogen atom, a $C_{1-4}$ alkyl group, a substituted $C_{1-4}$ alkyl group, a $C_{2-5}$ alkanoyl group, a substituted $C_{2-5}$ alkanoyl group or a $C_{7-12}$ aralkyl group, or $R^9$ may combine with $R^7$ to represent a single bond, methylene group or ethylene group, $R^{10}$ and $R^{11}$ independently represent hydrogen atom, hydroxy group, a $C_{1-4}$ alkyl group, a substituted $C_{1-4}$ alkyl group, $N(R^{12})(R^{13})$, carboxy group, carbamoyl group or a $C_{2-5}$ alkoxycarbonyl group, or $R^{10}$ may combine with $R^7$ to represent a single bond, methylene group or ethylene group, $R^{12}$ and $R^{13}$ independently represent hydrogen atom, a $C_{1-4}$ alkyl group or a substituted $C_{1-4}$ alkyl group, or $R^{12}$ may bind to $R^{13}$ to represent —$(CH_2)_n$—, n represents 4, 5 or 6;

(3) the compound according to the aforementioned (2) or a salt thereof, or a hydrate thereof or a solvate thereof, wherein the group represented by the aforementioned formula (II) is any one of the following (i), (ii) or (iii):

(i) Y is nitrogen atom;

(ii) Y is CH, three groups among $Z^1$, $Z^2$, $Z^3$ and $Z^4$ are independently $C(R^{10})(R^{11})$, and the remaining one group is $NR^9$;

(iii) Y is CH, $Z^1$, $Z^2$, $Z^3$ and $Z^4$ are independently $C(R^{10})(R^{11})$;

(4) the compound according to the aforementioned (3) or a salt thereof, or a hydrate thereof or a solvate thereof, wherein X is a single bond, Y is nitrogen atom;

(5) the compound according to the aforementioned (3) or a salt thereof, or a hydrate thereof or a solvate thereof, wherein X is oxygen atom, Y is CH, three groups among $Z^1$, $Z^2$, $Z^3$ and $Z^4$ are independently $C(R^{10})(R^{11})$, and the remaining one group is $NR^9$;

(6) the compound according to the aforementioned (3) or a salt thereof, or a hydrate thereof or a solvate thereof, wherein X is oxygen atom, Y is CH, $Z^1$, $Z^2$, $Z^3$ and $Z^4$ are independently $C(R^{10})(R^{11})$;

(7) the compound according to the aforementioned (3) or a salt thereof, or a hydrate thereof or a solvate thereof, wherein X is $NR^7$, Y is CH, three groups among $Z^1$, $Z^2$, $Z^3$ and $Z^4$ are independently $C(R^{10})(R^{11})$, and the remaining one group is $NR^9$;

(8) the compound according to the aforementioned (3) or a salt thereof, or a hydrate thereof or a solvate thereof, wherein X is $NR^7$, Y is CH, $Z^1$, $Z^2$, $Z^3$ and $Z^4$ are independently $C(R^{10})(R^{11})$;

(9) the compound according to the aforementioned (3) or a salt thereof, or a hydrate thereof or a solvate thereof, wherein X is —O—$CH_2$—, Y is CH, three groups among $Z^1$, $Z^2$, $Z^3$ and $Z^4$ are independently $C(R^{10})(R^{11})$, and the remaining one group is $NR^9$;

(10) the compound according to the aforementioned (3) or a salt thereof, or a hydrate thereof or a solvate thereof, wherein X is —$N(R^8)$—$CH_2$—, Y is CH, three groups among $Z^1$, $Z^2$, $Z^3$ and $Z^4$ are independently $C(R^{10})(R^{11})$, and the remaining one group is $NR^9$; and

(11) the compound according to the aforementioned (1) or a salt thereof, or a hydrate thereof or a solvate thereof, wherein $R^1$ and $R^2$ are independently hydrogen atom or a halogen atom, $R^3$ is hydrogen atom, a halogen atom, cyano group, nitro group, a $C_{1-4}$ alkyl group or a halogenated $C_{1-4}$ alkyl group, $R^4$ is hydrogen atom, $R^5$ is a halogen atom, cyano group, a $C_{1-4}$ alkyl group, a halogenated $C_{1-4}$ alkyl group or a $C_{1-4}$ alkoxy group, $R^6$ is cyclohexyl group; an amino substituted cyclohexyl group; a 5 to 7-membered completely saturated heterocyclic group selected from the group consisting of a pyrrolidinyl group, a piperidinyl group, a piperazinyl group, a morpholinyl group, a thiomorpholinyl group, an azepanyl group and a 1,4-diazepanyl group; or an aforementioned 5 to 7-membered completely saturated heterocyclic group substituted with the group selected from the group consisting of hydroxy group, a $C_{1-6}$ alkyl group, a $C_{7-12}$ aralkyl group, a $C_{2-7}$ alkanoyl group, carbamoyl group, amino group, a $C_{1-6}$ alkylamino group, a di-$C_{1-6}$ alkylamino group, oxo group, a pyrrolidinyl group, an amino substituted $C_{1-6}$ alkyl group and a piperidinyl substituted $C_{2-7}$ alkanoyl group, X is a single bond, oxygen atom, $NR^7$ or —O—$CH_2$—, $R^7$ is hydrogen atom.

From another aspect, the present invention provides:

(12) a medicament which comprises as an active ingredient a substance selected from the group consisting of a compound represented by the aforementioned formula (I), and a pharmacologically acceptable salt thereof, and a hydrate thereof and a solvate thereof;

(13) the medicament according to the aforementioned (13), which is used for prophylactic and/or therapeutic treatment of diseases caused by an activation of STAT6 and/or NF-κB; and

(14) a STAT6 and/or NF-κB activation inhibitor which comprises as an active ingredient a substance selected from the group consisting of a compound represented by the aforementioned formula (I), and a pharmacologically acceptable salt thereof, and a hydrate thereof and a solvate thereof.

From further another aspect, the present invention provides:

(15) a method of inhibiting activation of STAT6 and/or NF-B in a mammal including a human, which comprises the step of administering a compound represented by the aforementioned formula (I) or a salt thereof, or a hydrate thereof or a solvate thereof at a dose sufficient to inhibit activation of STAT6 and/or NF-κB; and

(16) a method for prophylactic and/or therapeutic treatment of diseases caused by an activation of STAT6 and/or NF-κB in a mammal including a human, which comprises the step of administering a compound represented by the aforemen- Furthermore, the present invention provides:

(17) a compound represented by the following formula (III):

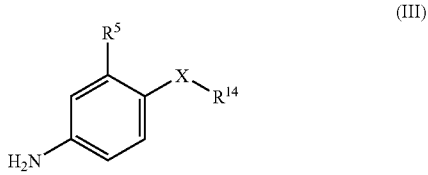

wherein $R^5$ represents a halogen atom, cyano group, a $C_{1-4}$ alkyl group, a halogenated $C_{1-4}$ alkyl group or a $C_{1-4}$ alkoxy group, $R^{14}$ represents cyclohexyl group; a $NR^{15}R^{16}$ substituted cyclohexyl group; a 5 to 7-membered completely saturated heterocyclic group selected from the group consisting of a pyrrolidinyl group, a piperidinyl group, a piperazinyl group, a thiomorpholinyl group, an azepanyl group and a 1,4-diazepanyl group, and those heterocyclic groups wherein the hydrogen atom of —NH— constituting the heterocyclic ring is substituted with a protecting group; an aforementioned 5 to 7-membered completely saturated heterocyclic group substituted with the group selected from the group consisting of a $C_{1-6}$ alkyl group, a $C_{7-12}$ aralkyl group, a $C_{2-7}$ alkanoyl group, a $C_{2-7}$ alkoxycarbonyl group, carbamoyl group, $NR^{17}R^{18}$, oxo group, a pyrrolidinyl group, a $NR^{15}R^{16}$ substituted $C_{1-6}$ alkyl group and a piperidinyl substituted $C_{2-7}$ alkanoyl group; or 1,4-dioxa-8-azaspiro[4,5]decan-8-yl group, X represents a single bond, oxygen atom, $NR^7$ or —O—$CH_2$—, $R^7$ represents hydrogen atom, $R^{15}$, $R^{16}$ and $R^{17}$ independently represent hydrogen atom or a protecting group, $R^{18}$ represents hydrogen atom, a protecting group or a $C_{1-6}$ alkyl group; and

(18) a compound represented by the following formula (IV):

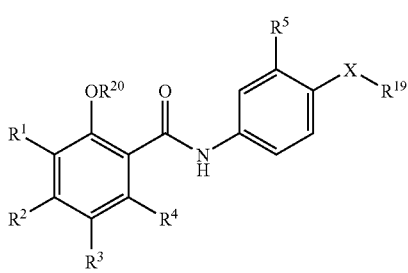

wherein $R^1$ and $R^2$ independently represent hydrogen atom or a halogen atom, $R^3$ represents hydrogen atom, a halogen atom, cyano group, nitro group, a $C_{1-4}$ alkyl group or a halogenated $C_{1-4}$ alkyl group, $R^4$ represents hydrogen atom, $R^5$ represents a halogen atom, cyano group, a $C_{1-4}$ alkyl group, a halogenated $C_{1-4}$ alkyl group or a $C_{1-4}$ alkoxy group, $R^{19}$ represents cyclohexyl group; a $NR^{15}R^{16}$ substituted cyclohexyl group; a 5 to 7-membered completely saturated heterocyclic group selected from the group consisting of a pyrrolidinyl group, a piperidinyl group, a piperazinyl group, a morpholinyl group, a thiomorpholinyl group, an azepanyl group and a 1,4-diazepanyl group, and those heterocyclic groups wherein the hydrogen atom of —NH— constituting the heterocyclic ring is substituted with a protecting group; an aforementioned 5 to 7-membered completely saturated heterocyclic group substituted with the group selected from the group consisting of a $C_{1-6}$ alkyl group, a $C_{7-12}$ aralkyl group, a $C_{2-7}$ alkanoyl group, a $C_{2-7}$ alkoxycarbonyl group, carbamoyl group, $NR^{17}R^{18}$, oxo group, a pyrrolidinyl group, a $NR^{15}R^{16}$ substituted $C_{1-6}$ alkyl group and a piperidinyl substituted $C_{2-7}$ alkanoyl group; or 1,4-dioxa-8-azaspiro[4,5]decan-8-yl group, X represents a single bond, oxygen atom, $NR^7$ or —O—$CH_2$—, $R^7$ represents hydrogen atom, $R^{15}$, $R^{16}$ and $R^{17}$ independently represent hydrogen atom or a protecting group, $R^{18}$ represents hydrogen atom, a protecting group or a $C_{1-6}$ alkyl group, $R^{20}$ represents a protecting group.

From further another aspect, the present invention provides:

use of the compound represented by the aforementioned formula (I) or a salt thereof, or a hydrate thereof or a solvate thereof for the manufacture of the aforementioned medicament;

a method of inhibiting activation of STAT6 and/or NF-κB in a mammal including a human, which comprises the step of administering the compound represented by the aforementioned formula (I) or a salt thereof, or a hydrate thereof or a solvate thereof at a dose sufficient to inhibit activation of STAT6 and/or NF-κB; and a method for prophylactic and/or therapeutic treatment of diseases caused by an activation of STAT6 and/or NF-κB in a mammal including a human, which comprises the step of administering the compound represented by the aforementioned formula (I) or a salt thereof, or a hydrate thereof or a solvate thereof at a dose sufficient to treat said diseases prophylactically and/or therapeutically.

BEST MODE FOR CARRYING OUT THE INVENTION

The terms used in the present specification have the following meanings.

As the halogen atom, any of fluorine atom, chlorine atom, bromine atom or iodine atom may be used unless otherwise specifically referred to.

The "alkyl group" or an alkyl moiety of the substituents containing the alkyl moiety may be straight chain, branched chain, cyclic, or combination thereof.

Examples of the "$C_{1-4}$ alkyl group" include, for example, methyl group, ethyl group, n-propyl group, isopropyl group, n-butyl group, isobutyl group, sec-butyl group, tert-butyl group, cyclopropyl group, cyclobutyl group and (cyclopropyl)methyl group.

Examples of the "halogenated $C_{1-4}$ alkyl group" include, for example, chloromethyl group, bromomethyl group, fluoromethyl group, dichloromethyl group, dibromomethyl group, difluoromethyl group, trichloromethyl group, tribromomethyl group, trifluoromethyl group, 2,2,2-trifluoroethyl group and pentafluoroethyl group.

Examples of the "$C_{1-4}$ alkoxyl group" include, for example, methoxy group, ethoxy group, n-propoxy group, isopropoxy group, n-butoxy group, isobutoxyl group, sec-butoxy group, tert-butoxy group, cyclopropoxy group, cyclobutoxy group and (cyclopropyl)methoxy group.

Examples of the "$C_{5-7}$ cycloalkyl group" include cyclopentyl group, cyclohexyl group and cycloheptyl group.

Examples of the "$C_{2-5}$ alkanoyl group" include, for example, acetyl group, propionyl group, butyryl group, isobutyryl group, valeryl group, isovaleryl group, pivaloyl group, (cyclopropyl)carbonyl group and (cyclobutyl)carbonyl group. In the definition, the "$C_2$ alkanoyl group" means acetyl group.

The "5 to 7-membered completely saturated heterocyclic group" comprises one to three hetero atoms as ring-constituting atoms. Examples of said "5 to 7-membered completely saturated heterocyclic group" include, for example, pyrrolidinyl group, imidazolidinyl group, pyrazolidinyl group, oxazolidinyl group, thiazolidinyl group, piperidinyl group, piperazinyl group, morpholinyl group, thiomorpholinyl group, azepanyl group, 1,4-diazepanyl group, 1,4-oxazepanyl group, 1,4-thiazepanyl group, tetrahydrofuranyl group, tetrahydrothiophenyl group, tetrahydropyranyl group and tetrahydrothiopyranyl group.

Examples of the "$C_{7-12}$ aralkyl group" include, for example, benzyl group, 1-phenethyl group, 2-phenethyl group, (naphthalen-1-yl)methyl group, (naphthalen-2-yl)methyl group, 1-(naphthalen-1-yl)ethyl group, 2-(naphthalen-1-yl)ethyl group, 1-(naphthalen-2-yl)ethyl group and 2-(naphthalen-2-yl)ethyl group.

Examples of the "$C_{2-5}$ alkoxycarbonyl group" include, for example, methoxycarbonyl group, ethoxycarbonyl group, n-propoxycarbonyl group, isobutoxycarbonyl group, sec-butoxycarbonyl group, tert-butoxycarbonyl group, cyclopropoxycarbonyl group, cyclobutoxycarbonyl group and (cyclopropyl)methoxycarbonyl group. In the definition, the "$C_2$ alkoxycarbonyl group" means methoxycarbonyl group.

In the following, compounds represented by the aforementioned formula (I) are explained specifically.

$R^1$, $R^2$, $R^3$ and $R^4$ independently represent hydrogen atom, a halogen atom, cyano group, nitro group, a $C_{1-4}$ alkyl group, a halogenated $C_{1-4}$ alkyl group or a $C_{1-4}$ alkoxy group.

$R^1$, $R^2$, $R^3$ and $R^4$ are preferably the following (a) or (b):

(a) $R^1$ and $R^2$ are hydrogen atom or a halogen atom, $R^3$ is hydrogen atom, a halogen atom, cyano group, nitro group, a $C_{1-4}$ alkyl group or a halogenated $C_{1-4}$ alkyl group, $R^4$ is hydrogen atom;

(b) two of $R^1$, $R^2$ and $R^3$ are hydrogen atom, and the remaining one group is a halogen atom, cyano group, nitro group, a $C_{1-4}$ alkyl group or a halogenated $C_{1-4}$ alkyl group, $R^4$ is hydrogen atom.

$R^5$ represents a halogen atom, cyano group, a $C_{1-4}$ alkyl group, a halogenated $C_{1-4}$ alkyl group or a $C_{1-4}$ alkoxy group.

$R^6$ represents a $C_{5-7}$ cycloalkyl group, a substituted $C_{5-7}$ cycloalkyl group, a 5 to 7-membered completely saturated heterocyclic group or a substituted 5 to 7-membered completely saturated heterocyclic group.

When $R^6$ is a $C_{5-7}$ cycloalkyl group or a substituted $C_{5-7}$ cycloalkyl group, said $C_{5-7}$ cycloalkyl group is preferably cyclohexyl group.

When $R^6$ is a 5 to 7-membered completely saturated heterocyclic group or a substituted 5 to 7-membered completely saturated heterocyclic group, said 5 to 7-membered completely saturated heterocyclic group is preferably a pyrrolidinyl group, a piperidinyl group, a piperazinyl group, a morpholinyl group, a thiomorpholinyl group, an azepanyl group or a 1,4-diazepanyl group. More preferably, said 5 to 7-membered completely saturated heterocyclic group is any one of the following groups.

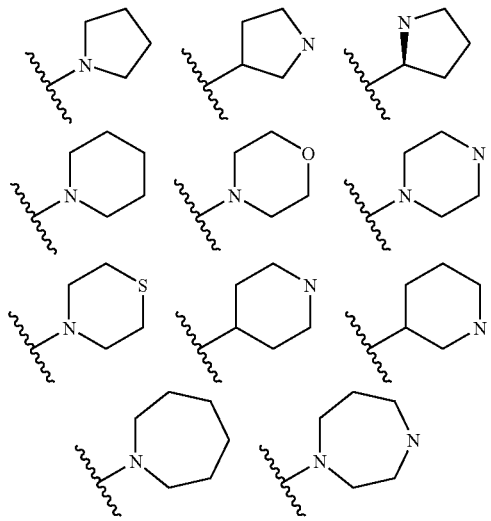

In the present specification, when a certain functional group is defined as "substituted", kinds, numbers, and positions of substituents existing in the functional groups are not particularly limited unless otherwise specifically referred to. Examples of these substituents include, for example, halogen atoms, cyano group, nitro group, hydroxy group, sulfanyl group, a $C_{1-6}$ alkyl group, a $C_{3-7}$ cycloalkyl group, a $C_{1-6}$ alkylene group (for example, methylene group and ethylene group), a $C_{2-6}$ alkenyl group (for example, vinyl group and allyl group), a $C_{2-6}$ alkynyl group (for example, ethynyl group and propargyl group), a $C_{6-10}$ aryl group (for example, phenyl group and naphthyl group), a $C_{7-12}$ aralkyl group (for example, benzyl group and naphthylmethyl group), a $C_{1-6}$ alkoxy group, a $C_{3-7}$ cycloalkoxy group (for example, cyclopropyloxy group), a $C_{2-6}$ alkenyloxy group (for example, allyloxy group), a $C_{2-6}$ alkynyloxy group (for example, propargyloxy group), a $C_{6-10}$ aryloxy group (for example, phenoxy group and naphthyloxy group), a $C_{7-12}$ aralkyloxy group (for example, benzyloxy group), formyl group, a $C_{2-7}$ alkanoyl group, a $C_{7-11}$ aroyl group (for example, benzoyl group and naphthoyl group), carboxy group, a $C_{2-7}$ alkoxycarbonyl group (for example, methoxycarbonyl group and ethoxycarbonyl group), carbamoyl group, a $C_{1-6}$ alkylsulfanyl group (for example, methylsulfanyl group), a $C_{6-10}$ arylsulfanyl group (for example, phenylsulfanyl group), a $C_{7-12}$ aralkylsulfanyl group (for example, benzylsulfanyl group), sulfo group, a $C_{1-6}$ alkylsulfonyl group (for example, methanesulfonyl group), a $C_{6-10}$ arylsulfonyl group (for example, benzenesulfonyl group), sulfamoyl group, amino group, a $C_{1-6}$ alkylamino group (for example, methylamino group), a di-$C_{1-6}$ alkylamino group (for example, dimethylamino group), formylamino group, a $C_{2-7}$ alkanoylamino group (for example, acetylamino group), a $C_{7-11}$ aroylamino group (for example, benzoylamino group), a $C_{2-7}$ alkoxycarbonylamino group (for example, methoxycarbonylamino group), a $C_{1-6}$ alkylsulfonylamino group (for example, methanesulfonylamino group), a $C_{6-10}$ arylsulfonylamino group (for example, benzenesulfonylamino group), amidino group, guanidino group, oxo group, thioxo group, a 3 to 14-membered heterocyclic group (for example, a 5 to 14-membered heteroaryl group such as furyl group, thienyl group, pyrrolyl group, isoxazolyl group, isothiazolyl group, pyrazolyl group, oxazolyl group, thiazolyl group, imidazolyl group, pyridyl group, pyrimidinyl group, pyrazinyl group, pyridazinyl group, benzo[b]furyl group, benzo[b]thienyl group, indolizinyl group, indolyl group, isoindolyl group, indazolyl group, purinyl group, quinolyl group, isoquinolyl group, naphthyridinyl group, quinoxalinyl group, quinazolinyl group, cinnolinyl group, pteridinyl group, carbazolyl group, β-carbolinyl group, phenoxazinyl group and phenothiazinyl group; a 5 to 10-membered partly saturated heterocyclic group such as pyrrolinyl group, imidazolinyl group, pyrazolinyl group, chromanyl group, isochromanyl group, indolinyl group, isoindolinyl group, tetrahydroquinolyl group and tetrahydroisoquinolyl group; and a 3 to 7-membered completely saturated heterocyclic group such as aziridinyl group, azetidinyl group, pyrrolidinyl group, imidazolidinyl group, pyrazolidinyl group, oxazolidinyl group, thiazolidinyl group, piperidinyl group, piperazinyl group, morpholinyl group, thiomorpholinyl group, azepanyl group, 1,4-diazepanyl group, 1,4-oxazepanyl group, 1,4-thiazepanyl group, tetrahydrofuranyl group, tetrahydrothiophenyl group, tetrahydropyranyl group and tetrahydrothiopyranyl group). These substituents may further be substituted with the aforementioned substituents. Examples of these substituents include, for example, a halogenated $C_{1-6}$ alkyl group, a halogenated $C_{1-6}$ alkoxy group (for example, trifluoromethoxy group), a $C_{3-7}$ cycloalkyl substituted $C_{1-6}$ alkyl group (for example, cyclopropylmethyl group), a hydroxy substituted $C_{1-6}$ alkyl group (for example, hydroxymethyl group), a carboxy substituted $C_{1-6}$ alkyl group (for example, carboxymethyl group).

When $R^6$ is a substituted $C_{5-7}$ cycloalkyl group, said substituent is preferably amino group. When $R^6$ is a substituted $C_{5-7}$ cycloalkyl group, said $R^6$ is preferably the following group.

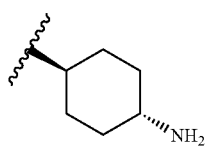

When $R^6$ is a substituted 5 to 7-membered completely saturated heterocyclic group, said substituent is preferably hydroxy group, a $C_{1-6}$ alkyl group, a $C_{7-12}$ aralkyl group, a $C_{2-7}$ alkanoyl group, carbamoyl group, amino group, a $C_{1-6}$ alkylamino group, a di-$C_{1-6}$ alkylamino group, oxo group, a pyrrolidinyl group, an amino substituted $C_{1-6}$ alkyl group or a piperidinyl substituted $C_{2-7}$ alkanoyl group. When $R^6$ is a substituted 5 to 7-membered completely saturated heterocyclic group, said $R^6$ is preferably any one of the following groups.

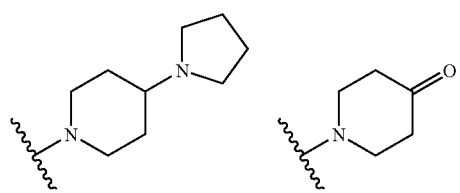

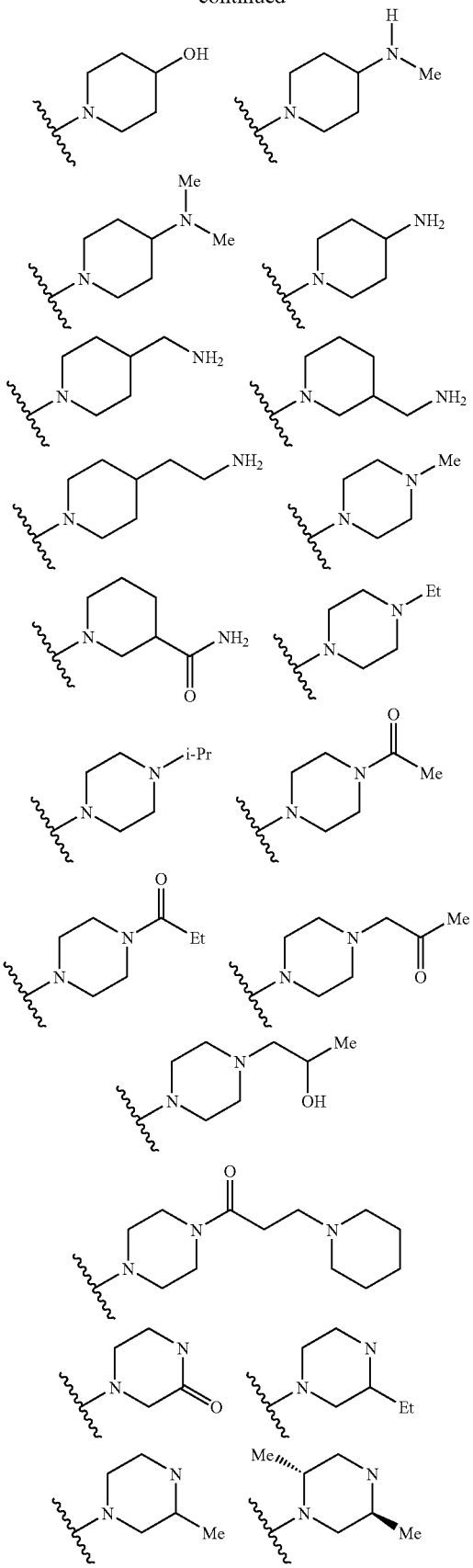

-continued

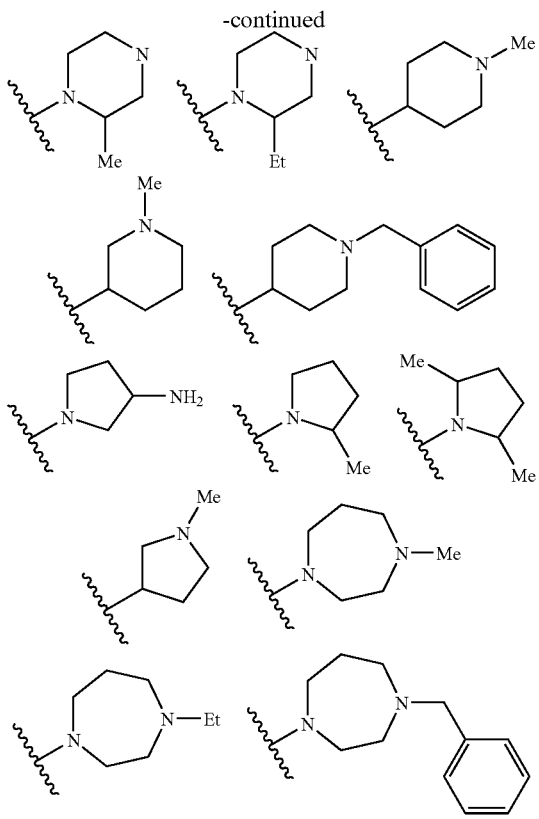

X represents a single bond, oxygen atom, sulfur atom, $NR^7$, —O—$CH_2$— or —$N(R^8)$—$CH_2$—.

$R^7$ represents hydrogen atom or a $C_{1-4}$ alkyl group, or $R^7$ may combine with a substituent of $R^6$ to represent a single bond, methylene group or ethylene group.

$R^6$ is preferably a group represented by the following formula (II):

(II)

wherein Y represents CH or nitrogen atom, m represents 0, 1 or 2, $Z^1$, $Z^2$, $Z^3$ and $Z^4$ independently represent oxygen atom, sulfur atom, $NR^9$, $C(R^{10})(R^{11})$ or C=O, $R^9$ represents hydrogen atom, a $C_{1-4}$ alkyl group, a substituted $C_{1-4}$ alkyl group, a $C_{2-5}$ alkanoyl group, a substituted $C_{2-5}$ alkanoyl group or a $C_{7-12}$ aralkyl group, or $R^9$ may combine with $R^7$ to represent a single bond, methylene group or ethylene group, $R^{10}$ and $R^{11}$ independently represent hydrogen atom, hydroxy group, a $C_{1-4}$ alkyl group, a substituted $C_{1-4}$ alkyl group, $N(R^{12})(R^{13})$, carboxy group, carbamoyl group or a $C_{2-5}$ alkoxycarbonyl group, or $R^{10}$ may combine with $R^7$ to represent a single bond, methylene group or ethylene group, $R^{12}$ and $R^{13}$ independently represent hydrogen atom, a $C_{1-4}$ alkyl group or a substituted $C_{1-4}$ alkyl group, or $R^{12}$ may bind to $R^{13}$ to represent —$(CH_2)_n$—, n represents 4, 5 or 6.

When $R^9$ is a substituted $C_{1-4}$ alkyl group, said substituent is preferably hydroxy group, phenyl group, oxo group or piperidinyl group.

When $R^9$ is a substituted $C_{2-5}$ alkanoyl group, said substituent is preferably a piperidinyl group.

$R^9$ is preferably hydroxy group, a $C_{1-4}$ alkyl group, a hydroxy substituted $C_{1-4}$ alkyl group, a phenyl substituted $C_{1-4}$ alkyl group, a oxo substituted $C_{1-4}$ alkyl group, a $C_{1-4}$ alkyl group substituted with oxo group and piperidinyl group, a $C_{2-5}$ alkanoyl group, a piperidinyl substituted $C_{2-5}$ alkanoyl group or a $C_{7-12}$ aralkyl group.

When $R^{10}$ or $R^{11}$ is a substituted $C_{1-4}$ alkyl group, said substituent is preferably amino group or oxo group.

$R^{10}$ or $R^{11}$ are preferably hydrogen atom, hydroxy group, a $C_{1-4}$ alkyl group, an amino substituted $C_{1-4}$ alkyl group, a $C_{1-4}$ alkyl group substituted with amino group and oxo groups $N(R^{12})(R^{13})$ or carbamoyl group.

$R^{12}$ and $R^{13}$ are preferably hydrogen atom or a $C_{1-4}$ alkyl group, or $R^{12}$ binds to $R^{13}$ to represent —$(CH_2)_n$—.

n is preferably 4.

The group represented by the aforementioned formula (II) is preferably any one of the following (i), (ii) or (iii):

(i) Y is nitrogen atom;

(ii) Y is CH, three groups among $Z^1$, $Z^2$, $Z^3$ and $Z^4$ are independently $C(R^{10})(R^{11})$, and the remaining one group is $NR^9$; or (iii) Y is CH, $Z^1$, $Z^2$, $Z^3$ and $Z^4$ are independently $C(R^{10})(R^{11})$.

When X is a single bond, $R^6$ is a group represented by the aforementioned formula (II), said group represented by the aforementioned formula (II) is preferably a group wherein Y is nitrogen atom.

When X is oxygen atom, $R^6$ is a group represented by the aforementioned formula (II), said group represented by the aforementioned formula (II) is preferably a group wherein Y is CH, $Z^1$, $Z^2$, $Z^3$ and $Z^4$ are the following (A) or (B):

(A) three groups among $Z^1$, $Z^2$, $Z^3$ and $Z^4$ are independently $C(R^{10})(R^{11})$, and the remaining one group is $NR^9$;

(B) $Z^1$, $Z^2$, $Z^3$ and $Z^4$ are independently $C(R^{10})(R^{11})$.

When X is $NR^7$, $R^6$ is a group represented by the aforementioned formula (II), said group represented by the aforementioned formula (II) is preferably a group wherein Y is CH, $Z^1$, $Z^2$, $Z^3$ and $Z^4$ are the following (a) or (b):

(a) three groups among $Z^1$, $Z^2$, $Z^3$ and $Z^4$ are independently $C(R^{10})(R^{11})$, and the remaining one group is $NR^9$;

(b) $Z^1$, $Z^2$, $Z^3$ and $Z^4$ are independently $C(R^{10})(R^{11})$.

When X is —O—$CH_2$—, $R^6$ is a group represented by the aforementioned formula (II), said group represented by the aforementioned formula (II) is preferably a group wherein Y is CH, three groups among $Z^1$, $Z^2$, $Z^3$ and $Z^4$ are independently $C(R^{10})(R^{11})$, and the remaining one group is $NR^9$.

When X is —$N(R^8)$—$CH_2$—, $R^6$ is a group represented by the aforementioned formula (II), said group represented by the aforementioned formula (II) is preferably a group wherein Y is CH, three groups among $Z^1$, $Z^2$, $Z^3$ and $Z^4$ are independently $C(R^{10})(R^{11})$, and the remaining one group is $NR^9$.

The compounds represented by the aforementioned formula (I) may form salts. Examples of pharmacologically acceptable salts include, when acidic groups exist, metal salts such as lithium salt, sodium salt, potassium salt, magnesium salt, calcium salts, or ammonium salts such as ammonium salt, methylammonium salt, dimethylammonium salt, trimethylammonium salt, dicyclohexylammonium salt, and when basic groups exist, mineral acid salts such as hydrochloride, hydrobromide, hydrosulfate, nitrate, phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, lactate. Salts may sometimes be formed with amino acids such as glycine. As active ingredients of the medicament of the present invention, pharmacologically acceptable salts may also be suitably used.

The compounds or salts thereof represented by the aforementioned formula (I) may exist as hydrates or solvates. As active ingredients of the medicament of the present invention, any of the aforementioned substances may be used. Furthermore, the compounds represented by the aforementioned formula (I) may sometimes have one or more asymmetric carbons, and may exist as stereoisomers such as optically active substance and diastereomer. As active ingredients of the medicament of the present invention, pure forms of stereoisomers, arbitrary mixture of enantiomers or diastereomers, racemates and the like may be used.

Furthermore, when the compounds represented by the aforementioned formula (I) may exist as a tautomer. As active ingredients of the medicament of the present invention, pure forms of tautomers or a mixture thereof may be used. When the compounds represented by the aforementioned formula (I) have olefinic double bonds, the configuration may be in either E or Z, and as active ingredients of the medicament of the present invention, geometrical isomer in either of the configurations or a mixture thereof may be used.

Examples of the preferred compounds as active ingredients of the medicaments of the present invention are shown below. However, the active ingredients of the medicaments of the present invention are not limited to the following compounds.

The abbreviations used in the following tables have the following meanings.

Me: methyl group, Et: ethyl group, i-Pr: isopropyl group, OMe: methoxy group, OEt: ethoxy group.

TABLE 1

| Compound Number | | |
|---|---|---|
| 1 | 2-methyl-4-chlorophenol | 4-(2-fluoro-4-methylphenyl)morpholine |
| 2 | 2-methyl-4-chlorophenol | 1-(2-fluoro-4-methylphenyl)piperidine |
| 3 | 2-methyl-4-chlorophenol | 4-(2-trifluoromethyl-4-methylphenyl)morpholine |

TABLE 1-continued
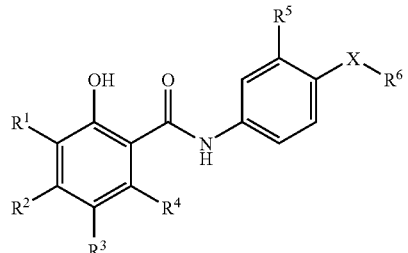
| Compound Number | | |
|---|---|---|
| 4 | 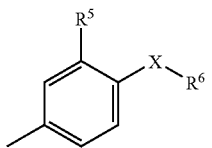 | 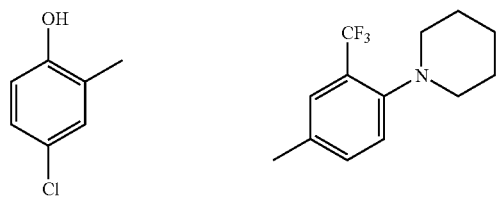 |
| 5 | 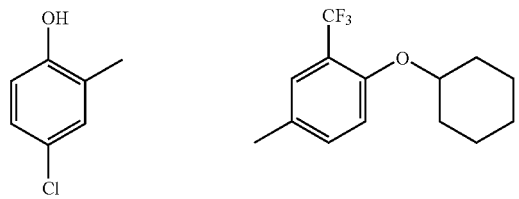 | 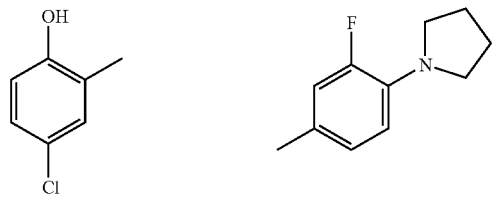 |
| 6 | 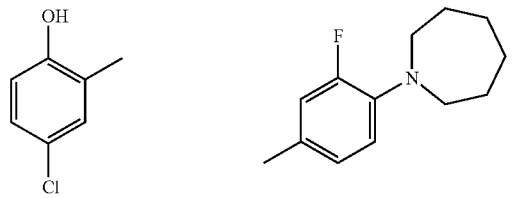 | 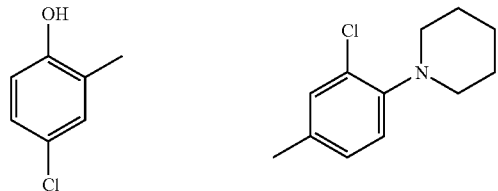 |
| 7 | | |
| 8 | | |

TABLE 1-continued
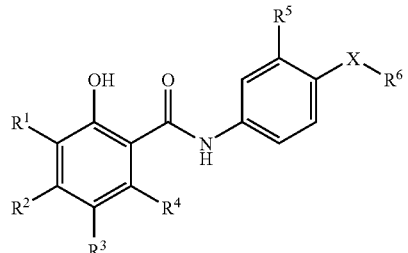
| Compound Number | | |
|---|---|---|
| 9 | 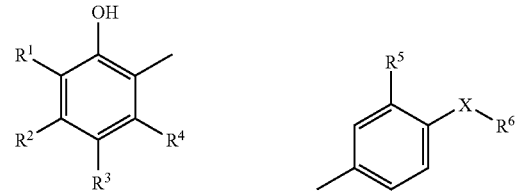 | 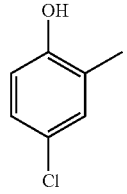 |
| 10 | 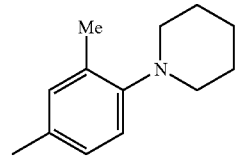 | 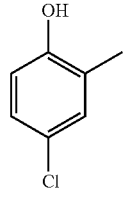 |
| 11 | 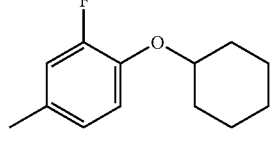 | 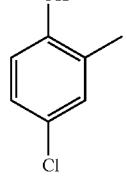 |
| 12 | 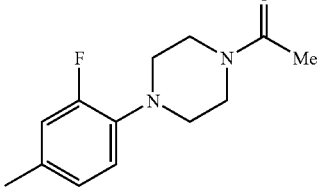 | 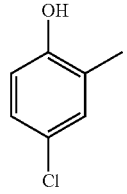 |
| 13 | 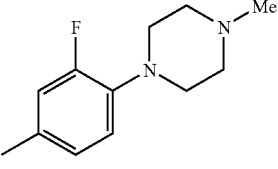 | 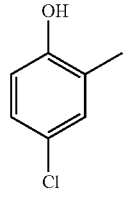 |

TABLE 1-continued
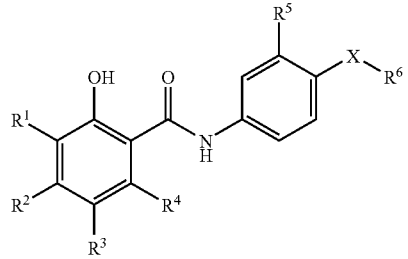
| Compound Number | 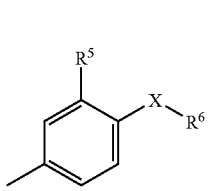 | 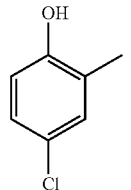 |
|---|---|---|
| 14 | 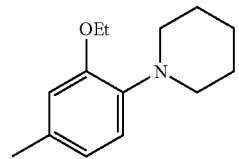 | 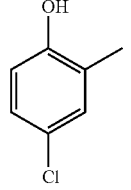 |
| 15 | 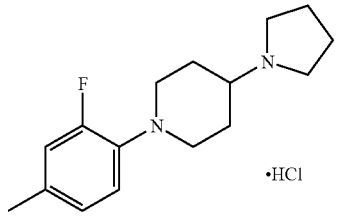 | 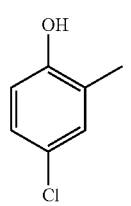 |
| 16 | 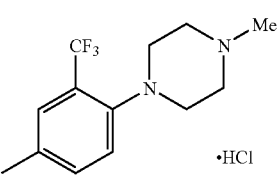 | 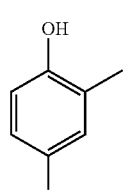 |
| 17 | 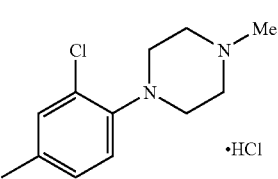 | 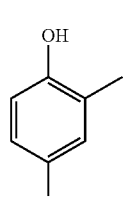 |
| 18 | | 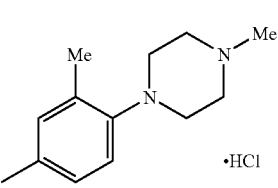 |

TABLE 1-continued
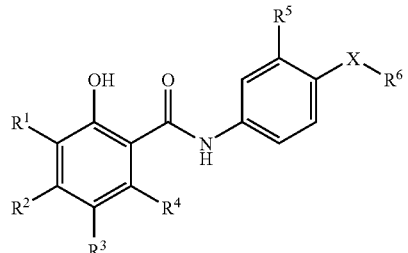
| Compound Number | | |
|---|---|---|
| 19 | 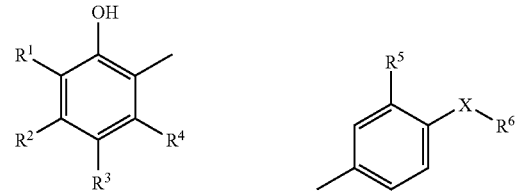 | 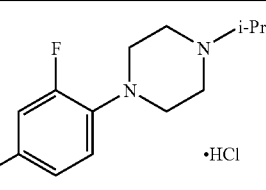 •HCl |
| 20 | 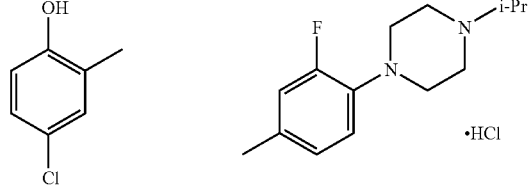 | 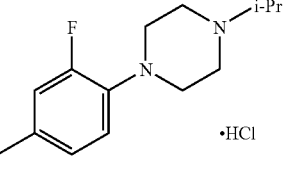 •2HCl |
| 21 | 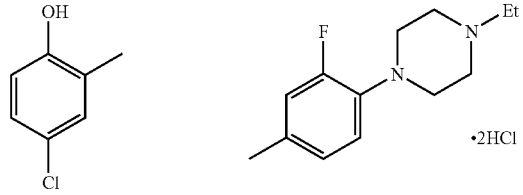 | 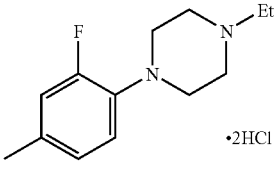 •2HCl |
| 22 | 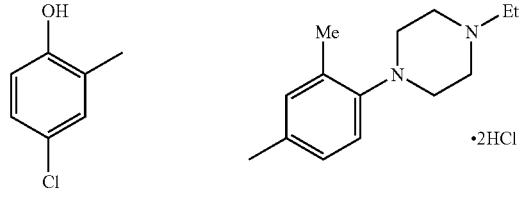 | 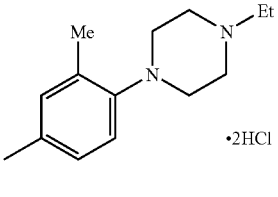 |
| 23 | 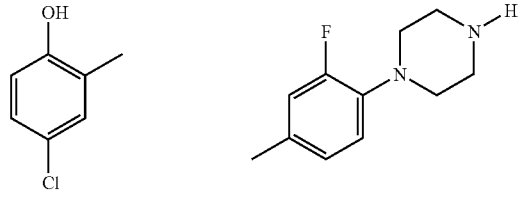 | 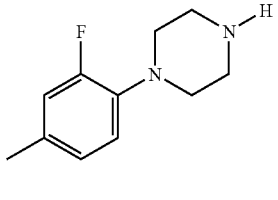 |

TABLE 1-continued
| Compound Number | 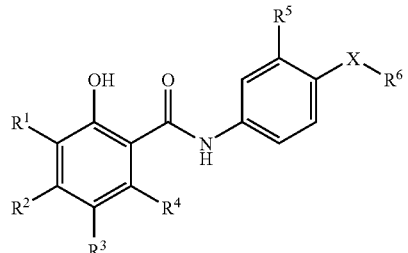 | 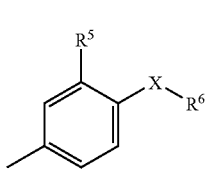 |
|---|---|---|
| 24 | 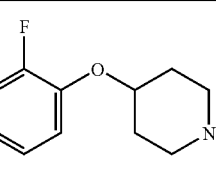 | 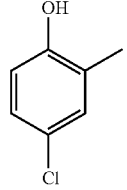 |
| 25 | 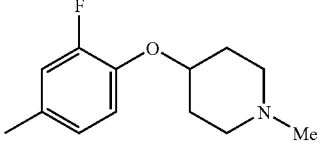 | 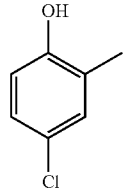 |
| 26 | 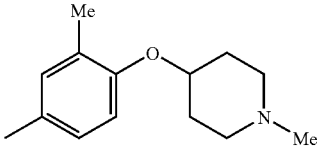 | 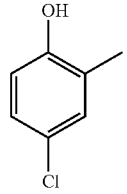 |
| 27 | 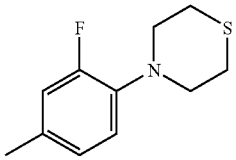 | 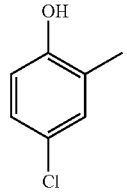·HCl |
| 28 | 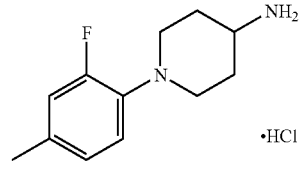 | 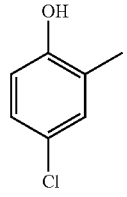 |

TABLE 1-continued
| Compound Number | 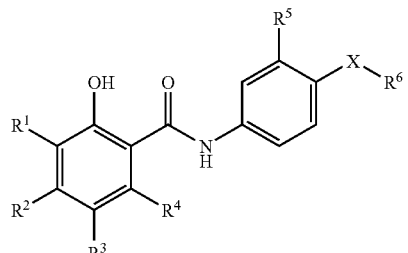 | 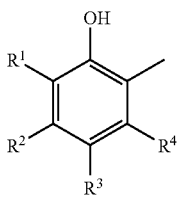 |
|---|---|---|
| 29 | 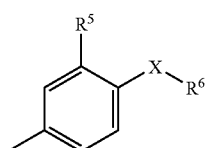 | 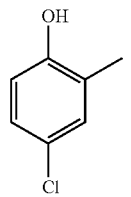 •HCl |
| 30 | 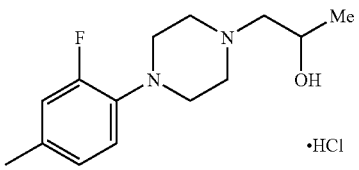 | 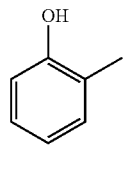 •HCl |
| 31 | 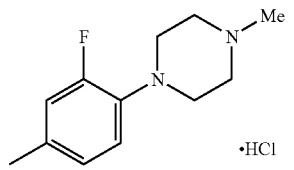 | 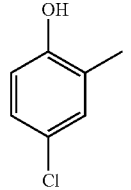 |
| 32 | 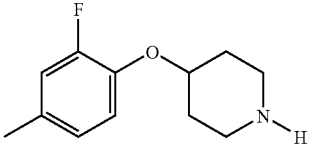 | 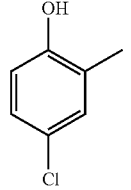 •HCl |
| 33 | 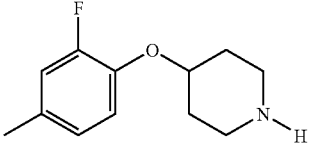 | 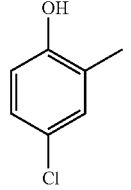 |

TABLE 1-continued
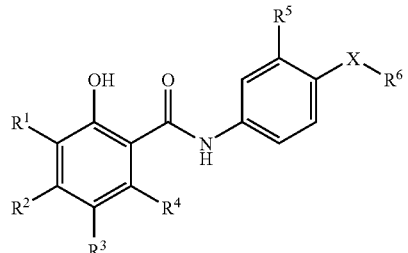
| Compound Number | | |
|---|---|---|
| 34 | 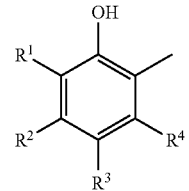 | 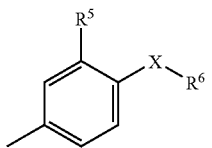 |
| 35 | 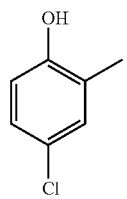 | 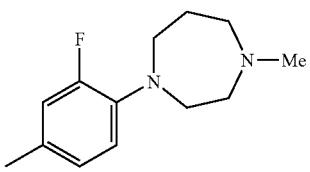 |
| 36 | 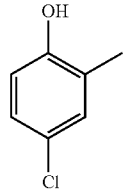 | 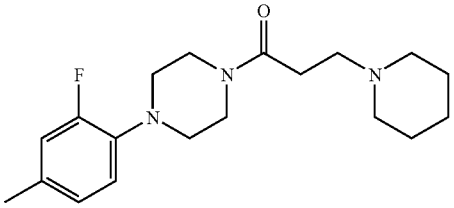 |
| 37 | 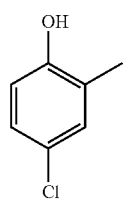 | 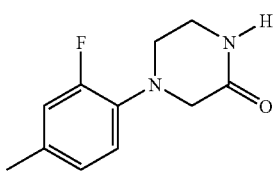 |
| 38 | 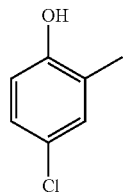 | 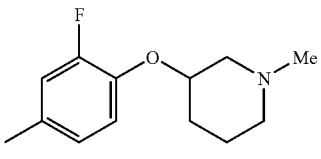 |

TABLE 1-continued
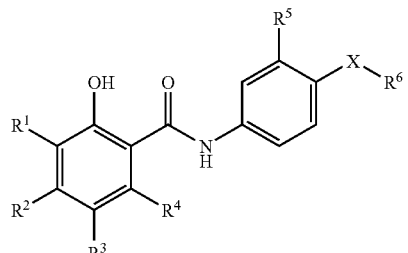
| Compound Number | 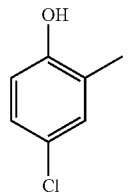 | 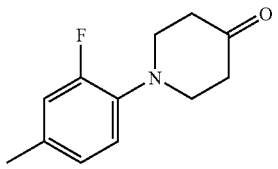 |
|---|---|---|
| 39 | 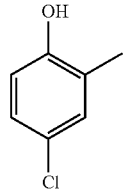 | 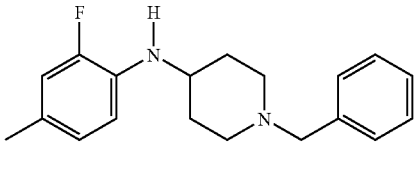 |
| 40 | | 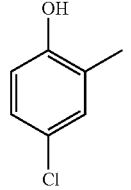 |
| 41 | | 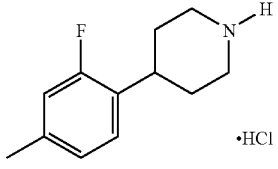 •HCl |
| 42 | | 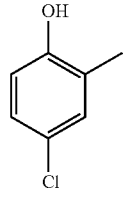 |
| 43 | | 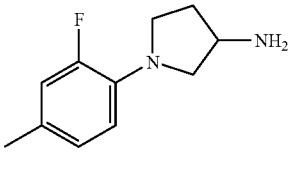 |

TABLE 1-continued
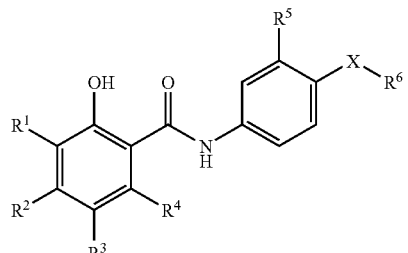
| Compound Number | | |
|---|---|---|
| 44 | | |
| 45 | | ·HCl |
| 46 | | ·HCl |
| 47 | | ·HCl |
| 48 | | |

TABLE 1-continued

| Compound Number | R¹,R²,R³,R⁴ phenol part | R⁵,X,R⁶ aniline part |
|---|---|---|
| 49 | 2-methyl-4-chlorophenol | 2-fluoro-4-methyl-phenoxymethyl-piperidine (NH) ·HCl |
| 50 | 2-methyl-4-chlorophenol | 2-fluoro-4-methyl-phenoxymethyl-(N-Me)-piperidine |
| 51 | 2-methyl-4-chlorophenol | 2-fluoro-4-methyl-phenoxymethyl-4-(N-Me)-piperidine |
| 52 | 2-methyl-4-chlorophenol | 1-(2-fluoro-4-methylphenyl)-4-benzyl-[1,4]diazepane |
| 53 | 2-methyl-4-chlorophenol | 1-(2-fluoro-4-methylphenyl)-4-ethyl-[1,4]diazepane |

TABLE 1-continued
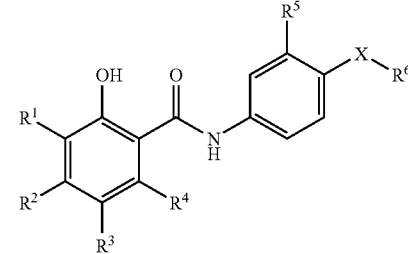
| Compound Number | | |
|---|---|---|
| 54 | 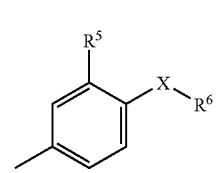 | 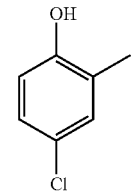 |
| 55 | 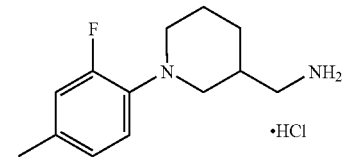 | 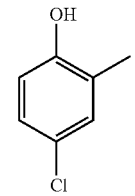 |
| 56 | 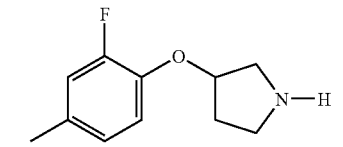 | 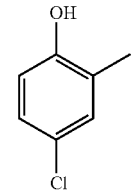 |
| 57 | 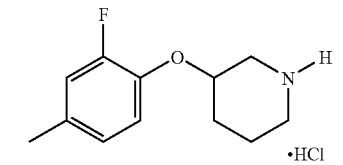 | 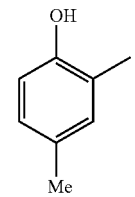 |
| 58 | 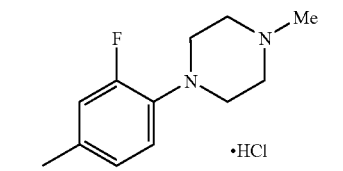 | 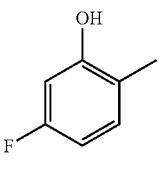 |

TABLE 1-continued

| Compound Number | R¹, R², R³, R⁴ substituents on phenol ring | R⁵, R⁶, X substituents on aniline ring |
|---|---|---|
| 59 | 2-methyl-4-fluorophenol | 2-fluoro-4-methyl-1-(4-methylpiperazin-1-yl)benzene · HCl |
| 60 | 6-chloro-2-methylphenol | 2-fluoro-4-methyl-1-(4-methylpiperazin-1-yl)benzene · HCl |
| 61 | 5-chloro-2-methylphenol | 2-fluoro-4-methyl-1-(4-methylpiperazin-1-yl)benzene · HCl |
| 62 | 2-methyl-4-(trifluoromethyl)phenol | 2-fluoro-4-methyl-1-(4-methylpiperazin-1-yl)benzene · HCl |
| 63 | 4-chloro-2-methylphenol | 1-(2-fluoro-4-methylphenyl)-4-(2-aminoethyl)piperidine · HCl |

TABLE 1-continued
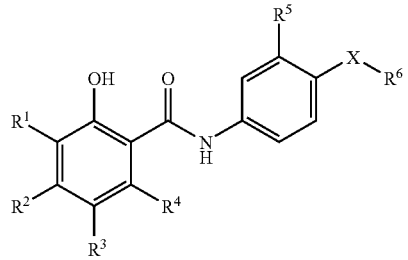
| Compound Number | | |
|---|---|---|
| 64 | 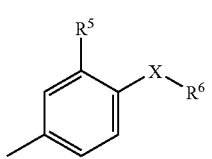 |  |
| 65 | 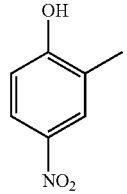 | 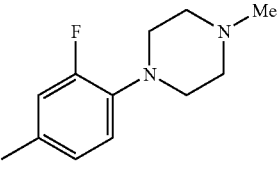 |
| 66 | 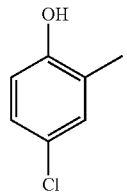 | 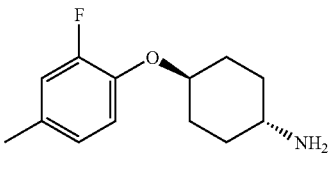 |
| 67 | 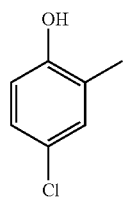 | 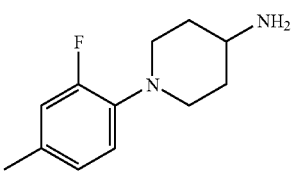 ·HCl |
| 68 | 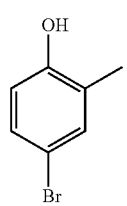 | 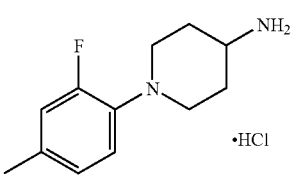 |

TABLE 1-continued
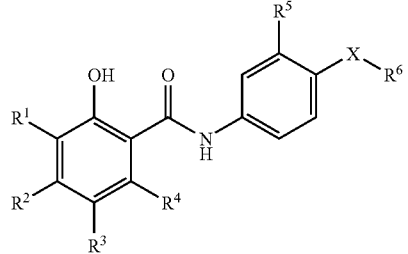
| Compound Number | | |
|---|---|---|
| 69 | 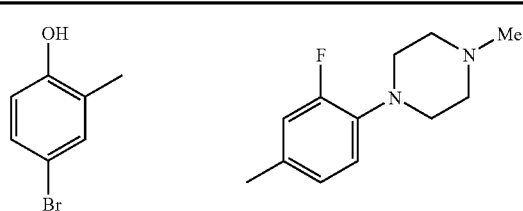 | 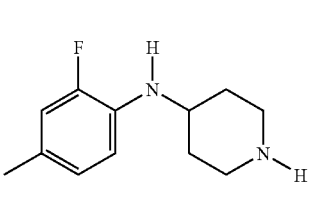 |
| 70 | | |
| 71 | | |
| 72 | | |
| 73 | | |

TABLE 1-continued
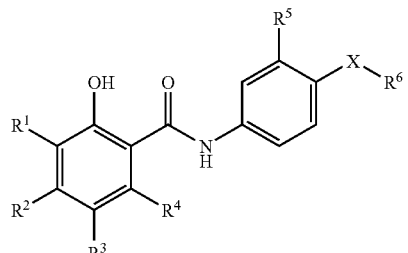
| Compound Number | 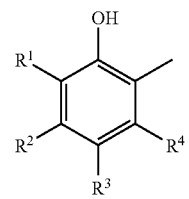 | 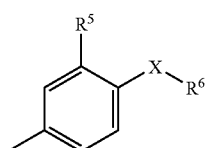 |
|---|---|---|
| 74 | 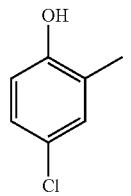 | 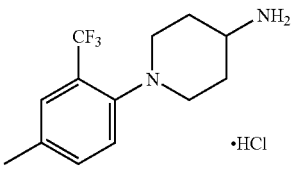 |
| 75 | 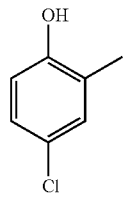 | 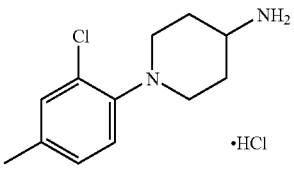 |
| 76 | 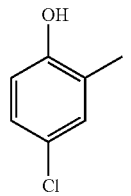 | 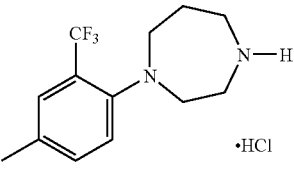 |
| 77 | 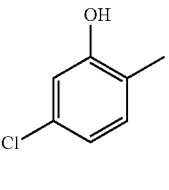 | 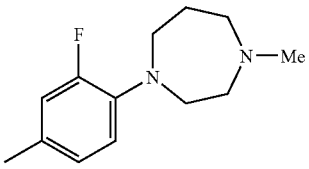 |
| 78 | 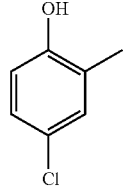 | 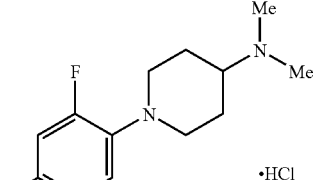 |

TABLE 1-continued
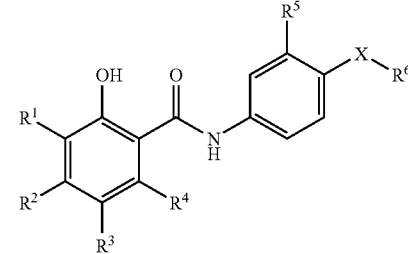
| Compound Number | | |
|---|---|---|
| 79 | 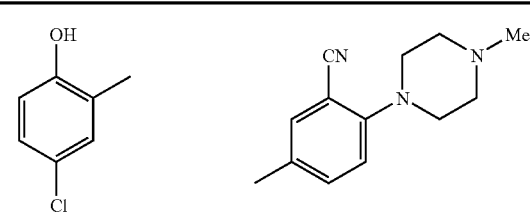 | |
| 80 | | |
| 81 | | |
| 82 | | |
| 83 | 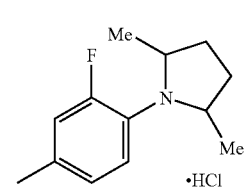 | |

TABLE 1-continued

| Compound Number | (left aryl group) | (right aryl group) |
|---|---|---|
| 84 | 2-methyl-4-chlorophenol | 1-(2-fluoro-4-methylphenyl)-2,5-dimethylpyrrolidine |
| 85 | 2-methyl-4-chlorophenol | (2R,5S)-1-(2-fluoro-4-methylphenyl)-2,5-dimethylpiperazine · 2HCl |
| 86 | 2-methyl-4-bromophenol | 1-(2-fluoro-4-methylphenyl)-4-methyl-[1,4]diazepane |
| 87 | 2-methyl-4-bromophenol | 1-(2-fluoro-4-methylphenyl)-[1,4]diazepane |
| 88 | 2-methyl-4-chlorophenol | 1-(2-fluoro-4-methylphenyl)-2-methylpiperazine · HCl |

TABLE 1-continued
| Compound Number | | |
|---|---|---|
| 89 | (2-methyl-4-chlorophenol) | (1-(2-fluoro-4-methylphenyl)-2-ethylpiperazine · HCl) |
| 90 | (2-methyl-4-cyanophenol) | (1-(2-fluoro-4-methylphenyl)-4-methylpiperazine · HCl) |
The compounds represented by the general formula (I) can be prepared, for example, by a method shown below.
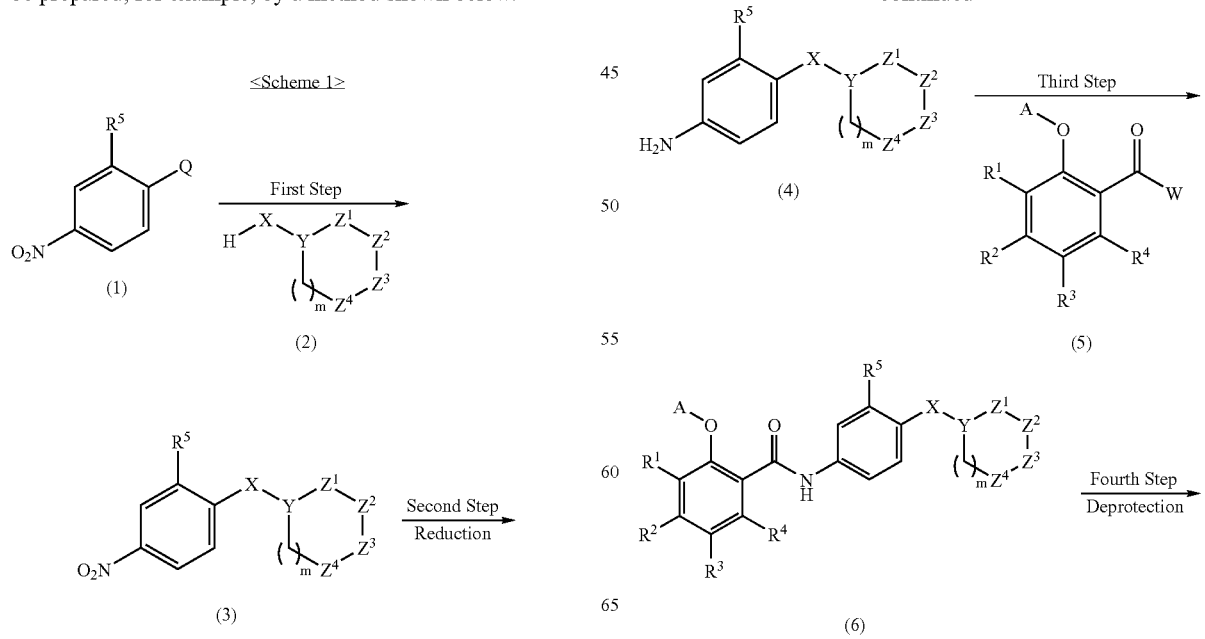

-continued

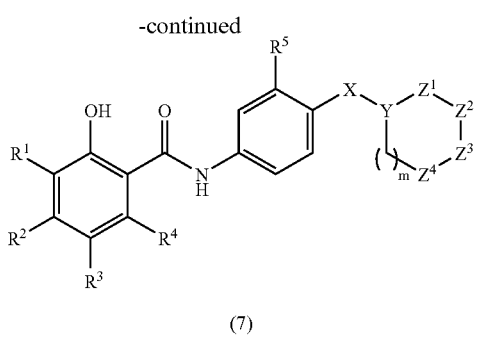

(7)

wherein

Q represents a halogen atom,

A represents hydrogen atom, or a protecting group for hydroxy group,

W represents hydroxy group or a leaving group such as a halogen atom, each of X, $R^1$, $R^2$, $R^3$, $R^4$, $R^5$, Y, $Z^1$, $Z^2$, $Z^3$, $Z^4$ and m has the same meaning as that described above, provided that when X is a single bond, Y is a nitrogen atom.

<First Step>

The nitrobenzene derivative (3) can be prepared by reacting the 4-halogenated nitrobenzene derivative (1) with the cyclic compound (2). This reaction is carried out without solvent or in a solvent, in the presence of or absence of a base, at a reaction temperature of from 0° C. to 180° C., preferably at a temperature of from 0° C. to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; acetonitrile and the like.

<Second Step>

The aniline derivative (4) can be prepared by reduction of the nitrobenzene derivative (3) obtained in the first step. As the reduction reaction, for example, (i) catalytic hydrogenation reaction using noble metal catalysts, and (ii) reduction reaction using metals or metal salts may be used.

(i) Catalytic Hydrogenation Reaction

This reaction is carried out in a solvent under hydrogen atmosphere (from normal pressure to 50 atm), in the presence of a noble metal catalyst, at a reaction temperature of from 0° C. to 180° C., preferably at a temperature of from 0° C. to the boiling point of the solvent.

As the noble catalyst, examples include platinum oxide, Raney nickel, palladium on activated charcoal and the like.

As the solvent, any solvent can be used as long as it does not inhibit the reaction, and examples include, for example, alcohols such as methanol and ethanol; ethers such as tetrahydrofuran, 1,2-dimethoxyethane and 1,4-dioxane; ethyl acetate; water and the like.

(ii) Reduction Reaction Using Metals or Metal Salts

This reaction is carried out in a solvent, in the presence of a metal or a metal salt, in the presence of or absence of an acid, at a reaction temperature of from 0° C. to the boiling point of the solvent.

As the metal, examples include iron (iron powder), tin and the like.

As the metal salt, examples include tin(II) chloride and the like.

As the acid, examples include organic acids such as acetic acid; inorganic acids such as hydrochloric acid.

As the solvent, any solvent can be used as long as it does not inhibit the reaction, and examples include, for example, alcohols such as methanol and ethanol; water and the like.

<Third Step (Method 1)>

The amide derivative (6) can be prepared by reacting the aniline derivative (4) obtained in the second step with the carboxylic acid derivative (5) wherein W is hydroxy group. This reaction is carried out in a solvent, in the presence of an acid halogenating agent or a dehydrocondensating agent, in the presence of or absence of a base, at a reaction temperature of from 0° C. to 180° C., preferably at a temperature of from 0° C. to the boiling point of the solvent.

As the acid halogenating agent reagent, examples include, for example, thionyl chloride, thionyl bromide, sulfuryl chloride, phosphorus oxychloride, phosphorus trichloride, phosphorus pentachloride and the like. When A is hydrogen atom, phosphorus trichloride is preferable, and when A is acetyl group or the like, phosphorus oxychloride is preferable.

As the dehydrocondensating agent, examples include, for example, N,N'-dicyclohexylcarbodiimide, 1-ethyl-3-(3-dimethylaminopropyl)carbodiimide hydrochloride, diphenylphosphorylazide and the like.

As the base, examples include inorganic bases such as sodium carbonate, potassium carbonate and sodium hydrogencarbonate; and organic bases such as 4-dimethylaminopyridine, pyridine, triethylamine, diisopropylethylamine, N-methylmorpholine and N,N'-diethylaniline.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; aromatic solvents such as benzene, toluene, monochlorobenzene and o-dichlorobenzene; amides such as dimethylformamide and N-methylpyrrolidone; acetonitrile and the like. When the reaction is carried out in the presence of phosphorus trichloride, toluene, monochlorobenzene and o-dichlorobenzene are preferable.

<Third Step (Method 2)>

The amide derivative (6) can be prepared by reacting the aniline derivative (4) obtained in the second step with the carboxylic acid derivative (5) wherein W is a leaving group such as a halogen atom. This reaction is carried out in a solvent, in the presence of a base, at a reaction temperature of from 0° C. to 180° C., preferably at a temperature of from 0° C. to the boiling point of the solvent.

As the base, examples include inorganic bases such as potassium carbonate, sodium carbonate and sodium hydrogencarbonate; and organic bases such as pyridine, triethylamine and diisopropylethylamine.

As the solvent, any solvent can be used as long as it does not inhibit the reaction, and examples include, for example, halogenated solvents such as dichloromethane and dichloroethane; ethers such as tetrahydrofuran, 1,2-dimethoxyethane and 1,4-dioxane; and amides such as dimethylformamide and N-methylpyrrolidone.

<Fourth Step>

In the amide derivatives (6), when A is a protecting group for hydroxy group, the final target compound (7) can be prepared by deprotecting reaction.

As the protecting group for hydroxy group, for example, acetyl group, benzoyl group, methyl group, methoxymethyl group, (2-methoxyethoxy)methyl group, benzyl group and the like may be used. As the deprotecting reaction, various well-known methods can be used. An example of documents where deprotecting reactions are described detailedly and specifically includes, for example, the following document.

Protective Groups in Organic Synthesis, 3rd Edition, 1999, John Wiley & Sons, Inc.

In the aforementioned (1) to (6), the groups represented by X, $R^1$, $R^2$, $R^3$, $R^4$, $R^5$, Y, $Z^1$, $Z^2$, $Z^3$ and $Z^4$ may be protected by protecting groups. Introduction of the protecting group and deprotection can be carried out in an appropriate process among each process represented by the aforementioned <Scheme 1>.

Furthermore, in the aforementioned (1) to (6), when the group represented by X, $R^1$, $R^2$, $R^3$, $R^4$, $R^5$, $Z^1$, $Z^2$, $Z^3$ or $Z^4$ can be converted into another functional group, conversion of the functional group can be carried out by a method which is well known to those skilled in the art in an appropriate process among each process represented by the aforementioned <Scheme 1>.

The compounds represented by the general formula (I), wherein X is a single bond, $R^6$ is a group represented by the aforementioned formula (II), Y is CH, three groups among $Z^1$, $Z^2$, $Z^3$ and $Z^4$ are $CH_2$ and the remaining one group is NH, and m is 1 can be prepared, for example, by a method shown below.

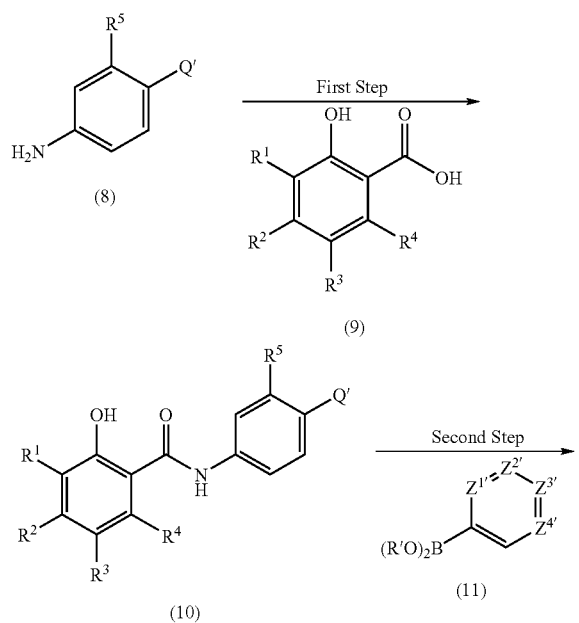

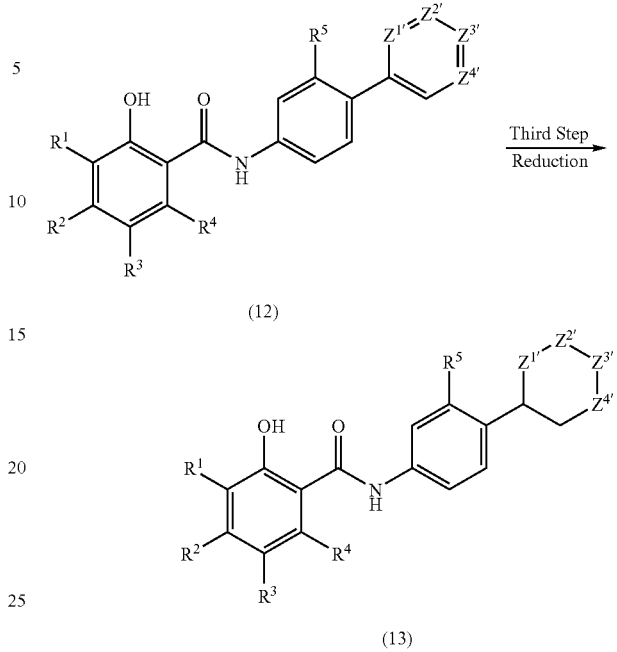

wherein

Q' represents bromine atom or iodine atom,

R' represents hydrogen atom or an alkyl group,

W represents hydroxy group or a leaving group such as a halogen atom, three groups among $Z^{1'}$, $Z^{2'}$, $Z^{3'}$ and $Z^{4'}$ represent CH and the remaining one represents nitrogen atom, three groups among $Z^1$, $Z^2$, $Z^3$ and $Z^4$ represent $CH_2$ and the remaining one represents NH, each of $R^1$, $R^2$, $R^3$, $R^4$ and $R^5$ has the same meaning as that described above.

<First Step>

The salicylanilide derivative (10) can be prepared by reacting the 4-bromo- or 4-iodoaniline derivative (8) with the salicylic acid derivative (9). This reaction is carried out in a solvent, in the presence of an acid halogenating agent, at a reaction temperature of from 0° C. to the boiling point of the solvent.

As the acid halogenating agent reagent, examples include, for example, phosphorus trichloride and the like.

As the solvent, any solvent can be used as long as it does not inhibit the reaction, and examples include, for example, aromatic solvents such as toluene, monochlorobenzene and o-dichlorobenzene.

<Second Step>

The salicylanilide derivative having pyridyl group (12) can be prepared by reacting the salicylanilide derivative (10) obtained in the first step with the pyridylboronic acid derivative (11). This reaction is carried out in a solvent, in the presence of a catalytic amount of a transition metal complex, in the presence of or absence of a base, at a reaction temperature of from 0° C. to the boiling point of the solvent.

As the transition metal complex, examples include, for example, [1,1'-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Third Step>

The final target compound (13) can be prepared by the reduction of the salicylanilide derivative having pyridyl group (12) obtained in the second step. This reaction is carried out in a solvent under hydrogen atmosphere (from normal pressure to 50 atm), in the presence of a noble metal catalyst, at a reaction temperature of from 0° C. to the boiling point of the solvent.

As the noble catalyst, examples include, for example, platinum oxide and the like.

As the solvent, any solvent can be used as long as it does not inhibit the reaction, and examples include, for example, alcohols such as methanol and ethanol and the like.

As the aforementioned nitrobenzene derivative (3), the compound represented by the following formula (V):

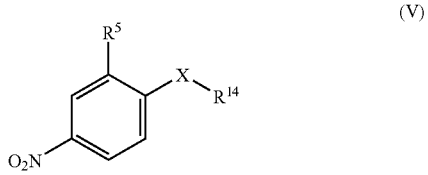

(V)

wherein $R^5$ represents a halogen atom, cyano group, a $C_{1-4}$ alkyl group, a halogenated $C_{1-4}$ alkyl group or a $C_{1-4}$ alkoxy group, $R^{14}$ represents cyclohexyl group; a $NR^{15}R^{16}$ substituted cyclohexyl group; a 5 to 7-membered completely saturated heterocyclic group selected from the group consisting of a pyrrolidinyl group, a piperidinyl group, a piperazinyl group, a morpholinyl group, a thiomorpholinyl group, an azepanyl group and a 1,4-diazepanyl group, and those heterocyclic groups wherein the hydrogen atom of —NH— constituting the heterocyclic ring is substituted with a protecting group; an aforementioned 5 to 7-membered completely saturated heterocyclic group substituted with the group selected from the group consisting of a $C_{1-6}$ alkyl group, a $C_{7-12}$ aralkyl group, a $C_{2-7}$ alkanoyl group, a $C_{2-7}$ alkoxycarbonyl group, carbamoyl group, $NR^{17}R^{18}$, oxo group, a pyrrolidinyl group, a $NR^{15}R^{16}$ substituted $C_{1-6}$ alkyl group and a piperidinyl substituted $C_{2-7}$ alkanoyl group; or 1,4-dioxa-8-azaspiro[4,5]decan-8-yl group, X represents a single bond, oxygen atom, $NR^7$ or —O—CH$_2$—, $R^7$ represents hydrogen atom, $R^{15}$, $R^{16}$ and $R^{17}$ independently represent hydrogen atom or a protecting group, $R^{18}$ represents hydrogen atom, a protecting group or a $C_{1-6}$ alkyl group is preferably used.

Furthermore, as the aforementioned aniline derivative (4), the compound represented by the following formula (III):

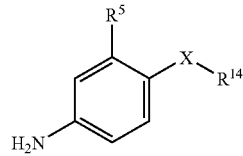

(III)

wherein $R^5$ represents a halogen atom, cyano group, a $C_{1-4}$ alkyl group, a halogenated $C_{1-4}$ alkyl group or a $C_{1-4}$ alkoxy group, $R^{14}$ represents cyclohexyl group; a $NR^{15}R^{16}$ substituted cyclohexyl group; a 5 to 7-membered completely saturated heterocyclic group selected from the group consisting of a pyrrolidinyl group, a piperidinyl group, a piperazinyl group, a morpholinyl group, a thiomorpholinyl group, an azepanyl group and a 1,4-diazepanyl group, and those heterocyclic groups wherein the hydrogen atom of —NH— constituting the heterocyclic ring is substituted with a protecting group; an aforementioned 5 to 7-membered completely saturated heterocyclic group substituted with the group selected from the group consisting of a $C_{1-6}$ alkyl group, a $C_{7-12}$ aralkyl group, a $C_{2-7}$ alkanoyl group, a $C_{2-7}$ alkoxycarbonyl group, carbamoyl group, $NR^{17}R^{18}$, oxo group, a pyrrolidinyl group, a $NR^{15}R^{16}$ substituted $C_{1-6}$ alkyl group and a piperidinyl substituted $C_{2-7}$ alkanoyl group; or 1,4-dioxa-8-azaspiro[4,5]decan-8-yl group, X represents a single bond, oxygen atom, $NR^7$ or —O—CH$_2$—, $R^7$ represents hydrogen atom, $R^{15}$, $R^{16}$ and $R^{17}$ independently represent hydrogen atom or a protecting group, $R^{18}$ represents hydrogen atom, a protecting group or a $C_{1-6}$ alkyl group is preferably used.

As the aforementioned amide derivative (6), the compound represented by the following formula (IV):

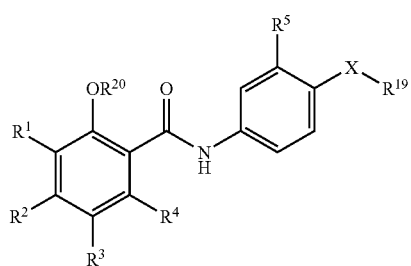

(IV)

wherein $R^1$ and $R^2$ independently represent hydrogen atom or a halogen atom, $R^3$ represents hydrogen atom, a halogen atom, cyano group, nitro group, a $C_{1-4}$ alkyl group or a halogenated $C_{1-4}$ alkyl group, $R^4$ represents hydrogen atom, $R^5$ represents a halogen atom, cyano group, a $C_{1-4}$ alkyl group, a halogenated $C_{1-4}$ alkyl group or a $C_{1-4}$ alkoxy group, $R^{19}$ represents cyclohexyl group; a $NR^{15}R^{16}$ substituted cyclohexyl group; a 5 to 7-membered completely saturated heterocyclic group selected from the group consisting of a pyrrolidinyl group, a piperidinyl group, a piperazinyl group, a morpholinyl group, a thiomorpholinyl group, an azepanyl group and a 1,4-diazepanyl group, and those heterocyclic groups wherein the hydrogen atom of —NH— constituting the heterocyclic ring is substituted with a protecting group; an aforementioned 5 to 7-membered completely saturated heterocyclic group substituted with the group selected from the group consisting of a $C_{1-6}$ alkyl group, a $C_{7-12}$ aralkyl group, a $C_{2-7}$ alkanoyl group, a $C_{2-7}$ alkoxycarbonyl group, carbamoyl group, $NR^{17}R^{18}$, oxo group, a pyrrolidinyl group, a $NR^{15}R^{16}$ substituted $C_{1-6}$ alkyl group and a piperidinyl substituted $C_{2-7}$ alkanoyl group; or 1,4-dioxa-8-azaspiro[4,5]decan-8-yl group, X represents a single bond, oxygen atom, $NR^7$ or —O—CH$_2$—, $R^7$ represents hydrogen atom, $R^{15}$, $R^{16}$ and $R^{17}$ independently represent hydrogen atom or a protecting group, $R^{18}$ represents hydrogen atom, a protecting group or a $C_{1-6}$ alkyl group, $R^{20}$ represents a protecting group is preferably used.

When $R^{14}$ or $R^{19}$ is a pyrrolidinyl group, a piperidinyl group, a piperazinyl group, a morpholinyl group, a thiomorpholinyl group, an azepanyl group or a 1,4-diazepanyl group, said group is preferably any one of the following groups.

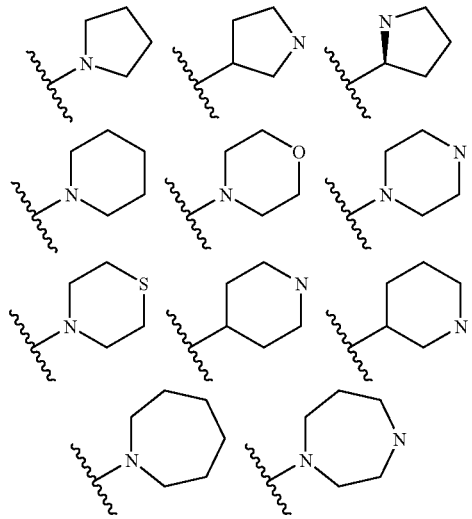

When $R^{14}$ or $R^{19}$ is a $NR^{15}R^{16}$ substituted cyclohexyl group, said group is preferably the following group.

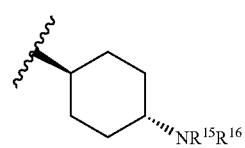

Where $R^{14}$ or $R^{15}$ is a 5 to 7-membered completely saturated heterocyclic group substituted with the group selected from the group consisting of a $C_{1-6}$ alkyl group, a $C_{7-12}$ aralkyl group, a $C_{2-7}$ alkanoyl group, a $C_{2-7}$ alkoxycarbonyl group, carbamoyl group, $NR^{17}R^{18}$, oxo group, a pyrrolidinyl group, a $NR^{15}R^{16}$ substituted $C_{1-6}$ alkyl group and a piperidinyl substituted $C_{2-7}$ alkanoyl group, said group is preferably any one of the following groups.

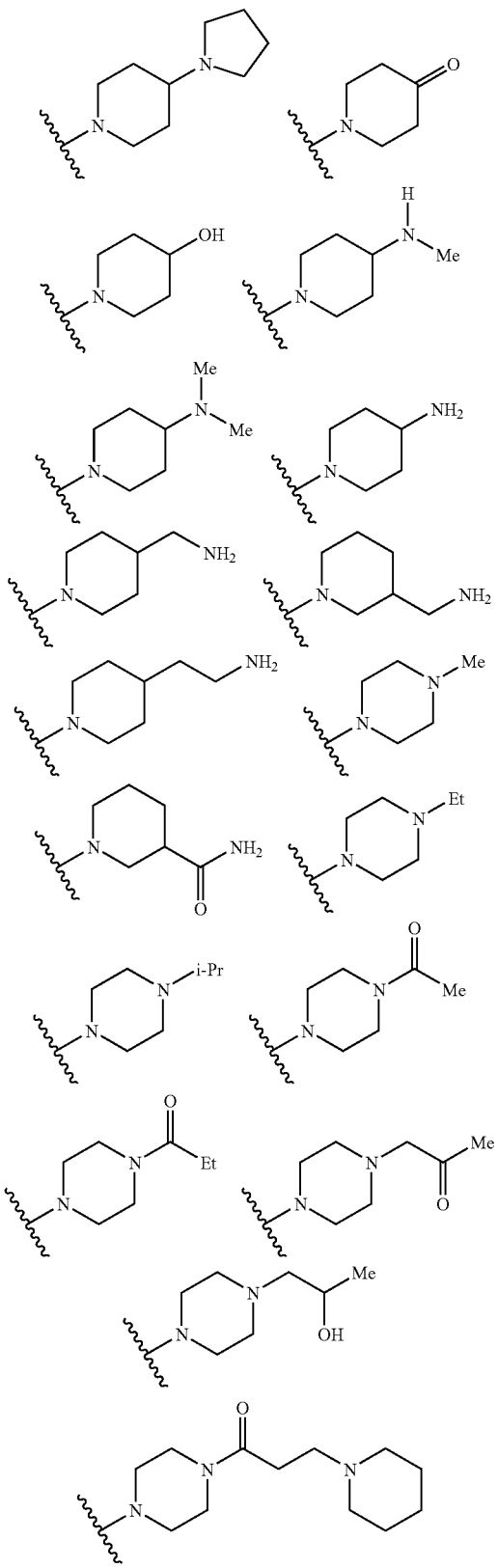

-continued

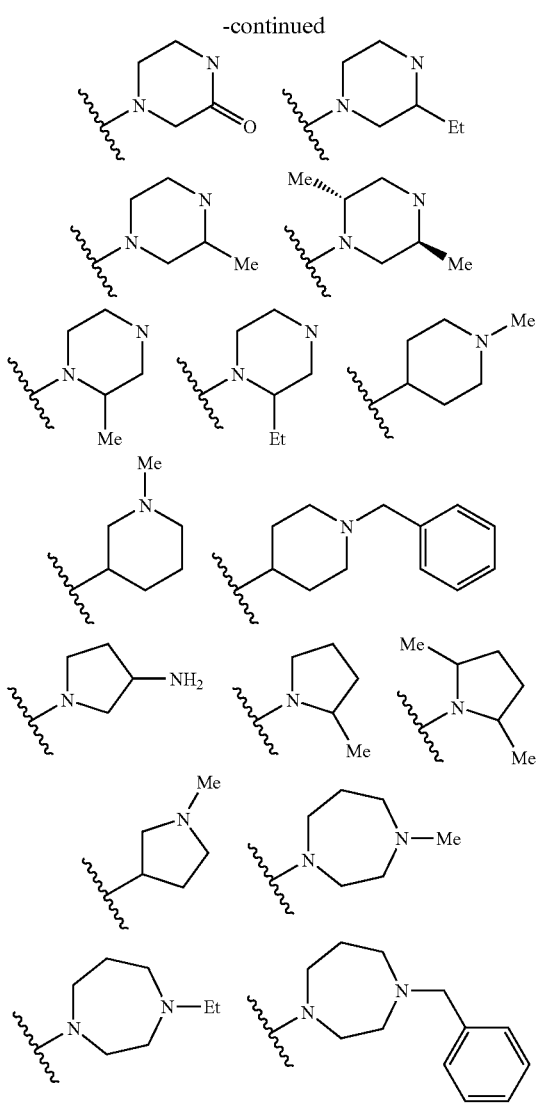

The aforementioned compounds represented by the aforementioned (1) to (6) and (8) to (12) are useful for the manufacture of the compounds having inhibitory activity against activation of STAT6 and/or NF-κB.

In the examples of the specification, preparation methods of typical compounds included in the general formula (I) are explained in details. Therefore, those skilled in the art can prepare any compound falling within the general formula (I) by referring to the explanations of the aforementioned general preparation methods and those of specific preparation methods of the examples, selecting appropriate reaction raw materials, reagents, and reaction conditions, and by adding appropriate modification and alteration of these methods, if necessary.

Some of the compounds represented by the aforementioned (2), (3) and (4) that are synthetic intermediates of the compounds represented by the general formula (I) are publicly known compounds, and their preparation methods are disclosed, for example, in the following documents.

(i) Japanese Patent Unexamined Publication (KOKAI) No. (Hei) 11-158164, pp. 17, paragraph 0058-pp. 21, paragraph 0071

(ii) EP 1130016 A1

(iii) Chem. Pharm. Bull., vol. 49, No. 4, pp. 353-360 (2001).

(iv) J. Med. Chem., vol. 39, No. 3, pp. 673-679 (1996).

In the compounds represented by the above (2), (3) and (4), the details of the preparation methods of novel compounds are disclosed in the following Reference Examples.

The compounds represented by the aforementioned formula (I) have inhibitory activity against the activation of STAT6 and/or NF-κB, and are useful as active ingredients of the medicament for prophylactic and/or therapeutic treatment of diseases caused by the activation of STAT6 and/or NF-κB.

Examples of diseases caused by the activation of STAT6 and/or NF-κB include, for example, respiratory diseases, dermatologic diseases, connective tissue diseases, musculoskeletal diseases, gastrointestinal diseases, hepatic diseases, cardiovascular diseases, urologic diseases, neurologic diseases, cancers, tumors, hematologic diseases, metabolic diseases, allergic diseases, autoimmune diseases, and acquired immunodeficiency syndrome (AIDS).

Examples of respiratory diseases include, for example, asthma, chronic obstructive pulmonary disease (COPD), bronchitis, and pneumonia.

Examples of dermatologic diseases include, for example, atopic dermatitis, pruritus, psoriasis, and incontinentia pigmenti.

Examples of connective tissue diseases include, for example, rheumatoid arthritis, systematic lupus erythematosus, osteoarthritis, and arthritis.

Examples of musculoskeletal diseases include for example, muscular dystrophy.

Examples of gastrointestinal diseases include, for example, Crohn's disease and inflammatory bowel diseases such as ulcerative colitis.

Examples of hepatic diseases include, for example, hepatic cirrhosis, and hepatitis.

Examples of cardiovascular diseases include, for example, arteriosclerosis, restenosis after percultaneous transluminal coronary angioplasty (PTCA), myocardial infarction, and cardiac hypertrophy.

Examples of urologic diseases include, for example, nephritis and interstitial cystitis.

Examples of neurologic diseases include, for example, Alzheimer's disease, Parkinson's disease, epilepsy, and multiple sclerosis.

Examples of cancers include, for example, solid cancers such as skin cancer, lung cancer, liver cancer, and kidney cancer; and cancer cachexia.

Examples of tumors include, for example, melanoma, and malignant lymphoma.

Examples of hematologic diseases include, for example, leukemia.

Examples of metabolic diseases include, for example, diabetes, and osteoporosis.

Examples of allergic diseases include, for example, allergic rhinitis, and pollinosis.

As the active ingredient of the medicament on the present invention, one or more kinds of substances selected from the group consisting of the compound represented by the general formula (I) and a pharmacologically acceptable salt thereof, and a hydrate thereof and a solvate thereof may be used. The aforementioned substance, per se, may be administered as the medicament of the present invention, however, preferably, the medicament of the present invention is provided in the form of a pharmaceutical composition comprising the aforementioned substance, which is an active ingredient, together with one or more pharmacologically acceptable pharmaceutical additives. In the aforementioned pharmaceutical compositions, a ratio of the active ingredient to the pharmaceutical additives is approximately 1 weight % to 90 weight %.

The pharmaceutical compositions of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration, or subcutaneous administration, drops, suppositories, percutaneous absorbent, transmucosal absorption preparations, nasal drops, ear drops, instillation, and inhalants. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the active ingredient, and further binders, disintegrator, lubricant, colorant, corrigent are added, if necessary, preparations in the forms of tablets, coating tablets, granules, powders, capsules and the like may be manufactured by ordinary procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used which are approved to be added to ordinary pharmaceuticals. As the corrigent, cocoa powder, menthol, aromatic acid, peppermint oil, d-borneol, cinnamon powder and the like can be used. These tables and granules may be applied with sugarcoating, gelatin coating, or an appropriate coating, if necessary. Preservatives, antioxidant and the like may be added, if required.

For liquid preparations for oral administration such as emulsions, syrups, suspensions, and solutions, ordinary used inactive diluents, for example, water or vegetable oil may be used. For these preparations, besides inactive diluents, adjuvants such as wetting agents, suspending aids, sweating agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the composition are prepared in the form of injections, carriers such as, for example, diluents including water, ethanol, macrogol, propyleneglycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt, glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream gel, or paste and the like may be applied by a common method to an ordinary substrate. As the substrate, fabric made of cotton, span rayon, and synthetic fibersor or nonwoven fabric, and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. The dose may preferably be increased or decreased appropriately depending on the age, pathological conditions, and symptoms of a patient. The above dose may be administered once a day or 2 to 3 times a day as divided portions with suitable intervals, or intermittent administration for every several days may be acceptable. When the medicament is used as an injection, the dose may be 0.001 to 100 mg per day for an adult as the weight of the compound of the present invention.

EXAMPLES

The present invention will be explained more specifically with reference to the following examples. However the scope of the present invention is not limited to the following examples.

The abbreviations used in the following examples have the following meanings.

Boc: tert-butoxycarbonyl group, MEMO: 2-methoxyethoxymethoxy group.

Reference Example 1

Preparation of benzylidene(piperidin-4-ylmethyl)amine

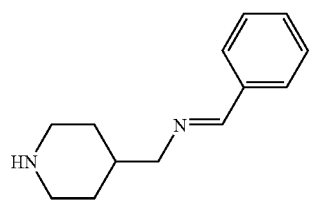

This compound was obtained in the same manner as the method described in the following document.

Synth. Commun., vol. 22, No. 16, pp. 2357-2360 (1992).

Reference Example 2

Preparation of 4-[4-nitro-2-(trifluoromethyl)phenyl]morpholine

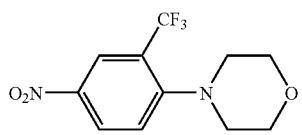

A mixture of 1-fluoro-4-nitro-2-(trifluoromethyl)benzene (1 g, 4.782 mmol), morpholine (0.46 ml, 5.260 mmol), diisopropylethylamine (1.25 ml, 7.173 mmol) and acetonitrile (10 ml) was refluxed for 8 hours. Water was added to the residue obtained by evaporation of the solvent under reduced pressure. The precipitated crystal was collected by filtration to give the title compound (1.2 g, 91%) as a yellow crystal.

$^1$H-NMR (CDCl$_3$) δ: 3.13 (4H, t, J=4.5 Hz), 3.87 (4H, t, J=4.5 Hz), 7.31 (1H, d, J=9 Hz), 8.36 (1H, dd, J=9.3 Hz), 8.53 (1H, d, J=3 Hz).

The compounds described in Reference Examples 3 to 39 were obtained in the same manner as the method of Reference Example 2 by reacting the appropriate 4-halogenated nitrobenzene derivative with the cyclic compound.

TABLE 2

| Reference Example | Structure | NMR |
|---|---|---|
| 3 | [structure: O$_2$N-phenyl(F)-piperidine] | Yield: 99%<br>$^1$H-NMR (CDCl$_3$) δ: 1.60-1.79 (6H, m), 3.22-3.30 (4H, m), 6.69 (1H, t, J = 9.0 Hz), 7.88 (1H, dd, J = 13.5, 2.4 Hz), 7.96 (1H, ddd, J = 9.0, 2.4, 0.9 Hz). |
| 4 | [structure: O$_2$N-phenyl(CF$_3$)-piperazine-NMe] | Yield: 95%<br>$^1$H-NMR (CDCl$_3$) δ: 2.38 (3H, s), 2.55-2.65 (4H, m), 3.14-3.22 (4H, m), 7.29 (1H, d, J = 9.0 Hz), 8.33 (1H, dd, J = 9.0, 2.4 Hz), 8.51 (1H, d, J = 2.4 Hz). |
| 5 | [structure: O$_2$N-phenyl(Cl)-piperazine-NMe] | Yield: 93%<br>$^1$H-NMR (CDCl$_3$) δ: 2.38 (3H, s), 2.57-2.67 (4H, m), 3.20-3.30 (4H, m), 7.05 (1H, d, J = 9.0 Hz), 8.09 (1H, dd, J = 9.0, 2.4 Hz), 8.25 (1H, d, J = 2.4 Hz). |
| 6 | [structure: O$_2$N-phenyl(Me)-piperazine-NMe] | Yield: 97%<br>$^1$H-NMR (CDCl$_3$) δ: 2.36 (3H, s), 2.38 (3H, s), 2.56-2.65 (4H, m), 3.02-3.10 (4H, m), 6.98-7.03 (1H, m), 8.00-8.07 (2H, m). |
| 7 | [structure: O$_2$N-phenyl(F)-piperazine-N-i-Pr] | Yield: 99%<br>$^1$H-NMR (CDCl$_3$) δ: 1.09 (6H, d, J = 6.6 Hz), 2.66-2.73 (4H, m), 2.75 (1H, sep, J = 6.6 Hz), 2.99-3.05 (4H, m), 6.91 (1H, t, J = 8.7 Hz), 7.79-8.12 (2H, m). |
| 8 | [structure: O$_2$N-phenyl(F)-piperazine-NEt] | Yield: 94%<br>$^1$H-NMR (CDCl$_3$) δ: 1.13 (3H, t, J = 7.0 Hz), 2.49 (2H, q, J = 7.0 Hz), 2.63 (4H, t, J = 5.0 Hz), 3.34 (4H, t, J = 5.0 Hz), 6.92 (1H, t, J = 9.0 Hz), 7.90 (1H, dd, J = 13.0, 2.5 Hz), 7.84 (1H, ddd, J = 9.0, 2.5, 1.0 Hz). |
| 9 | [structure: O$_2$N-phenyl(Me)-piperazine-NEt] | Yield: 85%<br>$^1$H-NMR (CDCl$_3$) δ: 1.14 (3H, t, J = 7.0 Hz), 2.36 (3H, s), 2.50 (2H, q, J = 7.0 Hz), 2.64 (4H, brs), 3.07 (4H, t, J = 5.0 Hz), 7.00 (1H, dd, J = 7.0, 2.5 Hz), 8.04 (2H, m). |
| 10 | [structure: O$_2$N-phenyl(F)-piperazine-N-C(O)Me] | Yield: 92%<br>$^1$H-NMR (CDCl$_3$) δ: 2.16 (3H, t, J = 5.0 Hz), 3.25 (2H, t, J = 5.0 Hz), 3.31 (2H, t, J = 5.0 Hz), 3.66 (2H, t, J = 5.0 Hz), 3.81 (2H, t, J = 5.0 Hz), 6.93 (1H, t, J = 9.0 Hz), 7.94 (1H, dd, J = 13.0, 2.5 Hz), 8.01 (1H, dd, J = 9.0, 2.5 Hz). |

TABLE 2-continued

| Reference Example | Structure | NMR |
|---|---|---|
| 11 | (structure: 4-nitro-2-methylphenyl piperazine N-acetyl) | Yield: 88%<br>¹H-NMR (CDCl₃) δ: 2.16 (3H, s), 2.40 (3H, s), 2.98 (2H, t, J = 5.0 Hz), 3.02 (2H, t, J = 5.0 Hz), 3.65 (2H, t, J = 5.0 Hz), 3.80 (2H, t, J = 5.0 Hz), 7.00 (1H, d, J = 8.5 Hz), 8.04-8.08 (2H, m). |
| 12 | (structure: 4-nitro-2-fluorophenyl thiomorpholine) | Yield: 96%<br>¹H-NMR (CDCls) δ: 2.77-2.84 (4H, m), 3.55-3.62 (4H, m), 6.93 (1H, t, J = 8.7 Hz), 7.91 (1H, dd, J = 12.9, 2.7 Hz), 7.98 (1H, ddd, J = 8.7, 2.7, 0.6 Hz). |
| 13 | (structure: 4-nitro-2-fluorophenyl 4-(Boc-amino)piperidine) | Yield: 92%<br>¹H-NMR (CDCl₃) δ: 1.46 (9H, s), 1.50-1.65 (2H, m), 2.01-2.18 (2H, m), 2.92-3.04 (2H, m), 3.58-3.74 (3H, m), 4.49 (1H, brs), 6.92 (1H, t, J = 8.7 Hz), 7.90 (1H, dd, J = 12.9, 2.7 Hz), 7.97 (1H, ddd, J = 8.7, 2.4, 0.9 Hz). |
| 14 | (structure: 4-nitro-2-fluorophenyl N-Boc-piperazine) | Yield: 78%<br>¹H-NMR (CDCl₃) δ: 1.49 (9H, s), 3.20-3.28 (4H, m), 3.57-3.65 (4H, m), 6.92 (1H, t, J = 8.7 Hz), 7.93 (1H, dd, J = 13.2, 3.0 Hz), 7.99 (1H, ddd, J = 9.0, 2.4, 1.2 Hz). |
| 15 | (structure: 4-nitro-2-fluorophenyl N-methyl-homopiperazine) | Yield: 96%<br>¹H-NMR (CDCl₃) δ: 2.05 (2H, q, J = 6.0 Hz), 2.41 (3H, s), 2.62 (2H, t, J = 5.0 Hz), 2.78 (2H, t, J = 4.5 Hz), 3.58 (2H, dt, J = 6.0, 1.5 Hz), 3.63-3.67 (2H, m), 6.73 (1H, t, J = 9.0 Hz), 7.86 (1H, dd, J = 14.0, 3.0 Hz), 7.20 (1H, dd, J = 9.0, 3.0 Hz). |
| 16 | (structure: 4-nitro-2-fluorophenyl piperazin-2-one) | Yield: 65%<br>¹H-NMR (DMSO-d₆) δ: 3.30-3.36 (2H, m), 3.54-3.59 (2H, m), 3.91 (2H, s), 7.16 (1H, t, J = 8.7 Hz), 7.98-8.07 (2H, m), 8.16 (1H, s). |
| 17 | (structure: 4-nitro-2-fluorophenyl 1,4-dioxa-8-azaspiro[4.5]decane) | Yield: 60%<br>¹H-NMR (CDCl₃) δ: 1.88 (4H, t, J = 5.7 Hz), 3.41 (4H, t, J = 5.7 Hz), 4.01 (4H, s), 6.92 (1H, t, J = 8.7 Hz), 7.90 (1H, dd, J = 13.2, 2.7 Hz), 7.95-7.99 (1H, m). |
| 18 | (structure: 4-nitro-2-fluorophenylamino 1-benzylpiperidine) | Yield: 83%<br>¹H-NMR (CDCl₃) δ: 1.53-1.68 (2H, m), 1.99-2.09 (2H, m), 2.14-2.26 (2H, m), 2.82-2.93 (2H, m), 3.36-3.49 (1H, m), 3.55 (2H, s), 4.52-4.64 (1H, m), 6.63 (1H, t, J = 8.4 Hz), 7.28-7.36 (5H, m), 7.88 (1H, dd, J = 12.0, 2.7 Hz), 7.97 (1H, dd, J = 9.0, 2.1 Hz). |
| 19 | (structure: 4-nitro-2-fluorophenyl 3-(Boc-amino)pyrrolidine) | Yield: quantitative<br>¹H-NMR (CDCl₃) δ: 1.46 (9H, s), 1.91-2.03 (1H, m), 2.20-2.33 (1H, m), 3.40-3.49 (1H, m), 3.57-3.78 (2H, m), 3.80-3.89 (1H, m), 4.33 (1H, brs), 4.69 (1H, brs), 6.34 (1H, t, J = 8.7 Hz), 7.88 (1H, dd, J = 14.1, 2.7 Hz), 7.93 (1H, dd, J = 9.0, 2.7 Hz). |
| 20 | (structure: 4-nitro-2-fluorophenyl N-Boc-homopiperazine) | Yield: 49%<br>¹H-NMR (CDCl₃) δ: 1.36-1.43 (9H, m), 1.93-2.00 (2H, m), 3.35-3.47 (2H, m), 3.60-3.72 (6H, m), 6.78 (1H, t, J = 9.0 Hz), 7.87-7.95 (2H, m). |

TABLE 2-continued

| Reference Example | Structure | NMR |
|---|---|---|
| 21 | 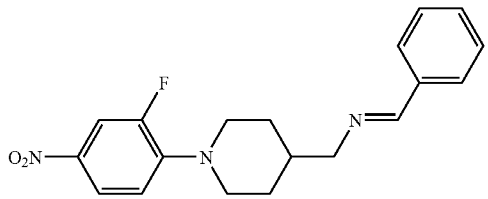 | Yield: 97%<br>$^1$H-NMR (CDCl$_3$) δ: 1.42-1.58 (2H, m), 1.85-2.06 (3H, m), 2.84-2.97 (2H, m), 3.54-3.59 (2H, m), 3.70-3.79 (2H, m), 6.91 (1H, t, J = 8.7 Hz), 7.39-7.47 (3H, m), 7.71-7.78 (2H, m), 7.89 (1H, dd, J = 13.2, 2.4 Hz), 7.96 (1H, dd, J = 9.0, 2.7 Hz), 8.28 (1H, s). |
| 22 | 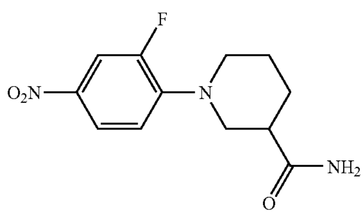 | Yield: 74%<br>$^1$H-NMR (CDCl$_3$) δ: 1.67-2.07 (4H, m), 2.56-2.67 (1H, m), 2.97-3.07 (1H, m), 3.18-3.28 (1H, m), 3.41-3.51 (1H, m), 3.56-3.64 (1H, m), 5.47 (1H, brs), 5.91 (1H, brs), 6.99 (1H, t, J = 8.7 Hz), 7.92 (1H, dd, J = 12.9, 2.4 Hz), 7.99 (1H, ddd, J = 9.0, 2.7, 0.9 Hz). |
| 23 | 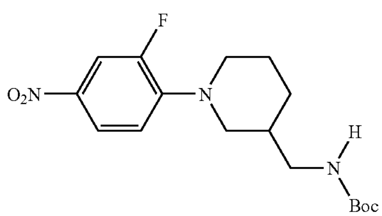 | Yield: 97%<br>$^1$H-NMR (CDCl$_3$) δ: 1.17-1.31 (1H, m), 1.45 (9H, s), 1.65-1.77 (1H, m), 1.77-1.99 (3H, m), 2.66-2.75 (1H, m), 2.84-2.95 (1H, m), 3.15 (2H, t, J = 6.6 Hz), 3.51-3.62 (2H, m), 4.63 (1H, brs), 6.89 (1H, t, J = 9.3 Hz), 7.88 (1H, dd, J = 13.2, 2.4 Hz), 7.95 (1H, ddd, J = 9.0, 2.7, 1.2 Hz). |
| 24 | 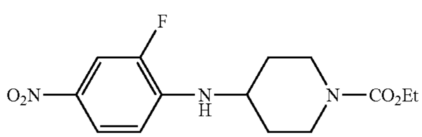 | Yield: 29%<br>$^1$H-NMR (CDCl$_3$) δ: 1.19 (3H, t, J = 6.9 Hz), 1.36-1.51 (2H, m), 1.81-1.93 (2H, m), 2.85-3.00 (2H, m), 3.64-3.78 (1H, m), 3.94-4.06 (2H, m), 4.04 (2H, q, J = 6.9 Hz), 6.88 (1H, d, J = 6.3 Hz), 6.96 (1H, t, J = 9.0 Hz), 7.88-7.98 (2H, m). |
| 25 | 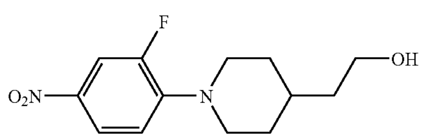 | Yield: 95%<br>$^1$H-NMR (CDCl$_3$) δ: 1.23 (1H, t, J = 5.4 Hz), 1.35-1.50 (2H, m), 1.59 (2H, q, J = 6.6 Hz), 1.62-1.77 (1H, m), 1.80-1.89 (2H, m), 2.82-2.93 (2H, m), 3.66-3.79 (4H, m), 6.90 (1H, t, J = 8.7 Hz), 7.89 (1H, dd, J = 12.9, 2.4 Hz), 7.96 (1H, dd, J = 9.0, 2.7 Hz). |
| 26 | 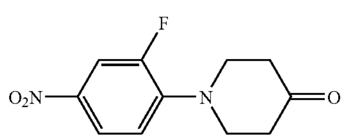 | Yield: 86%<br>$^1$H-NMR (CDCl$_3$) δ: 2.66 (4H, t, J = 6.0 Hz), 3.66 (4H, t, J = 6.0 Hz), 6.99 (1H, t, J = 9.0 Hz), 7.93-8.03 (2H, m). |
| 27 | 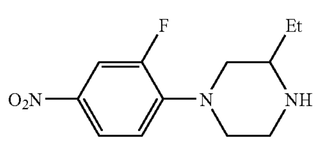 | Yield: 21%<br>$^1$H-NMR (CDCl$_3$) δ: 1.01 (3H, t, J = 7.5 Hz), 1.52 (2H, quint, J = 7.5 Hz), 2.63-2.71 (1H, m), 2.85-3.20 (5H, m), 3.58-3.63 (2H, m), 6.92 (1H, t, J = 8.8 Hz), 7.88-8.00 (2H, m). |
| 28 | 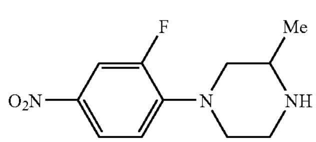 | Yield: 37%<br>$^1$H-NMR (CDCl$_3$) δ: 1.13 (3H, d, J = 6.4 Hz), 2.52-2.59 (1H, m), 2.90-3.10 (4H, m), 3.52-3.59 (2H, m), 6.90 (1H, J = 8.8 Hz), 7.87-8.00 (2H, m). |
| 29 | 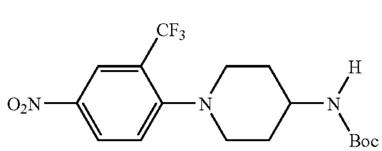 | Yield: 70%<br>$^1$H-NMR (CDCl$_3$) δ: 1.46 (9H, s), 1.59-1.66 (2H, m), 2.05-2.09 (2H, m), 2.90-2.98 (2H, m), 3.31-3.35 (2H, m), 3.64 (1H, brs), 4.51 (1H, brs), 7.26-7.28 (2H, m), 8.29-8.32 (1H, m). |

TABLE 2-continued

| Reference Example | Structure | NMR |
|---|---|---|
| 30 | 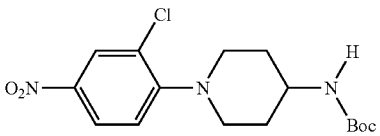 | Yield: 90%<br>$^1$H-NMR(CDCl$_3$) δ: 1.46 (9H, s), 1.53-1.70 (2H, m), 2.07-2.11 (2H, m), 2.85-2.93 (2H, m), 3.51-3.55 (2H, m), 3.66 (1H, brs), 4.52 (1H, brs), 7.04 (1H, d, J = 9.0 Hz), 8.08 (1H, dd, J = 9.0, 2.7 Hz), 8.24 (1H, d, J = 2.7 Hz). |
| 31 | 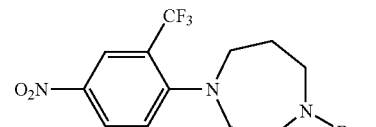 | Yield: 54%<br>$^1$H-NMR (CDCl$_3$) δ: 1.48 (9H, m), 1.94-2.01 (2H, m), 3.30-3.34 (4H, m), 3.51-3.63 (4H, m), 7.27-7.31 (1H, m), 8.29 (1H, dd, J = 9.0, 2.5 Hz), 8.51 (1H, d, J = 2.5 Hz). |
| 32 | 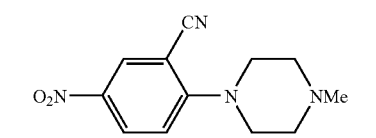 | Yield: quantitative<br>$^1$H-NMR (GDCl$_3$) δ: 2.38 (3H, s), 2.64 (4H, t, J = 4.8 Hz), 3.55 (4H, t, J = 4.8 Hz), 6.99 (1H, d, J = 9.0 Hz), 8.27 (1H, dd, J = 9.0, 2.7 Hz), 8.43 (1H, d, J = 2.7 Hz). |
| 33 | 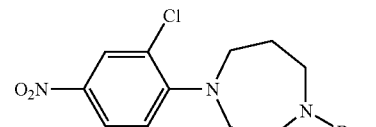 | Yield: 99%<br>$^1$H-NMR (CDCl$_3$) δ: 1.47 (9H, s), 2.02-2.08 (2H, m), 3.42-3.48 (4H, m), 3.51-3.69 (4H, m), 7.05 (1H, d, J = 9.1 Hz), 8.04 (1H, dd, J = 9.1, 2.6 Hz), 8.24 (1H, d, J = 2.6 Hz). |
| 34 | 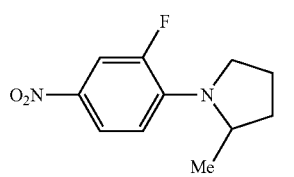 | Yield: 93%<br>F$^1$H-NMR (CDCl$_3$) δ: 1.21 (3H, d, J = 6.3 Hz), 1.66-1.80 (1H, m), 1.90-2.22 (3H, m), 3.46-3.54 (1H, m), 3.61-3.78 (1H, m), 4.18-4.34 (1H, m), 6.57 (1H, t, J = 9.3 Hz), 7.81-7.98 (2H, m). |
| 35 | 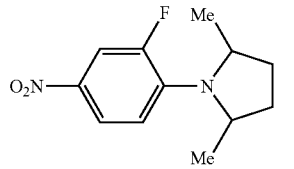 | This compound was obtained as a diastereomeric mixture.<br>Yield: 50%<br>$^1$H-NMR(CDCl$_3$) δ (major isomer): 1.33 (6H, d, J = 6.3 Hz), 1.71-1.90 (2H, m), 2.01-2.18 (2H, m), 4.00-4.22 (2H, m), 6.60 (1H, t, J = 9.0 Hz), 7.82-7.97 (2H, m).<br>δ (minor isomer): 1.12 (6H, d, J = 6.6 Hz), 1.61-1.73 (2H, m), 2.16-2.31 (2H, m), 4.24-4.41 (2H, m),<br>6.64 (1H, t, J = 9.0 Hz), 7.82-7.97 (2H, m). |
| 36 | 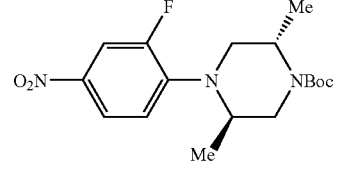 | Yield: 46%<br>$^1$H-NMR (CDCl$_3$) δ: 1.15 (3H, d, J = 6.6 Hz), 1.28 (3H, d, J = 6.8 Hz), 1.49 (9H, s), 3.14-3.18 (1H, m), 3.44-3.57 (2H, m), 3.74-3.79 (1H, m), 4.01 (1H, brs), 4.43 (1H, brs), 6.84 (1H, t, J = 8.8 Hz), 7.87-7.99 (2H, m). |
| 37 | 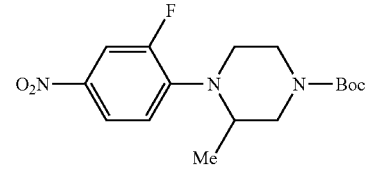 | Yield: 33%<br>$^1$H-NMR (CDCl$_3$) δ: 1.10 (3H, d, J = 6.6 Hz), 1.49 (9H, s), 3.14-3.18 (2H, m), 3.33-3.41 (2H, m), 3.78-3.83 (1H, m), 3.96-3.99 (1H, m), 4.13 (1H, brs), 6.89 (1H, t, J = 8.8 Hz), 7.89-8.00 (2H, m). |

TABLE 2-continued

| Reference Example | Structure | NMR |
|---|---|---|
| 38 | O₂N—(2-F-phenyl)—N(Et)-piperazine-N—Boc | Yield: 27%<br>¹H-NMR (CDCl₃) δ: 0.89 (3H, t, J = 7.4 Hz), 1.49 (9H, s), 1.62-1.72 (2H, m), 3.04-3.42 (4H, m), 3.69 (1H, brs), 4.03-4.08 (1H, m), 4.19 (1H, brs), 6.85 (1H, t, J = 8.8 Hz), 7.88-7.99 (2H, m). |

Reference Example 39

Preparation of 4-(2-fluoro-4-nitrophenoxy)-1-methylpiperidine

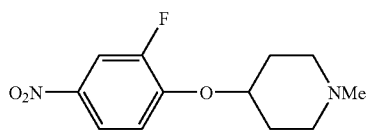

A solution of 4-hydroxy-1-methylpiperidine (0.30 g, 2.65 mmol) in anhydrous tetrahydrofuran (6 ml) was added dropwise to a suspension of 60% sodium hydride (0.054 g, 2.27 mmol) in anhydrous tetrahydrofuran (6 ml) under ice cooling, and the mixture was stirred at room temperature for 1 hour. 3,4-Difluoronitrobenzene (0.30 g, 1.89 mmol) was added to the reaction mixture under ice cooling, and the mixture was refluxed for 3 hours. Ice water was added to the reaction mixture and the mixture was extracted with ethyl acetate. The ethyl acetate layer was washed with saturated brine and dried over anhydrous sodium sulfate. The solvent was evaporated under reduced pressure to give the title compound (0.18 g, 38%) as a yellow crystal.

¹H-NMR (CDCl₃) δ: 1.87-1.98 (2H, m), 2.20-2.10 (2H, m), 2.32 (3H, s), 2.28-2.37 (2H, m), 2.65-2.73 (2H, m), 4.47-4.54 (1H, m), 7.03 (1H, t, J=9.0 Hz), 7.98-8.05 (2H, m).

The compounds described in Reference Examples 40 to 49 were obtained in the same manner as the method of Reference Example 39 by reacting the appropriate 4-halogenated nitrobenzene derivative with the cyclic compound.

TABLE 3

| Reference Example | Structure | NMR |
|---|---|---|
| 40 | O₂N—(2-Me-phenyl)—O-piperidine-NMe | Yield: 27%<br>¹H-NMR (CD₃OD) δ: 1.83-1.93 (2H, m), 2.03-2.13 (2H, m), 2.28 (3H, s), 2.32 (3H, s), 2.47 (2H, brs), 2.69 (2H, brs), 4.63-4.70 (1H, m), 7.09 (1H, d, J = 8.5 Hz), 8.07 (1H, s), 8.08 (1H, dd, J = 9.0, 3.0 Hz). |
| 41 | O₂N—(2-F-phenyl)—O-piperidine-N—Boc | Yield: 82%<br>¹H-NMR (CDCl₃) δ: 1.47 (9H, s), 1.83-1.94 (2H, m), 1.91-2.03 (2H, m), 3.35-3.45 (2H, m), 3.66-3.75 (2H, m), 4.63-4.70 (1H, m), 7.02-7.08 (1H, m), 7.96-8.08 (2H, m). |
| 42 | O₂N—(2-F-phenyl)—O-(3-methylpiperidine)-NMe | Yield: 81%<br>¹H-NMR (CDCl₃) δ: 1.50-1.90 (3H, m), 2.06-2.15 (2H, m) 2.22-2.28 (1H, m), 2.33 (3H, s), 2.64-2.70 (1H, m), 2.96-3.01 (1H, m), 4.49-4.54 (1H, m), 7.09 (1H, t, J = 8.7 Hz), 7.96-8.01 (2H, m). |
| 43 | O₂N—(2-F-phenyl)—O-pyrrolidine-N—Me | Yield: quantitative<br>¹H-NMR (CDCl₃) δ: 2.01-2.11 (1H, m), 2.33-2.45 (4H, m), 2.49-2.57 (1H, m), 2.80-2.97 (3H, m), 4.93-4.99 (1H, m), 6.94 (1H, t, J = 8.4 Hz), 7.96-8.05 (2H, m). |

TABLE 3-continued

| Reference Example | Structure | NMR |
|---|---|---|
| 44 | 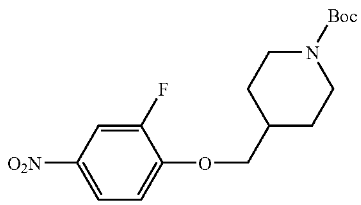 | Yield: 91%<br>$^1$H-NMR (CDCl$_3$) δ: 1.23-1.37 (2H, m), 1.47 (9H, s), 1.83-1.88 (2H, m), 2.01-2.12 (1H, m), 2.73-2.81 (2H, m), 3.97 (2H, d, J = 6.3 Hz), 4.17-4.20 (2H, m), 7.01 (1H, t, J = 9.0 Hz), 7.99 (1H, dd, J = 10.5, 2.7 Hz), 8.02-8.07 (1H, m). |
| 45 | 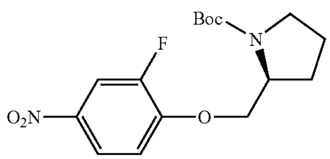 | Yield: 83%<br>$^1$H-NMR (CDCl$_3$) δ: 1.47 (9H, s), 1.82-2.15 (4H, m), 3.24-3.54 (2H, m), 3.95-4.40 (3H, m), 7.02-7.27 (1H, m), 7.93-8.02 (1H, m), 8.01-8.08 (1H, m). |
| 46 | 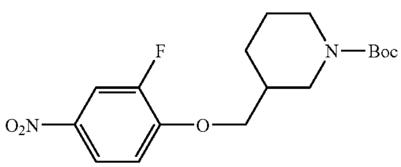 | Yield: 98%<br>$^1$H-NMR (CDCl$_3$) δ: 1.45 (9H, s), 1.48-1.75 (4H, m), 1.89-1.95 (1H, m), 2.05-2.15 (1H, m), 2.83-3.04 (2H, m), 3.82-3.87 (1H, m), 4.00 (2H, d, J = 6.3 Hz), 7.01 (1H, t, J = 9.0 Hz), 7.99 (1H, dd, J = 10.5, 2.7 Hz), 8.02-8.07 (1H, m). |
| 47 | 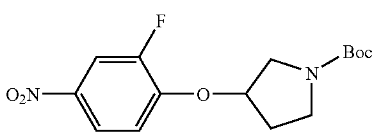 | Yield: 90%<br>$^1$H-NMR (CDCl$_3$) δ: 1.47 (9H, s), 2.24 (2H, brs), 3.47-3.74 (4H, m), 5.05 (1H, brs), 7.00 (1H, t, J = 9.0 Hz), 7.98-8.08 (2H, m). |
| 48 | 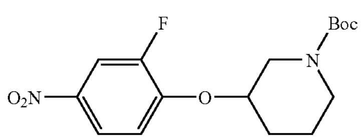 | Yield: 63%<br>$^1$H-NMR (CDCl$_3$) δ: 1.41 (9H, s), 1.54-1.61 (2H, m), 1.88-2.07 (4H, m), 3.48-3.51 (2H, m), 4.40-4.47 (1H, m), 7.06-7.14 (1H, m), 7.98-8.06 (2H, m). |
| 49 | 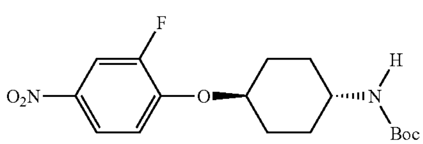 | Yield: 80%<br>$^1$H-NMR (CDCl$_3$) δ: 1.23-1.37 (2H, m), 1.45 (9H, s), 1.59-1.75 (2H, m), 2.13-2.16 (4H, m), 3.54-3.57 (1H, m), 4.33-4.42 (2H, m), 7.02 (1H, t, J = 9.0 Hz), 7.96-8.04 (2H, m). |

Reference Example 50

Preparation of 1-(2-methoxy-4-nitrophenyl)piperidine

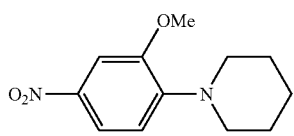

A solution of methanol (0.178 ml, 10.0 mmol) in N,N-dimethylformamide (1 ml) was added dropwise to a suspension of 60% sodium hydride (0.176 g, 4.40 mmol) in N,N-dimethylformamide (5 ml) under ice cooling, and the mixture was stirred at room temperature for 1 hour. 1-(2-Fluoro-4-nitrophenyl)piperidine (compound of Reference Example 3; 0.448 g, 2.00 mmol) was added to the reaction mixture under ice cooling, and the mixture was refluxed for 20 hours. Ice water was added to the reaction mixture and the mixture was extracted with ethyl acetate. The ethyl acetate layer was washed with saturated brine and dried over anhydrous sodium sulfate. The residue obtained by evaporation of the solvent under reduced pressure was purified by column chromatography on silica gel (n-hexane:ethyl acetate=5:1) to give the title compound (0.395 g, 84%) as a yellow solid.

$^1$H-NMR (CDCl$_3$) δ: 1.58-1.68 (2H, m), 1.68-1.80 (4H, m), 3.13-3.20 (4H, m), 3.94 (3H, s), 6.88 (1H, d, J=9.0 Hz), 7.69 (1H, d, J=2.4 Hz), 7.85 (1H, dd, J=9.0, 2.4 Hz).

The compound described in Reference Example 51 was obtained in the same manner as the method of Reference Example 50, except that ethanol was used instead of methanol.

TABLE 4

| Reference Example | Structure | NMR |
|---|---|---|
| 51 | O₂N–C₆H₃(OEt)–N(piperidine) | Yield: 50%<br>¹H-NMR (CDCl₃) δ: 1.51 (3H, t, J = 7.2 Hz), 1.58-1.69 (2H, m), 1.69-1.84 (4H, m), 3.14-3.23 (4H, m), 4.13 (2H, q, J = 7.2 Hz), 6.86 (1H, d, J = 9.0 Hz), 7.67 (1H, d, J = 2.4 Hz), 7.83 (1H, dd, J = 9.0, 2.4 Hz). |

Reference Example 52

Preparation of 1-(2-fluoro-4-nitrophenyl)piperazine

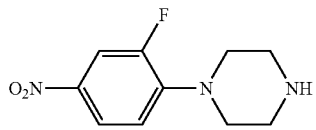

4N Hydrogen chloride/ethyl acetate solution (10.0 ml, 40.0 mmol) was added to a solution of 4-(2-fluoro-4-nitrophenyl)piperazine-1-carboxylic acid tert-butyl ester (compound of Reference Example 14; 2.50 g, 7.68 mmol) in ethyl acetate (10 ml) under ice cooling, and the mixture was stirred at room temperature for 12 hours. The reaction mixture was adjusted to pH=9 by addition of saturated aqueous sodium hydrogencarbonate, and concentrated under reduced pressure. The obtained solid was collected by filtration and washed with water to give the title compound (0.563 g, 37%) as a yellow solid.

¹H-NMR (CD₃OD) δ: 2.98-3.05 (4H, m), 3.26-3.33 (4H, m), 7.12 (1H, t, J=9.0 Hz), 7.94 (1H, dd, J=13.5, 3.0 Hz), 8.02 (1H, ddd, J=9.0, 2.7, 0.9 Hz).

The compounds described in Reference Examples 53 to 55 were obtained in the same manner as the method of Reference Example 52, except that the compound of Reference Examples 46, 44 or 20 was used instead of the compound of Reference Examples 14.

TABLE 5

| Reference Example | Structure | NMR |
|---|---|---|
| 53 | O₂N–C₆H₃(F)–O–CH₂–(3-piperidinyl)NH | Yield: 59%<br>¹H-NMR (CDCl₃) δ: 1.30-1.39 (1H, m), 1.52-1.64 (1H, m), 1.72-1.80 (1H, m), 1.89-1.96 (1H, m), 2.12-2.30 (2H, m), 2.53-2.69 (2H, m), 3.04-3.09 (1H, m), 3.24-3.29 (1H, m), 3.99 (2H, t, J = 6.6 Hz), 7.01 (1H, t, J = 8.4 Hz), 7.89 (1H, dd, J = 10.8, 2.7 Hz), 8.02-8.06 (1H, m). |
| 54 | O₂N–C₆H₃(F)–O–CH₂–(4-piperidinyl)NH | Yield: 20%<br>¹H-NMR (CDCl₃) δ: 1.80-1.90 (2H, m), 2.05-2.24 (4H, m), 2.90-2.98 (2H, m), 3.56-3.60 (2H, m), 4.01 (2H, d, J = 6.6 Hz), 7.01 (1H, t, J = 8.4 Hz), 7.99 (1H, dd, J = 10.8, 2.7 Hz), 8.04-8.80 (1H, m). |
| 55 | O₂N–C₆H₃(F)–N(homopiperazine)NH · HCl | This compound was obtained as a hydrochloride by a direct isolation of the product precipitated during the reaction.<br>Yield: 95%<br>¹H-NMR (DMSO-d6) δ: 2.14-2.19 (2H, m), 3.20-3.46 (4H, m), 3.59 (2H, t, J = 5.7 Hz), 3.76-3.79 (2H, m), 7.09 (1H, t, J = 9.0 Hz), 7.95-8.04 (2H, m), 9.32,9.62 (2H, m). |

Reference Example 56

Preparation of 1-[4-(2-fluoro-4-nitrophenyl)piperazin-1-yl]propan-2-one

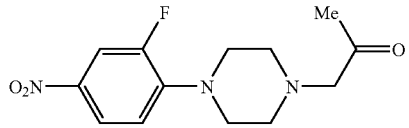

Bromoacetone (0.336 ml, 4.00 mmol) and potassium carbonate (1.38 g, 10.00 mmol) were added to a solution of 1-(2-fluoro-4-nitrophenyl)piperazine (compound of Reference Example 52; 0.390 g, 2.00 mmol) in acetone (10 ml) under ice cooling, and the mixture was stirred at room temperature for 18 hours. The residue obtained by evaporation of the solvent under reduced pressure was washed with water to give the title compound (0.467 g, 83%) as a yellow solid.

$^1$H-NMR (CDCl$_3$) δ: 2.18 (3H, s), 2.67-2.72 (4H, m), 3.30 (2H, s), 3.34-3.39 (4H, m), 6.92 (1H, t, J=9.0 Hz), 7.91 (1H, dd, J=13.2, 3.0 Hz), 7.99 (1H, ddd, J=9.0, 2.7, 1.2 Hz).

Reference Example 57

Preparation of 1-[4-(2-fluoro-4-nitrophenyl)piperazin-1-yl]propan-1-one

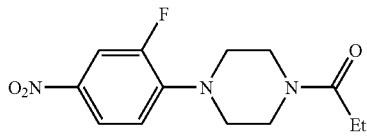

Propionyl chloride (0.620 g, 4.88 mmol), triethylamine (0.747 ml, 5.32 mmol) and 4-dimethylaminopyridine (0.0542 g, 0.444 mmol) were added to a solution of 1-(2-fluoro-4-nitrophenyl)piperazine (compound of Reference Example 52; 1.00 g, 4.44 mmol) in anhydrous tetrahydrofuran (9 ml) under ice cooling, and the mixture was stirred at room temperature for 6 hours. Water was added to the reaction mixture and the mixture was extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=1:1) to give the title compound (0.662 g, 53%) as a yellow solid.

$^1$H-NMR (CDCl$_3$) δ: 1.19 (3H, t, J=7.5 Hz), 2.40 (2H, q, J=7.5 Hz), 3.26 (2H, t, J=5.0 Hz), 3.30 (2H, t, J=5.0 Hz), 3.66 (2H, t, J=5.0 Hz), 3.82 (2H, t, J=5.0 Hz), 6.93 (1H, t, J=9.0 Hz), 7.94 (1H, dd, J=13.0, 2.5 Hz), 8.01 (1H, ddd, J=9.0, 3.0, 1.0 Hz).

The compound described in Reference Example 58 was obtained in the same manner as the method of Reference Example 57, except that 3-chloropropionyl chloride was used instead of propionyl chloride.

Reference Example 59

Preparation of 1-[4-(2-fluoro-4-nitrophenyl)piperazin-1-yl]-3-piperidinopropan-1-one

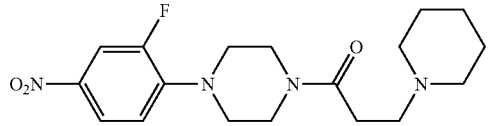

Piperidine (0.081 g, 0.950 mmol) and potassium carbonate (0.380 g, 2.77 mmol) were added to a solution of 3-chlor-1-[4-(2-fluoro-4-nitrophenyl)piperazin-1-yl]propan-1-one (compound of Reference Example 58; 0.250 g, 0.790 mmol) in anhydrous N,N-dimethylformamide (6 ml), and the mixture was stirred at room temperature for 10 hours. Water was added to the reaction mixture and the mixture was extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=1:2) to give the title compound (0.120 g, 41%) as a yellow solid.

$^1$H-NMR (CDCl$_3$) δ: 1.40-1.45 (2H, m), 1.50-1.59 (4H, m), 2.38-2.46 (4H, m), 2.59 (2H, dt, J=7.5, 2.0 Hz), 2.70 (2H, dt, J=7.5, 2.0 Hz), 3.27 (4H, brs), 3.67 (2H, t, J=5.0 Hz), 3.81 (2H, t, J=5.0 Hz), 6.93 (1H, t, J=9.0 Hz), 7.94 (1H, dd, J=12.0, 3.0 Hz), 8.00 (1H, dd, J=9.0, 2.5 Hz).

Reference Example 60

Preparation of 1-(2-fluoro-4-nitrophenyl)piperidine-4-ylmethylamine

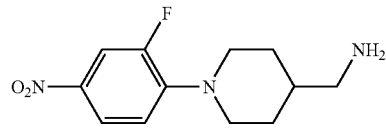

1N aqueous hydrochloric acid (20 ml) was added to benzylidene[1-(2-fluoro-4-nitrophenyl)piperidine-4-ylmethyl]amine (compound of Reference Example 21; 1.15 g, 3.36 mmol), and the mixture was refluxed for 6 hours. The reaction mixture was washed with ethyl acetate and adjusted to pH=12 by addition of 2N aqueous sodium hydroxide. The water layer was saturated with sodium chloride and extracted with chloroform. The organic layer was dried over anhydrous sodium sulfate. The solvent was evaporated under reduced pressure to give the title compound (0.838 g, 98%) as a yellow solid.

$^1$H-NMR (CDCl$_3$) δ: 1.32-1.48 (2H, m), 1.50-1.62 (3H, m), 1.83-1.93 (2H, m), 2.65-2.70 (2H, m), 2.82-2.94 (2H, m), 3.69-3.79 (2H, m), 6.91 (1H, t, J=8.7 Hz), 7.89 (1H, dd, J=13.2, 2.7 Hz), 7.96 (1H, ddd, J=9.0, 3.0, 1.2 Hz).

TABLE 6

| Reference Example | Structure | NMR |
|---|---|---|
| 58 | ![structure] | Yield: 53%<br>$^1$H-NMR (CDCl$_3$) δ: 2.87 (2H, t; J = 7.0 Hz), 3.27 (2H, t, J = 5.0 Hz), 3.32 (2H, t, J = 5.0 Hz), 3.69 (2H, t, J = 5.0 Hz), 3.84 (2H, t, J = 5.0 Hz), 3.87 (2H, t, J = 7.0 Hz), 6.93 (1H, t, J = 9.0 Hz), 7.94 (1H, dd, J = 13.0, 3.0 Hz), 8.01 (1H, ddd, J = 9.0, 3.0, 1.0 Hz). |

Reference Example 61

Preparation of 3-(2-fluoro-4-nitrophenoxymethyl)-1-methylpiperidine

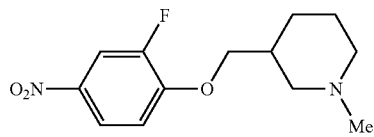

38% aqueous formaldehyde (1.00 ml) and formic acid (1.00 ml) were added to 3-(2-fluoro-4-nitrophenoxymethyl) piperidine (compound of Reference Example 53; 0.300 g, 1.18 mmol), and the mixture was stirred at 90° C. for 1 hour. The reaction mixture was adjusted to pH=8 by addition of saturated aqueous sodium hydrogencarbonate, diluted with water, and extracted with ethyl acetate. The organic layer was dried over anhydrous sodium sulfate. The residue obtained by evaporation of the solvent under reduced pressure was purified by column chromatography on silica gel to give the title compound (0.275 g, 87%) as a yellow solid.

$^1$H-NMR (CDCl$_3$) δ: 1.15-1.26 (1H, m), 1.61-1.78 (3H, m), 1.95-2.05 (2H, m), 2.20-2.30 (4H, m), 2.69-2.77 (1H, m), 2.88-2.95 (1H, m), 4.00-4.03 (2H, m), 7.02 (1H, t, J=8.1 Hz), 7.98 (1H, dd, J=10.5, 2.7 Hz), 8.02-8.06 (1H, m).

The compound described in Reference Example 62 was obtained in the same manner as the method of Reference Example 61, except that the compound of Reference Examples 54 was used instead of the compound of Reference Examples 53.

TABLE 7

| Reference Example | Structure | NMR |
|---|---|---|
| 62 | ![structure] | Yield: 90%<br>$^1$H-NMR (CDCl$_3$) δ : 1.38-1.52 (2H, m), 1.84-2.20 (5H, m), 2.30 (3H, s), 2.89-2.95 (2H, m), 3.97 (2H, d, J = 6.3 Hz), 7.01 (1H, t, J = 8.4 Hz), 7.96-8.06 (2H, m). |

Reference Example 63

Preparation of 1-benzyl-4-(2-fluoro-4-nitrophenyl)-[1,4]diazepane

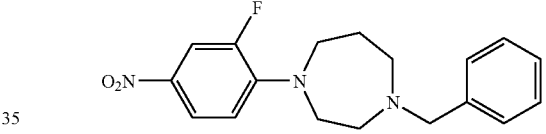

Potassium carbonate (0.526 g, 3.80 mmol) and benzyl bromide (0.155 ml, 0.130 mmol) were added to a solution of 1-(2-fluoro-4-nitrophenyl)-[1,4]diazepane hydrochloride (compound of Reference Example 55; 0.300 g, 1.08 mmol) in anhydrous N,N-dimethylformamide (6 ml), and the mixture was stirred at 80° C. for 6 hours. Water was added to the reaction mixture and the mixture was extracted with ethyl acetate. The organic layer was washed with saturated brine and dried over anhydrous sodium sulfate. The residue obtained by evaporation of the solvent under reduced pressure was purified by column chromatography on silica gel (methanol ethyl acetate=1:1) to give the title compound (0.248 g, 69%) as a brown liquid.

$^1$H-NMR (CDCl$_3$) δ: 1.92-2.01 (2H, m), 2.68 (2H, t, J=4.8 Hz), 2.81 (2H, t, J=4.8 Hz), 3.59-3.65 (6H, m), 6.72 (1H, t, J=9.0 Hz), 7.23-7.37 (5H, m), 7.85-7.94 (2H, m).

The compound described in Reference Example 64 was obtained in the same manner as the method of Reference Example 63, except that ethyl bromide was used instead of benzyl bromide.

TABLE 8

| Reference Example | Structure | NMR |
|---|---|---|
| 64 | ![structure] | Yield: 79%<br>$^1$H-NMR (CDCl$_3$) δ: 1.08 (3H, t, J = 7.2 Hz), 1.89-2.06 (2H, m), 2.55-2.68 (4H, m), 2.82 (2H, t, J = 4.8 Hz), 3.57-3.67 (4H, m), 6.73 (1H, t, J = 9.0 Hz), 7.85-7.94 (2H, m). |

Reference Example 65

Preparation of toluene-4-sulfonic acid 2-[1-(2-fluoro-4-nitrophenyl)piperidin-4-yl]ethyl ester

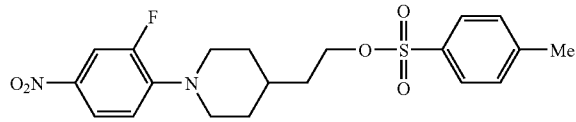

p-Toluenesulfonyl chloride (0.858 g, 4.50 mmol), triethylamine (0.820 ml, 6.00 mmol) and 4-dimethylaminopyridine (0.0366 g, 0.300 mmol) were added to a solution of 2-[1-(2-fluoro-4-nitrophenyl)piperidin-4-yl]ethanol (compound of Reference Example 25; 0.804 g, 3.00 mmol) in anhydrous dichloromethane (5 ml), and the mixture was stirred at room temperature for 17 hours. Water was added to the reaction mixture and the mixture was extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=2:1) to give the title compound (0.661 g, 52%) as a yellow solid.

$^1$H-NMR (CDCl$_3$) δ: 1.27-1.44 (2H, m), 1.61-1.68 (3H, m), 1.70-1.78 (2H, m), 2.46 (3H, s), 2.76-2.88 (2H, m), 3.61-3.71 (2H, m), 4.11 (2H, t, J=6.0 Hz), 6.88 (1H, t, J=9.0 Hz), 7.34-7.39 (2H, m), 7.79-7.83 (2H, m), 7.88 (1H, dd, J=12.9, 2.4 Hz), 7.96 (1H, dd, J=9.0, 2.4 Hz).

Reference Example 66

Preparation of 2-{2-[1-(2-fluoro-4-nitrophenyl)piperidin-4-yl]ethyl}isoindoline-1,3-dione

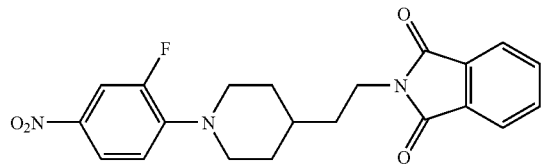

Potassium phthalimide (0.580 g, 4.68 mmol) was added to a solution of toluene-4-sulfonic acid 2-[1-(2-fluoro-4-nitrophenyl)piperidin-4-yl]ethyl ester (compound of Reference Example 65; 0.661 g, 1.56 mmol) in N,N-dimethylformamide (10 ml), and the mixture was stirred at 80° C. for 1 hour. Water was added to the reaction mixture, and the precipitated solid was collected by filtration and washed with water to give the title compound (0.577 g, 93%) as a yellow solid.

$^1$H-NMR (CDCl$_3$) δ: 1.37-1.53 (3H, m), 1.65-1.75 (2H, m), 1.89-1.99 (2H, m), 2.80-2.92 (2H, m), 3.66-3.81 (4H, m), 6.89 (1H, t, J=9.0 Hz), 7.69-7.77 (2H, m), 7.82-7.89 (2H, m), 7.89 (1H, dd, J=13.2, 2.7 Hz), 7.96 (1H, ddd, J=9.0, 2.7, 1.2 Hz).

Reference Example 67

Preparation of 2-[1-(2-fluoro-4-nitrophenyl)piperidin-4-yl]ethylamine

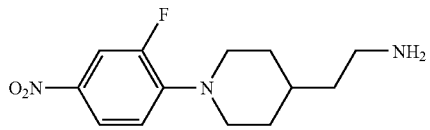

Hydrazine monohydrate (0.272 ml, 5.61 mmol) was added to a solution of 2-{2-[1-(2-fluoro-4-nitrophenyl)piperidin-4-yl]ethyl}isoindoline-1,3-dione (compound of Reference Example 66; 0.745 g, 1.87 mmol) in ethanol (5 ml), and the mixture was stirred at 80° C. for 1 hour. Water was added to the reaction mixture and the mixture was extracted with dichloromethane. The organic layer was washed with saturated aqueous sodium hydrogencarbonate and dried over anhydrous sodium sulfate. The solvent was evaporated under reduced pressure to give the title compound (0.170 g, 34%) as a yellow solid.

$^1$H-NMR (CDCl$_3$) δ: 1.34-1.69 (7H, m), 1.76-1.87 (2H, m), 2.75-2.81 (2H, m), 2.82-2.92 (2H, m), 3.65-3.75 (2H, m), 6.89 (1H, t, J=9.0 Hz), 7.89 (1H, dd, J=13.2, 2.7 Hz), 7.96 (1H, ddd, J=9.0, 2.4, 0.9 Hz).

Reference Example 68

Preparation of [1-(2-fluoro-4-nitrophenyl)piperidin-4-yl](methyl)amine

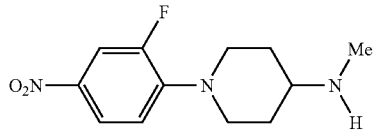

A mixture of 1-(2-fluoro-4-nitrophenyl)piperidin-4-one (compound of Reference Example 26; 5.00 g, 2.10 mmol), methylamine hydrochloride (2.83 g, 4.20 mmol), titanium tetraisopropoxide (11.9 g, 4.20 mmol), triethylamine (4.25 g, 4.20 mmol) and ethanol (25 ml) was stirred at room temperature for 16 hours under argon atmosphere. Sodium borohydride (1.58 g, 4.20 mmol) was added to the reaction mixture, and the mixture was stirred at room temperature for 7 hours. 2.8N aqueous ammonia (25 ml) was added to the reaction mixture at 0° C., and the mixture was stirred for 30 minutes. The reaction mixture was filtered, and the filtrate was extracted with dichloromethane. 2N aqueous hydrochloric acid was added to the organic layer, and the mixture was stirred. The water layer was adjusted to pH=12 by addition of 2N aqueous sodium hydroxide and extracted with dichloromethane. The organic layer was washed with water and saturated brine, and dried over anhydrous sodium sulfate. The solvent was evaporated under reduced pressure to give the title compound (2.12 g, 40%) as a yellow-brown liquid.

$^1$H-NMR (CDCl$_3$) δ: 1.44-1.60 (2H, m), 2.00-2.04 (2H, m), 2.45 (3H, s), 2.56-2.66 (1H, m), 2.93-3.03 (2H, m), 3.60-3.75 (3H, m), 6.91 (1H, t, J=9.0 Hz), 7.89 (1H, dd, J=13.2, 2.4 Hz), 7.94-7.98 (1H, m).

Reference Example 69

Preparation of 2-ethyl-4-(2-fluoro-4-nitrophenyl)piperazine-1-carboxylic acid tert-butyl ester

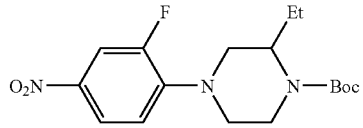

2N Aqueous sodium hydroxide (0.350 ml, 0.700 mmol) and di-tert-butyl dicarbonate (0.146 g, 0.669 mmol) were added to a solution of 3-ethyl-1-(2-fluoro-4-nitrophenyl)piperazine (compound of Reference Example 27; 0.146 g, 0.557 mmol) in anhydrous tetrahydrofuran (11.0 ml) under ice cooling, and the mixture was stirred at room temperature for 2 hours. Water was added to the reaction mixture and the mixture was extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=1:1) to give the title compound (0.166 g, 84%) as an orange solid.

$^1$H-NMR (CDCl$_3$) δ: 0.93 (3H, t, J=7.4 Hz), 1.49 (9H, s), 1.70-1.89 (2H, m), 2.88-3.04 (2H, m), 3.16-3.22 (1H, m), 3.48-3.61 (2H, m), 4.04-4.13 (2H, m), 6.90 (1H, t, J=8.7 Hz), 7.88-7.93 (1H, m), 7.97-8.00 (1H, m).

The compounds described in Reference Examples 70 to 73 were obtained in the same manner as the method of Reference Example 69, except that the compound of Reference Examples 60, 67 or 28 was used instead of the compound of Reference Examples 27.

This compound was obtained in the same manner as the method described in the following document.

J. Med. Chem., vol. 39, No. 3, pp. 673-679 (1996).

Reference Example 75

Preparation of 4-morpholino-3-(trifluoromethyl)aniline

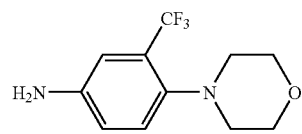

A mixture of 4-[4-nitro-2-(trifluoromethyl)phenyl]morpholine (compound of Reference Example 2; 1.20 g, 4.344 mmol), platinum(IV) oxide (0.10 g) and methanol (12 ml) was stirred at room temperature for 12.5 hours under hydro-

TABLE 9

| Reference Example | Structure | NMR |
|---|---|---|
| 70 | O$_2$N—⟨F⟩—N⟨⟩—N(H)—Boc | Yield: 85%<br>$^1$H-NMR (CDCl$_3$) δ: 1.33-1.47 (2H, m), 1.45 (9H, s), 1.63-1.76 (1H, m), 1.79-1.89 (2H, m), 2.80-2.93 (2H, m), 3.05-3.12 (2H, m), 3.67-3.77 (2H, m), 4.66 (1H, brs), 6.90 (1H, t, J = 9.0 Hz), 7.88 (1H, dd, J = 12.9, 2.7 Hz), 7.96 (1H, ddd, J = 8.7, 2.7, 1.2 Hz). |
| 71 | O$_2$N—⟨F⟩—N⟨⟩—N(H)—Boc | Yield: 95%<br>$^1$H-NMR (CDCl$_3$) δ: 1.33-1.54 (5H, m), 1.45 (9H, s), 1.78-1.89 (2H, m), 2.80-2.92 (2H, m), 3.14-3.25 (2H, m), 3.66-3.75 (2H, m), 4.49 (1H, brs), 6.89 (1H, t, J = 9.0 Hz), 7.88 (1H, dd, J = 12.9, 2.7 Hz), 7.96 (1H, ddd, J = 9.0, 2.7, 0.9 Hz). |
| 72 | O$_2$N—⟨F⟩—N⟨⟩—N(Me)—Boc | Yield: 80%<br>$^1$H-NMR (CDCl$_3$) δ: 1.48 (9H, s), 1.76-1.94 (4H, m), 2.78 (3H, s), 2.90-3.00 (2H, m), 3.74-3.79 (2H, m), 4.16 (1H, brs), 6.92 (1H, t, J = 9.0 Hz), 7.90 (1H, dd, J = 13.2, 2.4 Hz), 7.96-8.00 (1H, m). |
| 73 | O$_2$N—⟨F⟩—N⟨Me⟩—N—Boc | Yield: 95%<br>$^1$H-NMR (CDCl$_3$) δ: 1.32 (3H, d, J = 6.8 Hz), 1.49 (9H, s), 2.89-2.99 (1H, m), 3.05-3.10 (1H, m), 3.24-3.34 (1H, m), 3.47-3.55 (2H, m), 3.96-4.01 (1H, m), 4.36 (1H, brs), 6.90 (1H, t, J = 8.7 Hz), 7.89-7.94 (1H, m), 7.97-8.01 (1H, m). |

Reference Example 74

Preparation of 3-fluoro-4-morpholinoaniline

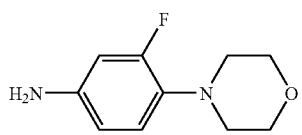

gen atmosphere. The reaction mixture was filtered and the residue obtained by evaporation of the solvent of the filtrate under reduced pressure was washed with n-hexane to give the title compound (0.62 g, 58%) as a colorless crystal.

$^1$H-NMR (CDCl$_3$) δ: 2.83 (4H, t, J=4.5 Hz), 3.73 (2H, brs), 3.80 (4H, t, J=4.5 Hz), 6.81 (1H, dd, J=8.5, 3 Hz), 6.91 (1H, d, J=3 Hz), 7.19 (1H, d, J=8.5 Hz).

The compounds described in Reference Examples 76 to 130 were obtained in the same manner as the method of Reference Example 75 by reduction of the appropriate nitrobenzene derivative.

TABLE 10

| Reference Example | Structure | NMR |
|---|---|---|
| 76 | H₂N–C₆H₃(F)–N(piperidine) | Yield: Quantitative<br>¹H-NMR (CDCl₃) δ: 1.48-1.59 (2H, m), 1.67-1.78 (4H, m) 2.86-2.93 (4H, m), 3.51 (2H, brs), 6.36-6.46 (2H, m), 6.77-6.85 (1H, m). |
| 77 | H₂N–C₆H₃(OMe)–N(piperidine) | Yield: 41%<br>¹H-NMR(CDCl₃) δ: 1.47-1.61 (2H, m), 1.67-1.79 (4H, m), 2.81-2.93 (4H, m), 3.47 (2H, brs), 3.81 (3H, s), 6.22-6.28 (2H, m), 6.74-6.82 (1H, m). |
| 78 | H₂N–C₆H₃(OEt)–N(piperidine) | Yield: 40%<br>¹H-NMR (CDCl₃) δ: 1.36-1.45 (1H, m), 1.52 (3H, t, J = 7.2 Hz), 1.77-2.03 (3H, m), 2.60-2.80 (2H, m), 3.45-3.55 (2H, m), 3.76-3.98 (4H, m), 4.11 (2H, q, J = 7.2 Hz), 6.22-6.28 (2H, m), 8.26-8.35 (1H, m). |
| 79 | H₂N–C₆H₃(CF₃)–N(piperazine)NMe | Yield: 47%<br>¹H-NMR (CDCl₃) δ: 2.34 (3H, s), 2.53 (4H, brs), 2.83-2.90 (4H, m), 3.71 (2H, s), 6.79 (1H, dd, J = 8.7, 2.7 Hz), 6.91 (1H, d, J = 2.7 Hz), 7.21 (1H, d, J = 8.4 Hz). |
| 80 | H₂N–C₆H₃(Cl)–N(piperazine)NMe | Yield: 60%<br>¹H-NMR (CDCl₃) δ: 2.35 (3H, s), 2.59 (4H, brs), 2.78 (4H, brs), 3.53 (2H, s), 6.55 (1H, dd, J = 8.7, 3.0 Hz), 6.74 (1H, d, J = 2.7 Hz), 6.90 (1H, d, J = 8.4 Hz). |
| 81 | H₂N–C₆H₃(Me)–N(piperazine)NMe | Yield: 82%<br>¹H-NMR (CDCl₃) δ: 2.23 (3H, s), 2.34 (3H, s), 2.55 (4H, brs), 2.82-2.88 (4H, m), 3.44 (2H, s), 6.50 (1H, dd, J = 8.4, 2.7 Hz), 6.55 (1H, d, J = 2.7 Hz), 6.89 (1H, d, J = 8.7 Hz). |
| 82 | H₂N–C₆H₃(F)–N(piperazine)N-i-Pr | Yield: Quantitative<br>¹H-NMR (CDCl₃) δ: 1.09 (6H, d, J = 6.6 Hz), 2.66-2.79 (5H, m), 2.97-3.05 (4H, m), 3.53 (2H, brs), 6.37-6.46 (2H, m), 6.82 (1H, t, J =9.0 Hz). |
| 83 | H₂N–C₆H₃(F)–N(piperazine)NEt | Yield: Quantitative<br>¹H-NMR (CDCl₃) δ: 1.13 (3H, t, J = 7.0 Hz), 2.49 (2H, q, J = 7.0 Hz), 2.60-2.68 (4H, m), 3.03 (4H, t, J = 4.5 Hz), 3.48 (2H, brs), 6.35-6.45 (2H, m), 6.79-6.89 (1H, m). |
| 84 | H₂N–C₆H₃(Me)–N(piperazine)NEt | Yield: Quantitative<br>¹H-NMR (CDCl₃) δ: 1.13 (3H, t, J = 7.0 Hz), 2.23 (3H, s), 2.48 (2H, q, J = 7.0 Hz), 2.58 (4H, brs), 2.87 (4H, t, J =5.0 Hz), 3.45 (2H, brs), 6.51 (1H, dd, J = 8.0, 3.0 Hz), 6.56 (1H, d, J = 3.0 Hz), 6.90 (1H, d, J = 8.5 Hz). |
| 85 | H₂N–C₆H₃(F)–N(piperazine)N-C(O)Me | Yield: Quantitative<br>¹H-NMR (CD₃OD) δ: 2.14 (3H, s), 3.07 (2H, t, J = 5.0 Hz), 3.13 (2H, t, J = 5.0 Hz), 3.71 (2H, t, J = 5.0 Hz), 3.75 (2H, t, J = 5.0 Hz), 7.08-7.19 (3H, m). |
| 86 | H₂N–C₆H₃(Me)–N(piperazine)N-C(O)Me | Yield: Quantitative<br>¹H-NMR (CD₃OD) δ: 2.15 (3H, s), 2.40 (3H, s), 2.91 (2H, t, J = 5.0 Hz), 2.97 (2H, t, J = 5.0 Hz), 3.71 (2H, t, J = 5.0 Hz), 3.76 (2H, t, J = 5.0 Hz), 7.20-7.22 (3H, m). |

TABLE 10-continued

| Reference Example | Structure | NMR |
|---|---|---|
| 87 | H2N-C6H3(F)-O-(piperidine)-N-Me | Yield: Quantitative<br>$^1$H-NMR (CDCl$_3$) δ: 1.76-1.85 (2H, m), 1.91-1.99 (2H, m), 2.20 (2H, brs), 2.29 (3H, s), 2.71 (2H, brs), 3.54 (2H, brs), 4.00-4.08 (1H, m), 6.35 (1H, ddd, J = 9.0, 3.0, 1.0 Hz), 6.44 (1H, dd, J = 13.0, 3.0 Hz), 6.83 (1H, t, J = 9.0 Hz). |
| 88 | H2N-C6H3(Me)-O-(piperidine)-N-Me | Yield: Quantitative<br>$^1$H-NMR (CDCl$_3$) δ: 1.79-1.85 (2H, m), 1.90-1.99 (2H, m), 2.17 (3H, s), 2.23 (2H, br), 2.29 (3H, s), 2.67 (2H, br), 3.38 (2H, br), 4.10 (1H, m), 6.47 (1H, dd, J = 9.0, 3.0 Hz), 6.54 (1H, d, J = 3.0 Hz), 6.69 (1H, d, J = 9.0 Hz). |
| 89 | H2N-C6H3(F)-(thiomorpholine) | Yield: 84%<br>$^1$H-NMR (CDCl$_3$) δ: 2.77-2.84 (4H, m), 3.16-3.23 (4H, m), 3.56 (2H, s), 6.36-6.44 (2H, m), 6.81 (1H, t, J = 8.7 Hz). |
| 90 | H2N-C6H3(F)-(piperidine)-NHBoc | Yield: 72%<br>$^1$H-NMR (DMSO-d$_6$) δ: 1.37 (9H, s), 1.40-1.54 (2H, m), 1.67-1.80 (2H, m), 2.50-2.58 (2H, m), 2.96-3.06 (2H, m), 3.18-3.33 (1H, m), 4.93 (2H, s), 6.22-6.34 (2H, m), 6.74 (1H, t, J = 8.4 Hz), 6.82 (1H, d, J = 7.8 Hz). |
| 91 | H2N-C6H3(F)-(piperazine)-CH2-C(=O)-Me | Yield: 40%<br>$^1$H-NMR (CDCl$_3$) δ: 2.18 (3H, s), 2.63-2.70 (4H, m), 3.01-3.07 (4H, m), 3.26 (2H, s), 3.54 (2H, brs), 6.37-6.47 (2H, m), 6.81 (1H, t, J = 9.6 Hz). |
| 92 | H2N-C6H3(F)-O-(piperidine)-Boc | Yield: 97%<br>$^1$H-NMR (CDCl$_3$) δ: 1.46 (9H, s), 1.64-1.78 (2H, m), 1.81-1.93 (2H, m), 3.19-3.28 (2H, m), 3.57 (2H, brs), 3.71-3.80 (2H, m), 4.14-4.22 (1H, m), 6.35 (1H, ddd, J = 8.7, 2.7, 1.5 Hz), 6.45 (1H, dd, J = 12.6, 2.7 Hz), 6.82 (1H, t, J = 8.7 Hz). |
| 93 | H2N-C6H3(F)-(piperazine)-C(=O)-Et | Yield: Quantitative<br>$^1$H-NMR (CD$_3$OD) δ: 1.24 (3H, t, J = 7.0 Hz), 2.46 (2H, q, J = 7.5 Hz), 3.09 (2H, t, J = 5.0 Hz), 3.15 (2H, t, J = 5.0 Hz), 3.72 (2H, t, J = 5.0 Hz), 3.76 (2H, t, J = 5.0 Hz), 3.83 (2H, brs), 7.14-7.20 (3H, m). |
| 94 | H2N-C6H3(F)-(homopiperazine)-N-Me | Yield: Quantitative<br>$^1$H-NMR (CDCl$_3$) δ: 1.97 (2H, q, J = 6.0 Hz), 2.40 (3H, s), 2.69 (2H, t, J = 5.0 Hz), 2.74 (2H, t, J = 5.0 Hz), 3.24-3.29 (4H, m), 3.47 (2H, brs), 6.34-6.44 (2H, m), 6.77 (1H, t, J = 9.0 Hz). |
| 95 | H2N-C6H3(F)-(piperazine)-C(=O)-CH2CH2-(piperidine) | Yield: Quantitative<br>$^1$H-NMR (CD$_3$OD) δ: 1.72-2.02 (6H, m), 2.96-3.05 (4H, m), 3.12 (2H, t, J = 5.0 Hz), 3.18 (2H, t, J = 5.0 Hz), 3.41 (2H, t, J = 6.0 Hz), 3.57-3.60 (4H, m), 3.72 (2H, t, J = 5.0 Hz), 3.78 (2H, t, J = 5.0Hz), 7.15-7.21 (3H, m). |
| 96 | H2N-C6H3(F)-(piperazinone) | Yield: 97%<br>$^1$H-NMR (DMSO-d$_6$) δ: 3.00-3.08 (2H, m), 3.19-3.25 (2H, m), 3.37 (2H, s), 5.06 (2H, s), 6.29-6.40 (2H, m), 6.78 (1H, dd, J = 9.9, 8.7 Hz), 7.86 (1H, s). |

TABLE 10-continued

| Reference Example | Structure | NMR |
|---|---|---|
| 97 | 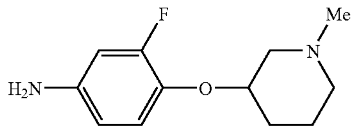 | Yield: 93%<br>$^1$H-NMR (CDCl$_3$) δ: 1.44-1.63 (1H, m), 1.79-1.87 (2H, m), 1.95-2.00 (2H, m), 2.03-2.22 (1H, m), 2.30 (3H, s), 2.57-2.61 (1H, m), 2.90-2.94 (1H, m), 3.54 (2H, brs), 4.04-4.13 (1H, m), 6.32-6.36 (1H, m), 6.43 (1H, dd, J = 12.3, 3.0 Hz), 6.85 (1H, t, J = 8.7 Hz). |
| 98 | 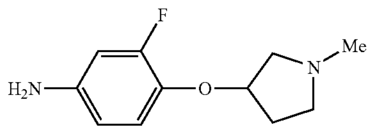 | Yield: 72%<br>$^1$H-NMR (CDCl$_3$) δ: 1.97-2.07 (1H, m), 2.14-2.26 (1H, m), 2.38 (3H, s), 2.46-2.53 (1H, m), 2.72-2.82 (3H, m), 3.52 (2H, brs), 4.68-4.73 (1H, m), 6.33-6.70 (1H, m), 6.45 (1H, dd, J = 12.3, 2.7 Hz), 6.75 (1H, t, J = 9.0 Hz). |
| 99 | 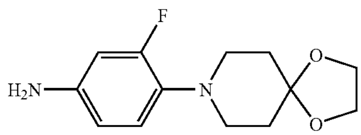 | Yield: 88%<br>$^1$H-NMR (CDCl$_3$) δ: 1.88 (4H, t, J = 5.7 Hz), 3.05 (4H, t, J = 5.7 Hz), 3.53 (2H, brs), 3.99 (4H, s), 6.36-6.45 (2H, m), 6.83 (1H, t, J = 8.7 Hz). |
| 100 | 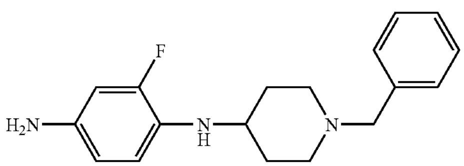 | Yield: Quantitative<br>$^1$H-NMR (CDCl$_3$) δ: 1.39-1.55 (2H, m), 1.93-2.04 (2H, m), 2.05-2.18 (2H, m), 2.77-2.89 (2H, m), 3.10-3.23 (2H, m), 3.35 (2H, brs), 3.51 (2H, s), 6.37 (1H, ddd, J = 8.1, 2.7, 1.2 Hz), 6.42 (1H, dd, J = 12.6, 2.7 Hz), 6.53 (1H, t, J = 9.0 Hz), 7.21-7.35 (5H, m). |
| 101 | 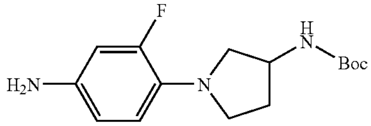 | Yield: Quantitative<br>$^1$H-NMR (CDCl$_3$) δ: 1.45 (9H, s), 1.74-1.90 (1H, m), 2.19-2.33 (1H, m), 3.04-3.18 (2H, m), 3.30-3.53 (4H, m), 4.29 (1H, brs), 4.86 (1H, brs), 6.35-6.48 (2H, m), 6.57 (1H, t, J = 9.0 Hz). |
| 102 | 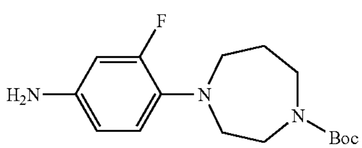 | Yield: Quantitative<br>$^1$H-NMR (CDCl$_3$) δ: 1.45-1.46 (9H, m), 1.90-1.94 (2H, m), 3.16-3.23 (4H, m), 3.45-3.60 (6H, m), 6.33-6.43 (2H, m), 6.79 (1H, t, J = 9.6 Hz). |
| 103 | 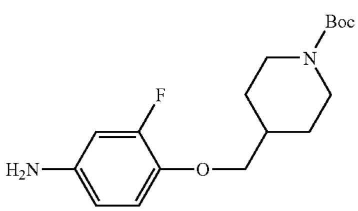 | Yield: Quantitative<br>$^1$H-NMR (CDCl$_3$) δ: 1.23-1.28 (2H, m), 1.46 (9H, s), 1.80-1.85 (2H, m), 1.85-1.99 (1H, m), 2.70-2.82 (2H, m), 3.52 (2H, brs), 3.77 (2H, d, J = 6.6 Hz), 4.10-4.18 (2H, m), 6.33-6.38 (1H, m), 6.46 (1H, dd, J = 12.6, 2.7 Hz), 6.78 (1H, t, J = 9.0 Hz). |
| 104 | 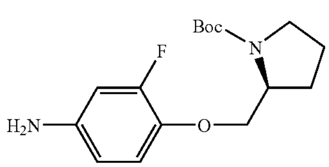 | Yield: Quantitative<br>$^1$H-NMR (CDCl$_3$) δ: 1.46 (9H, s), 1.85-2.20 (4H, m), 3.22-3.55 (3H, m), 3.70-3.84 (1H, m), 3.87-3.99 (1H, m), 4.08 (2H, brs), 6.35 (1H, ddd, J = 8.4, 2.4, 1.2 Hz), 6.45 (1H, dd, J = 12.9, 2.7 Hz), 6.76-6.94 (1H, m). |
| 105 | 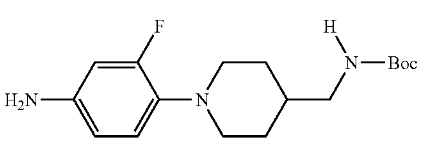 | Yield: Quantitative<br>$^1$H-NMR (CDG1s) δ: 1.35-1.65 (3H, m), 1.45 (9H, s), 1.73-1.80 (2H, m), 2.52-2.64 (2H, m), 3.02-3.11 (2H, m), 3.23-3.32 (2H, m), 3.52 (2H, s), 4.64 (1H, brs), 6.35-6.46 (2H, m), 6.80 (1H, t, J = 8.4 Hz). |

US 7,671,058 B2
93                                                                        94

TABLE 10-continued

| Reference Example | Structure | NMR |
|---|---|---|
| 106 | 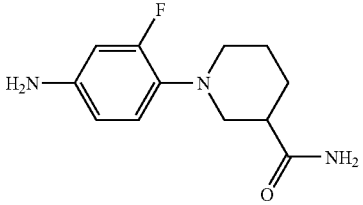 | Yield: 98%<br>$^1$H-NMR (DMSO-d$_6$) δ: 1.33-1.47 (1H, m), 1.48-1.65 (1H, m), 1.65-1.75 (1H, m), 1.75-1.86 (1H, m), 2.36-2.54 (2H, m), 2.54-2.66 (1H, m), 2.95-3.12 (2H, m), 4.97 (2H, s), 626-6.37 (2H, m), 6.73-6.85 (2H, m), 7.33 (1H, brs). |
| 107 | 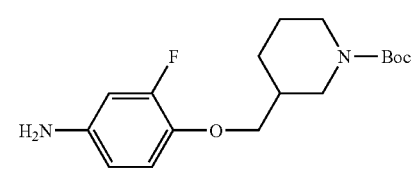 | Yield: 75%<br>$^1$H-NMR (CDCl$_3$) δ: 1.30-1.71 (12H, m), 1.84-2.00 (2H, m), 2.74-2.96 (2H, m), 3.50 (2H, s), 3.79-3.90 (3H, m), 4.00-4.10 (1H, m), 6.33-6.37 (1H, m), 6.45 (1H, dd, J = 12.6, 2.7 Hz), 6.77 (1H, t, J = 9.0 Hz). |
| 108 | 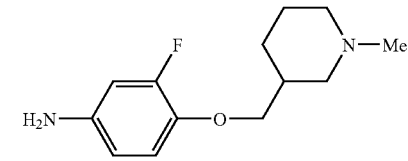 | Yield: Quantitative<br>$^1$H-NMR (CDCl$_3$) δ: 1.61-2.18 (7H, m), 2.28 (3H, s), 2.71-3.00 (2H, m), 3.50 (2H, brs), 3.76-3.84 (2H, m), 6.31-6.38 (1H, m), 6.41-6.48 (1H, m), 6.75-6.81 (1H, m). |
| 109 | 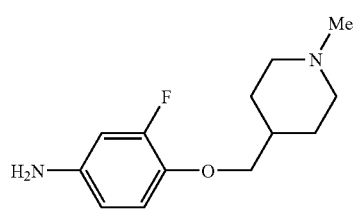 | Yield: 55%<br>$^1$H-NMR (CDCl$_3$) δ: 1.33-1.45 (2H, m), 1.72-2.00 (5H, m), 2.28 (3H, s), 2.86-2.91 (2H, m), 3.45 (2H, brs), 3.78 (2H, d, J = 6.3 Hz), 6.33-6.38 (1H, m), 6.45 (1H, dd, J = 12.6, 2.7 Hz), 6.78 (1H, t, J = 9.0 Hz). |
| 110 | 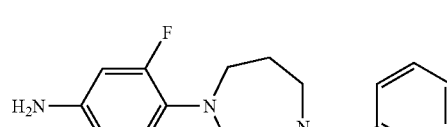 | Yield: 89%<br>$^1$H-NMR (CDCl$_3$) δ: 1.92-1.98 (2H, m), 2.73-2.81 (4H, m), 3.24-3.29 (4H, m), 3.51 (2H, brs), 3.68 (2H, s), 6.32-6.42 (2H, m), 6.76 (1H, t, J = 9.0 Hz), 7.21-7.37 (5H, m). |
| 111 | 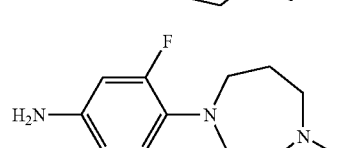 | Yield: Quantitative<br>$^1$H-NMR (CDCl$_3$) δ: 1.09 (3H, t, J = 7.2 Hz), 1.91-1.99 (2H, m), 2.60 (2H, q, J = 7.2 Hz), 2.72-2.81 (4H, m), 3.23-3.28 (4H, m), 3.51 (2H, brs), 6.33-6.43 (2H, m), 6.76 (1H, t, J = 9.0 Hz). |
| 112 | 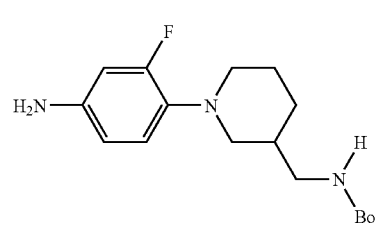 | Yield: 90%<br>$^1$H-NMR (CDCl$_3$) δ: 1.17-1.31 (1H, m), 1.45 (9H, s), 1.65-1.97 (4H, m), 2.37-2.50 (1H, m), 2.54-2.65 (1H, m), 3.04-3.20 (4H, m), 3.53 (2H, s), 4.63 (1H, brs), 6.36-6.46 (2H, m), 6.80 (1H, t, J = 9.0 Hz). |
| 113 | 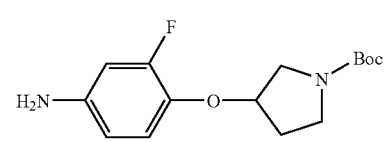 | Yield: 95%<br>$^1$H-NMR (CDCl$_3$) δ: 1.47 (9H, s), 1.87-2.02 (1H, m), 2.10-2.22 (1H, m), 3.25-3.70 (6H, m), 4.71 (1H, brs), 6.36 (1H, dd, J = 8.7, 2.7 Hz), 6.45 (1H, dd, J = 12.6, 2.7 Hz), 6.78 (1H, t, J = 9.0 Hz). |
| 114 | 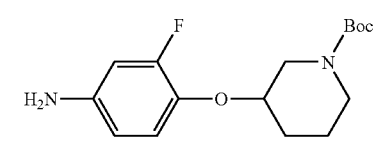 | Yield: 98%<br>$^1$H-NMR (CDCl$_3$) δ: 1.44 (9H, s), 1.60-2.06 (6H, m), 3.19 (2H, brs), 3.56-3.61 (2H, m), 3.96-4.00 (1H, m), 6.33-6.37 (1H, m), 6.44 (1H, dd, J = 12.6, 2.7 Hz), 6.86 (1H, t, J = 9.0 Hz). |

TABLE 10-continued

| Reference Example | Structure | NMR |
|---|---|---|
| 115 | 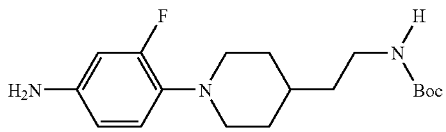 | Yield: 96%<br>$^1$H-NMR (CDCl$_3$) δ: 1.33-1.52 (5H, m), 1.45 (9H, s), 1.72-1.82 (2H, m), 2.51-2.62 (2H, m), 3.12-3.30 (4H, m), 3.51 (2H, brs), 4.47 (1H, brs), 6.35-6.45 (2H, m), 6.76-6.85 (1H, m). |
| 116 | 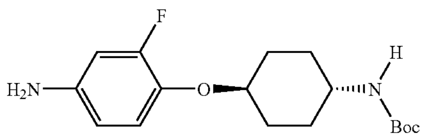 | Yield: 78%<br>$^1$H-NMR (CDCl$_3$) δ: 1.10-1.24 (2H, m), 1.44 (9H, s), 1.48-1.65 (2H, m), 2.05-2.08 (4H, m), 3.49-3.54 (3H, m), 3.86-3.93 (1H, m), 4.37 (1H, brs), 6.32-6.36 (1H, m), 6.43 (1H, dd, J = 12.6, 2.7 Hz), 6.81 (1H, t, J = 9.0 Hz). |
| 117 | 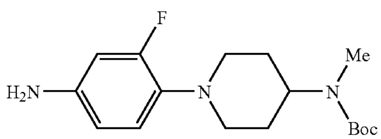 | Yield: 74%<br>$^1$H-NMR (CDCl$_3$) δ: 1.48 (9H, s), 1.68-1.73 (2H, m), 1.84-1.93 (2H, m), 2.65-2.76 (2H, m), 2.78 (3H, s), 3.30-3.34 (2H, m), 3.53 (2H, brs), 401-4.13 (1H, m), 6.37-6.45 (2H, m), 6.78-6.84 (1H, m). |
| 118 | 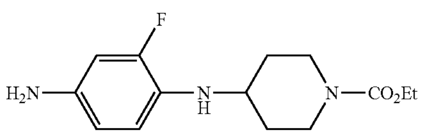 | Yield: 99%<br>$^1$H-NMR (CDCl$_3$) δ: 1.26 (3H, t, J = 7.2 Hz), 1.26-1.42 (2H, m), 1.96-2.09 (2H, m), 2.87-3.02 (3H, m), 3.25-3.36 (3H, m), 4.07 (2H, brs), 4.13 (2H, q, J = 7.2 Hz), 6.39 (1H, ddd, J = 8.4, 2.4, 1.2 Hz), 6.44 (1H, dd, J = 12.6, 2.4 Hz), 6.61 (1H, t, J = 8.7 Hz). |
| 119 | 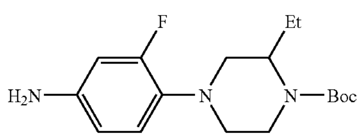 | Yield: 53%<br>$^1$H-NMR (CDCl$_3$) δ: 0.92 (3H, t, J = 7.5 Hz), 1.47 (9H, s), 1.78-1.94 (2H, m), 2.63-2.72 (2H, m), 3.06-3.21 (3H, m), 3.56 (2H, brs), 3.99 (2H, brs), 6.36-6.44 (2H, m), 6.75 (1H, t, J = 8.6 Hz). |
| 120 | 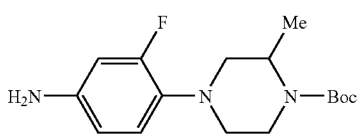 | Yield: 55%<br>$^1$H-NMR (CDCl$_3$) δ: 1.35 (3H, d, J = 6.6 Hz), 1.48 (9H, s), 2.63-2.71 (1H, m), 2.73-2.78 (1H, m), 3.01-3.13 (2H, m), 3.20-3.29 (1H, m), 3.57 (2H, brs), 3.88-3.93 (1H, m), 4.28 (1H, brs), 6.36-6.44 (2H, m), 6.74 (1H, t, J = 8.4 Hz). |
| 121 | 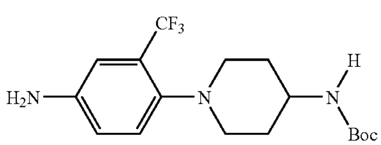 | Yield: Quantitative<br>$^1$H-NMR (CDCl$_3$) δ: 1.45 (9H, s), 1.49-1.60 (2H, m), 1.90-1.97 (2H, m), 2.68-2.76 (2H, m), 2.89-2.93 (2H, m), 3.54 (1H, brs), 3.71 (2H, s), 4.48 (1H, brs), 6.78 (1H, dd, J = 8.4, 2.7 Hz), 6.88 (1H, d, J = 2.7 Hz), 7.16 (1H, d, J = 8.4 Hz). |
| 122 | 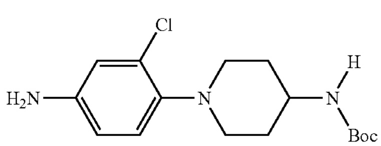 | Yield: Quantitative<br>$^1$H-NMR (CDCl$_3$) δ: 1.46 (9H, s), 1.54-1.67 (2H, m), 1.99-2.03 (2H, m), 2.63-2.71 (2H, m), 3.15-3.19 (2H, m), 3.53 (3H, brs), 4.49 (1H, brs), 6.54 (1H, dd, J = 8.4, 2.7 Hz), 6.74 (1H, d, J = 2.7 Hz), 6.88 (1H, d, J = 8.4 Hz). |
| 123 | 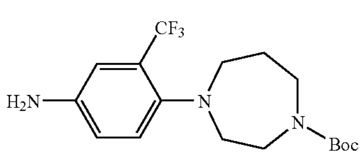 | Yield: 91%<br>$^1$H-NMR (CDCl$_3$) δ: 1.49 (9H, s), 1.83-1.91 (2H, m), 2.93-2.98 (4H, m), 3.46-3.59 (4H, m), 6.77-6.88 (2H, m), 7.10 (1H, d, J = 8.1 Hz). |
| 124 | 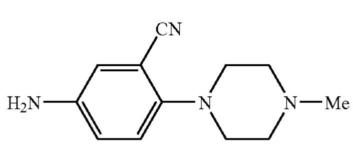 | Yield: 77%<br>$^1$H-NMR (CDCl$_3$) δ: 2.36 (3H, s), 2.62 (4H, t, J = 4.5 Hz), 3.08 (4H, t, J = 4.5 Hz), 3.62 (2H, brs), 6.81-6.93 (3H, m). |

TABLE 10-continued

| Reference Example | Structure | NMR |
|---|---|---|
| 125 | 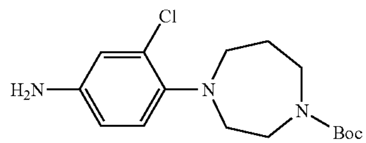 | Yield: 63%<br>$^1$H-NMR (CDCl$_3$) δ: 1.48 (9H, s), 1.90-2.02 (2H, m), 3.02-3.11 (4H, m), 3.55-3.62 (6H, m), 6.51 (1H, d, J = 8.4 Hz), 6.73 (1H, d, J = 2.4 Hz), 6.90 (1H, dd, J = 8.4, 2.4 Hz). |
| 126 | 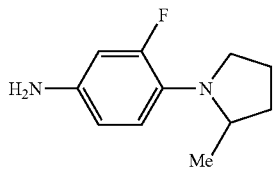 | Yield: Quantitative<br>$^1$H-NMR (CDCl$_3$) δ: 1.04 (3H, d, J = 6.0 Hz), 1.50-1.68 (1H, m), 1.73-2.02 (2H, m), 2.04-2.20 (1H, m), 2.91-3.04 (1H, m), 3.22-3.60 (3H, m), 3.62-3.78 (1H, m), 6.34-6.50 (2H, m), 6.69 (1H, t, J = 9.0 Hz). |
| 127 | 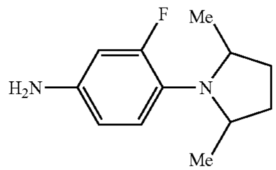 | This compound was obtained as a diastereomeric mixture.<br>Yield: Quantitative<br>$^1$H-NMR(CDCl$_3$) δ (major isomer): 1.01 (6H, d, J = 6.0 Hz), 1.41-1.63 (2H, m), 1.86-2.05 (2H, m), 3.12-3.38 (2H, m), 3.47 (2H, brs), 6.32-6.51 (2H, m), 6.94 (1H, t, J = 8.8 Hz).<br>δ (minor isomer): 0.93 (6H, d, J = 6.0 Hz), 1.41-1.63 (2H, m), 2.08-2.22 (2H, m), 3.79-3.97 (2H, m), 4.56 (2H, brs), 6.32-6.51 (2H, m), 6.68 (1H, t, J = 9.6 Hz). |
| 128 | 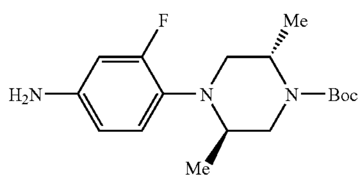 | Yield: Quantitative<br>$^1$H-NMR (DMSO-d$_6$) δ: 0.80 (3H, d, J = 6.5 Hz), 1.18 (3H, d, J = 7.0 Hz), 1.40 (9H, s), 3.25-3.38 (4H, m), 3.58 (1H, d, J = 12.0 Hz), 4.19-4.28 (1H, m), 4.97 (2H, s), 6.26-6.35 (2H, m), 6.66 (1H, t, J = 9.0 Hz). |
| 129 | 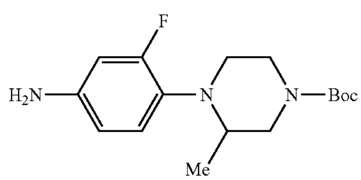 | Yield: 92%<br>$^1$H-NMR (CDCl$_3$) δ: 0.86 (3H, d, J = 6.2 Hz), 1.48 (9H, s), 2.80-3.30 (6H, m), 3.62 (2H, brs), 3.74-3.78 (1H, m), 6.37-6.41 (2H, m), 6.88 (1H, t, J = 8.4 Hz). |
| 130 | 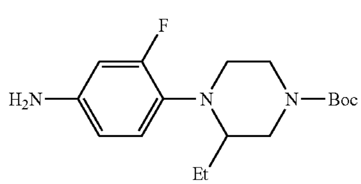 | Yield: 68%<br>$^1$H-NMR (CDCl$_3$) δ: 0.80 (3H, t, J = 7.4 Hz), 1.48 (9H, s), 1.26-1.31 (2H, m), 2.79-2.86 (1H, m), 2.98-3.12 (2H, m), 3.31-3.85 (6H, m), 6.36-6.41 (2H, m), 6.84 (1H, brs). |

Reference Example 131

Preparation of 4-piperidino-3-(trifluoromethyl)aniline

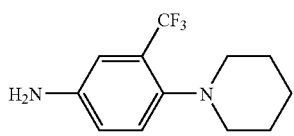

A mixture of 1-fluoro-4-nitro-2-(trifluoromethyl)benzene (1.05 g, 5.00 mmol), piperidine (0.592 ml, 6.00 mmol), diisopropylethylamine (1.31 ml, 7.50 mmol) and acetonitrile (10 ml) was refluxed for 8 hours. Methanol (10 ml) and 10% platinum on activated carbon (0.10 g) were added to the residue obtained by evaporation of the solvent of the reaction mixture under reduced pressure, and the mixture was stirred at room temperature for 12 hours under hydrogen atmosphere. The reaction mixture was filtered through celite. The residue obtained by concentration of the filtrate under reduced pressure was purified by column chromatography on silica gel (n-hexane:ethyl acetate=1:1) to give the title compound (1.11 g, 91%) as a colorless liquid.

$^1$H-NMR (CDCl$_3$) δ: 1.45-1.58 (2H, m), 1.61-1.71 (4H, m), 2.70-2.79 (4H, m), 3.67 (2H, brs), 6.78 (1H, dd, J=8.7, 3.0 Hz), 6.89 (1H, d, J=2.7 Hz), 7.17 (1H, d, J=8.4 Hz).

The compounds described in Reference Examples 132 to 137 were obtained in the same manner as the method of Reference Example 131 by reduction of the nitrobenzene derivative obtained by reacting the appropriate 4-halogenated nitrobenzene derivative with the cyclic compound.

4-nitro-2-(trifluoromethyl)benzene (1.05 g, 5.00 mmol) was added to the reaction mixture under ice cooling, and the mixture was refluxed for 3 hours. Ice water was added to the reaction mixture and the mixture was extracted with ethyl acetate. The organic layer was washed with saturated brine

TABLE 11

| Reference Example | Structure | NMR |
|---|---|---|
| 132 | (structure) | Yield: 84%<br>$^1$H-NMR (CDCl$_3$) δ: 1.88-1.97 (4H, m), 3.14-3.26 (4H, m), 3.41 (2H, s), 6.39 (1H, dd, J = 8.4, 3.0 Hz), 6.45 (1H, dd, J = 14.4, 2.4 Hz), 6.61 (1H, dd, J = 9.9, 8.7 Hz). |
| 133 | (structure) | Yield: 92%<br>$^1$H-NMR (CDCl$_3$) δ: 1.56-1.68 (4H, m), 1.73-1.83 (4H, m), 3.18-3.22 (4H, m), 3.43 (2H, s), 6.34-6.44 (2H, m), 6.76 (1H, dd, J = 9.6, 8.4 Hz). |
| 134 | (structure) | Yield: 95%<br>$^1$H-NMR (CDCl$_3$) δ: 1.48-1.59 (2H, m), 1.66-1.78 (4H, m), 2.81-2.90 (4H, m), 3.50 (2H, s), 6.54 (1H, dd, J = 8.4, 2.7 Hz), 6.74 (1H, d, J = 2.7 Hz), 6.87 (1H, d, J = 8.7 Hz). |
| 135 | (structure) | Yield: 90%<br>$^1$H-NMR (CDCl$_3$) δ: 1.47-1.58 (2H, m), 1.62-1.73 (4H, m), 2.23 (3H, s), 2.69-2.78 (4H, m), 3.41 (2H, s), 6.49 (1H, dd, J = 8.4, 2.7 Hz), 6.55 (1H, d, J = 2.7 Hz), 6.85 (1H, d, J = 8.1 Hz). |
| 136 | (structure) | Yield: 54%<br>$^1$H-NMR (CDCl$_3$) δ: 2.35 (3H, s), 2.54-2.63 (4H, m), 2.96-3.04 (4H, m), 3.53 (2H, s), 6.37-6.45 (2H, m), 6.78-6.84 (1H, m). |
| 137 | (structure) | Yield: 70%<br>$^1$H-NMR (CDCl$_3$) δ: 1.66-1.84 (6H, m), 1.91-2.01 (2H, m), 2.01-2.20 (1H, m), 2.56-2.70 (6H, m), 3.25-3.34 (2H, m), 3.51 (2H, s), 6.35-6.45 (2H, m), 6.77-6.83 (1H, m). |

Reference Example 138

Preparation of 4-cyclohexyloxy-3-(trifluoromethyl)aniline

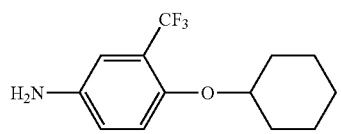

A solution of cyclohexanol (1.00 g, 10.0 mmol) in anhydrous tetrahydrofuran (6 ml) was added dropwise to a suspension of 60% sodium hydride (0.240 g, 6.00 mmol) in anhydrous tetrahydrofuran (6 ml) under ice cooling, and the mixture was stirred at room temperature for 1 hour. 1-Fluoro- and dried over anhydrous sodium sulfate. Methanol (10 ml) and 10% platinum on activated carbon (0.100 g) were added to the residue obtained by evaporation of the solvent under reduced pressure, and the mixture was stirred at room temperature for 12 hours under hydrogen atmosphere. The reaction mixture was filtered through celite. The residue obtained by concentration of the filtrate under reduced pressure was purified by column chromatography on silica gel (n-hexane:ethyl acetate=1:1) to give the title compound (0.60 g, 47%) as a colorless liquid.

$^1$H-NMR (CDCl$_3$) δ: 1.30-1.68 (6H, m), 1.72-1.84 (2H, m), 1.84-1.96 (2H, m), 3.51 (2H, brs), 4.50-4.61 (1H, m), 6.77 (1H, dd, J=9.0, 2.7 Hz), 6.85 (1H, d, J=8.7 Hz), 6.90 (1H, d, J=2.7 Hz).

The compound described in Reference Example 139 was obtained in the same manner as the method of Reference Example 138, except that 3,4-difluoronitrobenzene was used instead of 1-fluoro-4-nitro-2-(trifluoromethyl)benzene.

TABLE 12

| Reference Example | Structure | NMR |
|---|---|---|
| 139 | 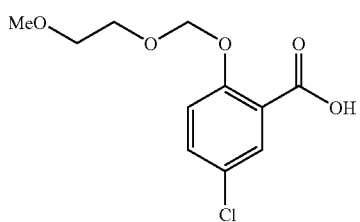 | Yield: 69%<br>$^1$H-NMR (CDCl$_3$) δ: 1.18-1.37 (3H, m), 1.42-1.59 (3H, m), 1.72-1.87 (2H, m), 1.90-2.01 (2H, m), 3.52 (2H, brs), 3.92-4.00 (1H, m), 6.35 (1H, ddd, J = 8.4, 2.7, 1.2 Hz), 6.44 (1H, dd, J = 12.3, 2.7 Hz), 6.82 (1H, t, J = 9.0 Hz). |

Reference Example 140

Preparation of 5-chloro-2-(2-methoxyethoxymethoxy)benzoic acid

Sodium hydroxide (7.20 g, 180 mmol) was added to a solution of 5-chlorosalicylic acid (10.36 g, 60 mmol) in tetrahydrofuran (60 ml). (2-Methoxyethoxy)methyl chloride (15.1 ml, 132 mmol) was added to the mixture, and the mixture was stirred for 18 hours. 2N Aqueous sodium hydroxide (80 ml) was added to the reaction mixture, and the mixture was refluxed for 2 hours. The water layer was adjusted to pH=3 by addition of 2N hydrochloric acid and extracted with ethyl acetate. The organic layer was washed with saturated brine and dried over anhydrous sodium sulfate. The residue obtained by evaporation of the solvent under reduced pressure was purified by column chromatography on silica gel (n-hexane ethyl acetate=1:1) to give the title compound (12.8 g, 82%) as a colorless liquid.

$^1$H-NMR (CDCl$_3$) δ: 3.36 (3H, s), 3.54-3.60 (2H, m), 3.87-3.91 (2H, m), 5.49 (2H, s), 7.26 (1H, d, J=9.0 Hz), 7.49 (1H, dd, J=3.0, 9.0 Hz), 8.11 (1H, d, J=2.7 Hz), 10.00 (1H, brs).

The compounds described in Reference Examples 141 and 142 were obtained in the same manner as the method of Reference Example 140, except that 5-bromosalicylic acid or 4-chlorosalicylic acid was used instead of 5-chlorosalicylic acid.

TABLE 13

| Reference Example | Structure | NMR |
|---|---|---|
| 141 | MEMO, OH, Br | Yield: 88%<br>$^1$H-NMR (CDCl$_3$) δ: 3.36 (3H, s), 3.55-3.58 (2H, m), 3.88-3.91 (2H, m), 5.49 (2H, s), 7.20 (1H, d, J = 8.7 Hz), 7.63 (1H, dd, J = 8.7, 2.7 Hz), 8.25 (1H, d, J = 2.7 Hz). |

TABLE 13-continued

| Reference Example | Structure | NMR |
|---|---|---|
| 142 | MEMO, OH, Cl | Yield: 51%<br>$^1$H-NMR (CDCl$_3$) δ: 3.33 (3H, s), 3.57-3.60 (2H, m), 3.92-3.95 (2H, m), 5.52 (2H, s), 7.15 (1H, dd, J = 8.7, 2.1 Hz), 7.33 (1H, d, J = 2.1 Hz), 8.09 (1H, d, J = 8.7 Hz). |

Reference Example 143

Preparation of (1-{4-[5-chloro-2-(2-methoxyethoxymethoxy)benzoylamino]-2-fluorophenyl}piperidin-4-yl)carbamic acid tert-butyl ester

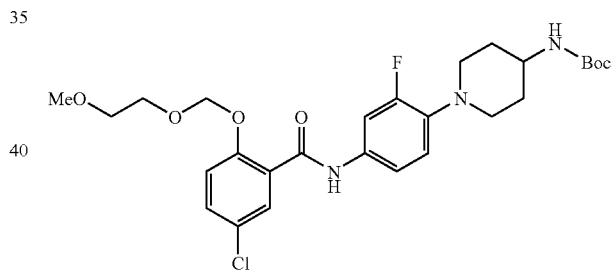

A mixture of 5-chloro-2-(2-methoxyethoxymethoxy)benzoic acid (compound of Reference Example 140; 0.18 g, 0.7 mmol), [1-(4-amino-2-fluorophenyl)piperidin-4-yl]carbamic acid tert-butyl ester (compound of Reference Example 90; 0.28 g, 0.9 mmol), 1-ethyl-3-(3-dimethylaminopropyl)carbodiimide hydrochloride (0.17 g, 0.9 mmol), 4-dimethylaminopyridine (0.01 g) and dichloromethane (5 ml) was stirred at room temperature for 18 hours. Water was added to the reaction mixture and the mixture was extracted with ethyl acetate. The ethyl acetate layer was washed with saturated brine and dried over anhydrous sodium sulfate. The residue obtained by evaporation of the solvent under reduced pressure was purified by column chromatography on silica gel (n-hexane:ethyl acetate=1:1) to give the title compound (0.27 g, 70%) as a colorless solid.

$^1$H-NMR (CDCl$_3$) δ: 1.46 (9H, s), 1.54-1.69 (2H, m), 2.00-2.10 (2H, m), 2.71-2.83 (2H, m), 3.30-3.41 (5H, m), 3.53-3.67 (3H, m), 3.86-3.92 (2H, m), 4.50 (1H, d, J=7.2 Hz), 5.47 (2H, s), 6.93 (1H, t, J=9.0 Hz), 7.17 (1H, d, J=9.0 Hz), 7.22-7.28 (1H, m), 7.39 (1H, dd, J=8.1, 2.7 Hz), 7.55 (1H, dd, J=13.8, 2.1 Hz), 8.18 (1H, d, J=3.0 Hz), 9.61 (1H, s).

The compounds described in Reference Examples 144 to 182 were obtained in the same manner as the method of Reference Example 143, by reacting the appropriate aniline derivative with the carboxylic acid derivative.

TABLE 14

| Reference Example | Structure | NMR |
|---|---|---|
| 144 | 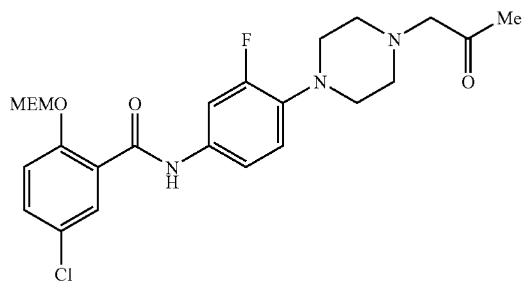 | Yield: 94%<br>¹H-NMR (CDCl₃) δ: 2.18 (3H, s), 2.64-2.74 (4H, m), 3. 10-3.18 (4H, m), 3.28 (2H, s), 3.33 (3H, s), 3.55-3.60 (2H, m), 3.87-3.92 (2H, m), 5.48 (2H, s), 6.94 (1H, t, J = 9.0 Hz), 7.18 (1H, d, J = 8.7 Hz), 7.23-7.29 (1H, m), 7.41 (1H, dd, J = 9.0, 2.7 Hz), 7.57 (1H, dd, J = 14.1, 2.7 Hz), 8.18 (1H, d, J = 2.7 Hz), 9.63 (1H, s). |
| 145 | 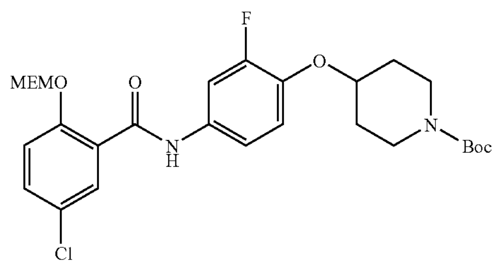 | Yield: 83%<br>¹H-NMR (CDCl₃) δ: 1.47 (9H, s), 1.71-1.84 (2H, m), 1.86-1.98 (2H, m), 3.25-3.43 (5H, m), 3.55-3.61 (2H, m), 3.70-3.79 (2H, m), 3.88-3.93 (2H, m), 4.35-4.44 (1H, m), 5.48 (2H, s), 6.99 (1H, t, J = 9.0 Hz), 7.18 (1H, d, J = 8.7 Hz), 7.25-7.31 (1H, m), 7.41 (1H, dd, J = 9.3, 2.7 Hz), 7.59 (1H, dd, J = 12.9, 2.7 Hz), 8.18 (1H, d, J = 2.7 Hz), 9.65 (1H, s). |
| 146 | 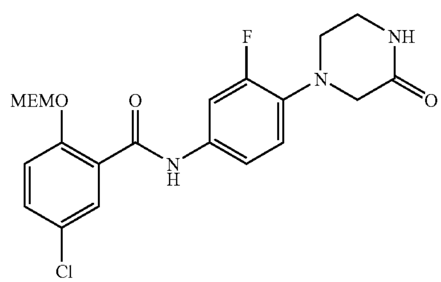 | Yield 57%<br>¹H-NMR (DMSO-d₆) δ: 3.19 (3H, s), 3.20-3.30 (4H, m), 3.42-3.47 (2H, m), 3.56 (2H, s), 3.72-3.78 (2H, m), 5.35 (2H, s), 7.04 (1H, t, J = 9.3 Hz), 7.29 (1H, d, J = 9.3 Hz), 7.39 (1H, dd, J = 8.7, 2.1 Hz), 7.53 (1H, dd, J = 9.0, 2.7 Hz), 7.59 (1H, d, J = 2.4 Hz), 7.67 (1H, dd, J = 14.7, 2.4 Hz), 7.96 (1H, s), 10.28 (1H, s). |
| 147 | 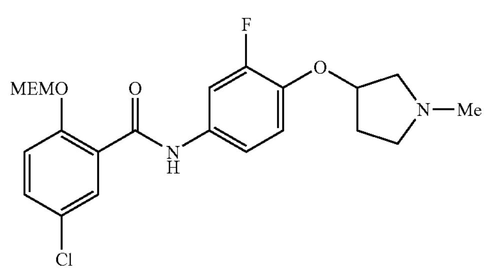 | Yield: 82%<br>¹H-NMR (CDCl₃) δ: 1.81-1.91 (1H, m), 2.25-2.32 (1H, m), 2.40 (3H, s), 2.43-2.53 (2H, m), 2.76-2.91 (2H, m), 3.33 (3H, s), 3.55-3.59 (2H, m), 3.88-3.91 (2H, m), 4.82-4.87 (1H, m), 5.48 (2H, s), 6.89 (1H, t, J = 8.7 Hz), 7.18 (1H, d, J = 8.7 Hz), 7.26-7.31 (1H, m), 7.41 (1H, dd, J = 8.7, 2.7 Hz), 7.54 (1H, dd, J = 12.6, 2.7 Hz), 8.18 (1H, d, J = 2.7 Hz), 9.61 (1H, brs). |
| 148 | 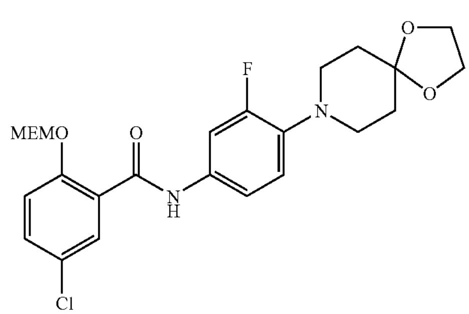 | Yield: Quantitative<br>¹H-NMR (CDCl₃) δ: 1.90 (4H, t, J = 6.0 Hz), 3.16 (4H, t, J = 6.0 Hz), 3.33 (3H, s), 3.56-3.59 (2H, m), 3.89-3.91 (2H, m, 4.00 (4H, s), 5.48 (2H, s), 6.96 (1H, t, J = 9.0 Hz), 7.17 (1H, d, J = 9.0 Hz), 7.24-7.28 (1H, m), 7.40 (1H, dd, J = 9.0, 2.7 Hz), 7.55 (1H, dd, J = 13.8, 2.4 Hz), 8.18 (1H, d, J = 2.7 Hz), 9.61 (1H, brs). |

TABLE 14-continued

| Reference Example | Structure | NMR |
|---|---|---|
| 149 | 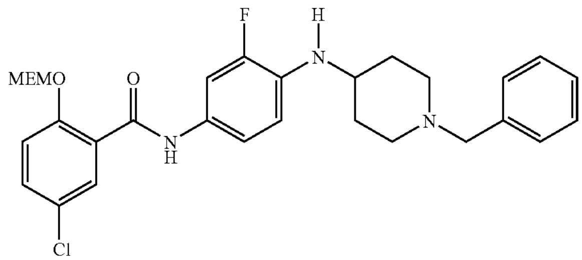 | Yield: 89%<br>¹H-NMR (CDCl₃) δ: 1.42-1.59 (2H, m), 1.95-2.10 (2H, m), 2.11-2.23 (2H, m), 2.78-2.91 (2H, m), 3.24-3.39 (4H, m), 3.51-3.58 (3H, m), 3.86-3.91 (2H, m), 5.29 (2H, s), 5.46 (2H, s), 6.67 (1H, t, J = 9.0 Hz), 7.17 (1H, d, J = 8.7 Hz), 7.24-7.35 (6H, m), 7.39 (1H, dd, J = 8.7, 2.7 Hz), 7.49 (1H, dd, J = 13.2, 2.4 Hz), 8.17 (1H, d, J = 2.7 Hz), 9.48 (1H, s). |
| 150 | 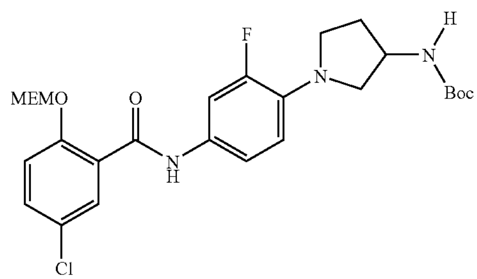 | Yield: 66%<br>¹H-NMR (CDCl₃) δ: 1.46 (9H, s), 1.82-1.95 (1H, m), 2.19-2.32 (1H, m), 3.22-3.38 (2H, m), 3.34 (3H, s), 3.51-3.61 (4H, m), 3.87-3.92 (2H, m), 4.33 (1H, brs), 4.82 (1H, brs), 5.47 (2H, s), 6.64 (1H, t, J = 9.0 Hz), 7.17 (1H, d, J = 8.7 Hz), 7.19-7.24 (1H, m), 7.39 (1H, dd, J = 8.7, 2.7 Hz), 7.52 (1H, dd, J = 15.0, 2.7 Hz), 8.19 (1H, d, J = 3.0 Hz), 9.55 (1H, s). |
| 151 | 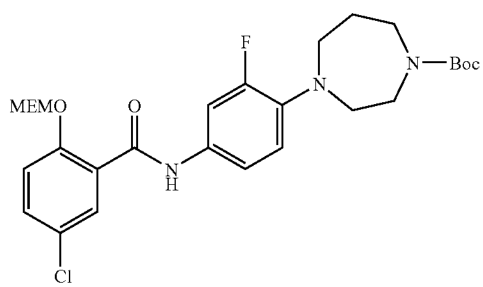 | Yield: 17%<br>¹H-NMR (CDCl₃) δ: 1.43-1.46 (9H, m), 1.94-2.04 (2H, m), 3.34-3.62 (13H, m), 3.88-3.91 (2H, m), 5.47 (2H, s), 6.87 (1H, t, J = 9.0 Hz), 7.16-7.28 (2H, m), 7.40 (1H, dd, J = 9.0, 3.0 Hz), 7.52 (1H, dd, J = 15.3, 2.4 Hz), 8.18 (1H, d, J = 2.7 Hz), 9.57 (1H, brs). |
| 152 | 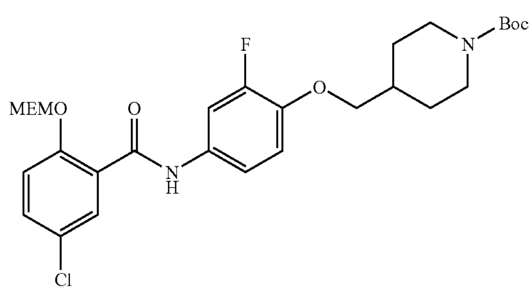 | Yield: 28%<br>¹H-NMR (CDCl₃) δ: 1.22-1.34 (2H, m), 1.47 (9H, s), 1.83-1.87 (2H, m), 1.99-2.04 (1H, m), 2.71-2.94 (2H, m), 3.33 (3H, s), 3.56-359 (2H, m), 3.85-3.91 (4H, m), 4.11-4.18 (2H, m), 5.48 (2H, s), 6.93 (1H, t, J = 9.0 Hz), 7.17 (1H, d, J = 8.7 Hz), 7.28-7.33 (1H, m), 7.41 (1H, dd, J = 8.7, 2.7 Hz), 7.55 (1H, dd, J = 12.6, 2.7 Hz), 8.18 (1H, d, J = 2.7 Hz), 9.61 (1H, brs). |
| 153 | 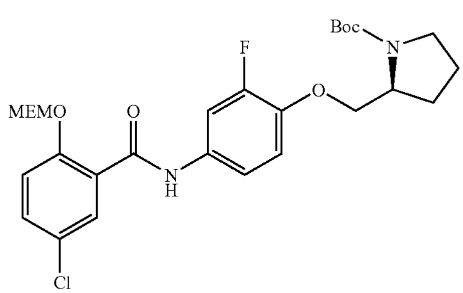 | Yield: 68%<br>¹H-NMR (CDCl₃) δ: 1.47 (9H, s), 1.80-2.19 (4H, m), 3.33 (3H, s), 3.34-3.46 (2H, m), 3.54-3.60 (2H, m), 3.87-3.93 (2H, m), 4.02-4.26 (3H, m), 5.48 (2H, s), 6.91-7.10 (1H, m), 7.18 (1H, d, J = 8.7 Hz), 7.25-7.34 (1H, m), 7.41 (1H, dd, J = 8.7, 2.7 Hz), 7.51-7.74 (1H, m), 8.18 (1H, d, J = 2.7 Hz), 9.61 (1H, s). |

TABLE 14-continued

| Reference Example | Structure | NMR |
|---|---|---|
| 154 | (structure) | Yield: 65%<br>¹H-NMR (CDCl₃) δ: 1.39-1.53 (1H, m), 1.46 (9H, s), 1.57-1.63 (2H, m), 1.75-1.85 (2H, m), 2.60-2.71 (2H, m), 3.03-3.14 (2H, m), 3.33 (3H, s), 3.39-3.47 (2H, m), 3.54-3.59 (2H, m), 3.87-3.92 (2H, m), 4.66 (1H, brs), 5.47 (2H, s), 6.94 (1H, t, J = 9.3 Hz), 7.18 (1H, d, J = 8.7 Hz), 7.27 (1H, dd, J = 8.7, 1.5 Hz), 7.40 (1H, dd, J = 9.0, 3.0 Hz), 7.52 (1H, dd, J = 13.8, 2.7 Hz), 8.18 (1H, d, J = 2.7 Hz), 9.60 (1H, s). |
| 155 | (structure) | Yield: 97%<br>¹H-NMR (DMSO-d₆) δ: 1.37-1.54 (1H, m), 1.54-1.69 (1H, m), 1.69-1.80 (1H, m), 1.80-1.91 (1H, m), 2.43-2.63 (2H, m), 2.63-2.73 (1H, m), 3.19 (3H, s), 3.24-3.35 (2H, m), 3.41-3.46 (2H, m), 3.72-3.77 (2H, m), 5.35 (2H, s), 6.83 (1H, brs), 7.04 (1H, t, J = 9.0 Hz), 7.29 (1H, d, J = 8.7 Hz), 7.35 (1H, brs), 7.36 (1H, d, J = 8.4 Hz), 7.52 (1H, dd, J = 8.7, 2.4 Hz), 7.58 (1H, d, J = 3.0 Hz), 7.62 (1H, dd, J = 15.0, 2.4 Hz), 10.24 (1H, s). |
| 156 | (structure) | Yield: Quantitative<br>¹H-NMR (CDCl₃) δ: 1.36-1.73 (13H, m), 1.89-2.07 (2H, m), 2.92 (2H, brs), 3.30-3.36 (2H, m), 3.56-3.59 (2H, m), 3.58-3.91 (5H, m), 4.02-4.18 (1H, m), 5.48 (2H, s), 6.93 (1H, t, J = 9.0 Hz), 7.17 (1H, d, J = 9.0 Hz), 7.27-7.31 (1H, m), 7.34-7.43 (1H, m), 7.56 (1H, dd, J = 12.6, 2.7 Hz), 8.18-8.20 (1H, m), 9.62 (1H, brs). |
| 157 | (structure) | Yield Quantitative<br>¹H-NMR (CDCl₃) δ: 1.17-1.22 (2H, m), 1.84-2.18 (5H, m), 2.72-3.92 (14H, m), 5.34 (2H, s), 7.17-7.43 (5H, m), 7.68 (1H, dd, J = 13.2, 2.4 Hz), 8.15 (1H, d, J = 2.7 Hz). |
| 158 | (structure) | Yield: Quantitative<br>¹H-NMR (CDCl₃) δ: 1.49-1.94 (2H, m), 2.74-3.81 (19H, m), 5.33 (2H, s), 7.20-7.41 (7H, m). |

TABLE 14-continued

| Reference Example | Structure | NMR |
|---|---|---|
| 159 | 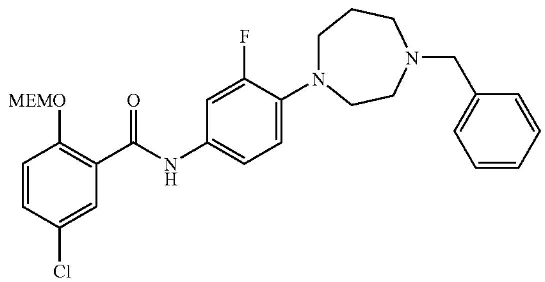 | Yield: 97%<br>¹H-NMR (CDCl₃) δ: 1.93-2.00 (2H, m), 2.70-2.82 (4H, m), 3.31 (3H, s), 3.38-3.40 (4H, m), 3.53-3.56 (2H, m), 3.67 (2H, s), 3.86-3.89 (2H, m), 5.44 (2H, s), 6.80 (1H, t, J = 8.7 Hz), 7.12-7.36 (8H, m), 7.52 (1H, dd, J = 15.0, 2.7 Hz), 8.13 (1H, d, J = 2.7 Hz), 9.56 (1H, s). |
| 160 | 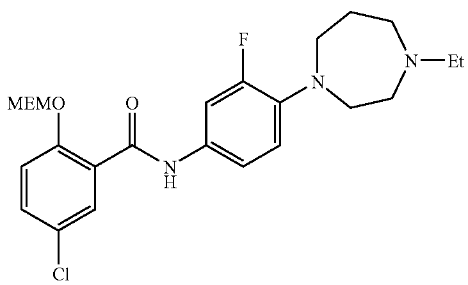 | Yield: 96%<br>¹H-NMR (CDCl₃) δ: 1.23-1.28 (3H, m), 2.03 (2H, brs), 2.68 (2H, q, J = 7.2 Hz), 2.79-2.92 (4H, m), 3.33-3.58 (9H, m), 3.88-3.91 (2H, m), 5.46 (2H, s), 6.82 (1H, t, J = 9.0 Hz), 7.15-7.19 (2H, m), 7.35-7.39 (1H, m), 7.51-7.57 (1H, m), 8.13 (1H, d, J = 3.0 Hz), 9.58 (1H, s). |
| 161 | 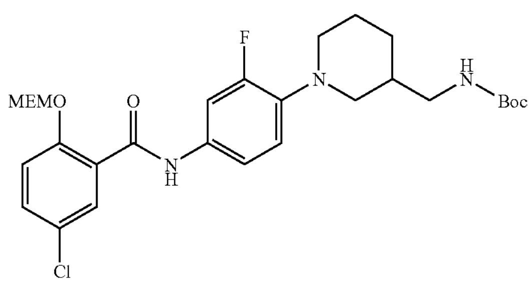 | Yield: 86%<br>¹H-NMR (CDCl₃) δ: 1.10-1.24 (1H, m), 1.45 (9H, s), 1.70-1.86 (3H, m), 1.86-1.99 (1H, m), 2.46-2.54 (1H, m), 2.63-2.74 (1H, m), 3.13 (2H, t, J = 6.3 Hz), 3.22-3.37 (2H, m), 3.34 (3H, s), 3.55-3.59 (2H, m), 3.88-3.92 (2H, m), 4.65 (1H, brs), 5.48 (2H, s), 6.93 (1H, t, J = 9.0 Hz), 7.18 (1H, d, J = 9.0 Hz), 7.23-7.29 (1H, m), 7.40 (1H, dd, J = 9.0, 2.7 Hz), 7.53 (1H, dd, J = 13.8, 2.4 Hz), 8.19 (1H, d, J = 2.7 Hz), 9.61 (1H, s). |
| 162 | 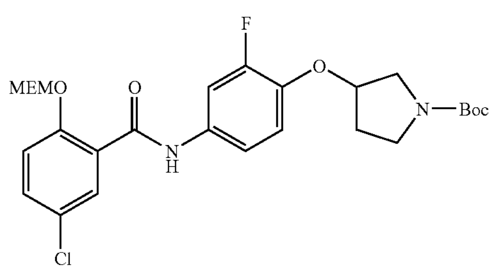 | Yield: 75%<br>¹H-NMR (CDCl₃) δ: 1.48 (9H, s), 2.06 (1H, brs), 2.19 (1H, brs), 3.33 (3H, s), 3.48-3.72 (6H, m), 3.88-3.92 (2H, m), 4.88 (1H, brs), 5.48 (2H, s), 6.94 (1H, t, J = 9.0 Hz), 7.18 (1H, d, J = 8.7 Hz), 7.23-7.35 (1H, m), 7.41 (1H, dd, J = 9.0, 2.7 Hz), 7.55-7.68 (1H, m), 8.18 (1H, d, J = 2.7 Hz), 9.65 (1H, s). |
| 163 | 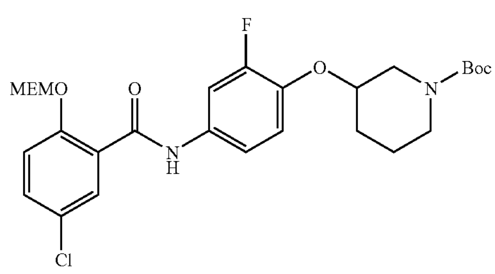 | Yield Quantitative<br>¹H-NMR (CDCl₃) δ: 1.44 (9H, s), 1.79-2.06 (6H, m), 3.18-3.40 (5H, m), 3.58-3.62 (2H, m), 3.89-3.93 (2H, m), 4.15-4.21 (1H, m), 5.48 (2H, s), 7.00-7.08 (1H, m), 7.17-7.30 (2H, m), 7.41 (1H, dd, J = 9.0, 2.7 Hz), 7.59-7.68 (1H, m), 8.18 (1H, d, J = 2.7 Hz), 9.64 (1H, brs). |

TABLE 14-continued

| Reference Example | Structure | NMR |
|---|---|---|
| 164 | 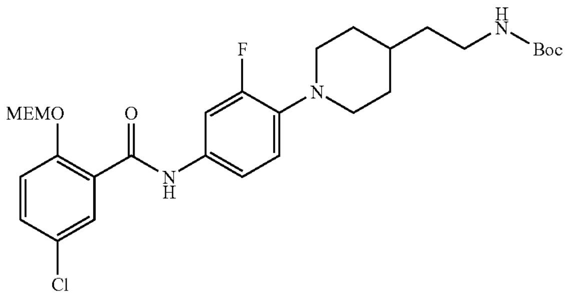 | Yield 96%<br>¹H-NMR (CDCl₃) δ: 1.38-1.56 (5H, m), 1.45 (9H, s), 1.73-1.87 (2H, m), 2.57-2.70 (2H, m), 3.12-3.26 (2H, m), 3.33 (3H, s), 3.37-3.43 (2H, m), 3.54-3.59 (2H, m), 3.87-3.92 (2H, m), 4.50 (1H, brs), 5.47 (2H, s), 6.93 (1H, t, J = 9.0 Hz), 7.17 (1H, d, J = 8.7 Hz), 7.25-7.31 (1H, m), 7.40 (1H, dd, J = 9.0, 2.7 Hz), 7.51 (1H, dd, J = 14.1, 2.4 Hz), 8.17 (1H, d, J = 2.7 Hz), 9.60 (1H, s). |
| 165 | 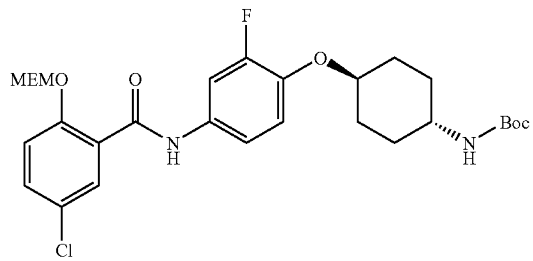 | Yield: 88%<br>¹H-NMR (CDCl₃) δ: 1.15-1.29 (2H, m), 1.45 (9H, s), 1.56-1.69 (2H, m), 2.06-2.16 (4H, m), 3.33 (3H, s), 3.50-3.59 (3H, m), 3.88-3.91 (2H, m), 4.06-4.16 (1H, m), 4.39 (1H, brs), 5.48 (2H, s), 6.97 (1H, t, J = 9.0 Hz), 7.18 (1H, d, J = 9.0 Hz), 7.26-7.29 (1H, m), 7.41 (1H, dd, J = 9.0, 2.7 Hz), 7.56 (1H, dd, J = 12.6, 2.7 Hz), 8.18 (1H, d, J = 2.7 Hz), 9.62 (1H, brs). |
| 166 | 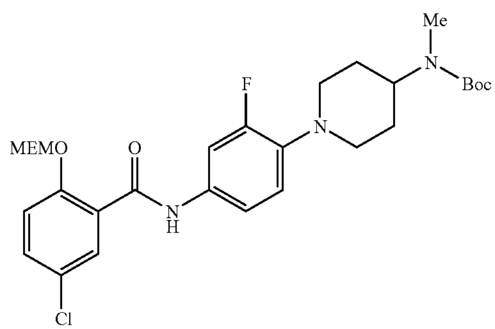 | Yield: Quantitative<br>¹H-NMR (CDCl₃) δ: 1.48 (9H, s), 1.73-2.17 (4H, m), 2.72-2.79 (5H, m), 3.34 (3H, s), 3.45-3.59 (4H, m), 3.88-3.91 (2H, m), 4.01-4.13 (1H, m), 5.48 (2H, s), 6.94 (1H, t, J = 9.0 Hz), 7.18 (1H, d, J = 9.0 Hz), 7.24-7.26 (1H, m), 7.40 (1H, dd, J = 9.0, 3.0 Hz), 7.53-7.58 (1H, m), 8.18 (1H, d, J = 2.7 Hz), 9.62 (1H, s). |
| 167 | 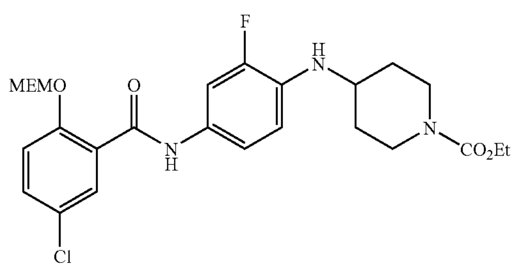 | Yield: 85%<br>¹H-NMR (CDCl₃) δ: 1.27 (3H, t, J = 6.9 Hz), 1.31-1.46 (2H, m), 2.00-2.12 (2H, m), 2.93-3.07 (2H, m), 3.34 (3H, s), 3.37-3.50 (1H, m), 3.54-3.59 (2H, m), 3.71 (1H, brs), 3.86-3.92 (2H, m), 4.08 (2H, brs), 4.14 (2H, q, J = 6.6 Hz), 5.47 (2H, s), 6.69 (1H, t, J = 9.0 Hz), 7.13-7.22 (2H, m), 7.39 (1H, dd, J = 8.7, 2.7 Hz), 7.50 (1H, dd, J = 12.9, 2.4 Hz), 8.18 (1H, d, J = 2.7 Hz), 9.51 (1H, s). |
| 168 | 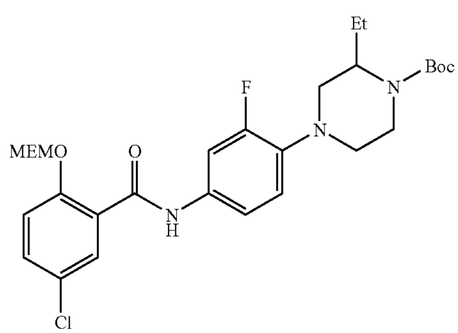 | Yield: Quantitative<br>¹H-NMR (CDCl₃) δ: 0.94 (3H, t, J = 7.4 Hz), 1.48 (9H, s), 1.76-1.96 (2H, m), 2.74-2.79 (2H, m), 3.20-3.28 (3H, m), 3.34 (3H, s), 3.55-3.58 (2H, m), 3.88-3.91 (2H, m), 4.04 (2H, brs), 5.48 (2H, s), 6.88 (1H, t, J = 9.0 Hz), 7.16-7.19 (1H, m), 7.24-7.26 (1H, m), 7.39-7.43 (1H, m), 7.65 (1H, dd, J = 9.0, 2.7 Hz), 8.19 (1H, d, J = 2.7 Hz), 9.63 (1H, s). |

TABLE 14-continued

| Reference Example | Structure | NMR |
|---|---|---|
| 169 | 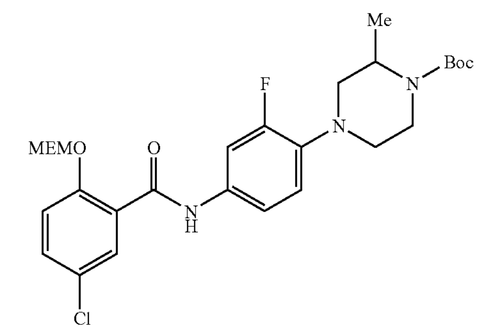 | Yield: 93%<br>¹H-NMR (CDCl₃) δ: 1.36 (3H, d, J = 6.8 Hz), 1.49 (9H, s), 2.69-2.85 (2H, m), 3.18-3.27 (3H, m), 3.34 (3H, s), 3.56-3.58 (2H, m), 3.88-3.91 (2H, m), 3.92-3.98 (1H, m), 4.32 (1H, brs), 5.48 (2H, s), 6.88 (1H, t, J = 9.0 Hz), 7.16-7.19 (1H, m), 7.24-7.27 (1H, m), 7.39-7.43 (1H, m), 7.54-7.59 (1H, m), 8.19 (1H, d, J = 2.8 Hz), 9.63 (1H, s). |
| 170 | 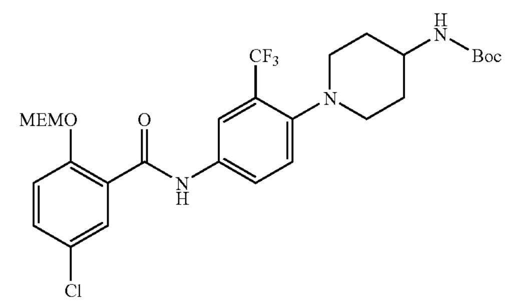 | Yield: 82%<br>¹H-NMR (CDCl₃) δ: 1.46 (9H, s), 1.54-1.65 (2H, m), 1.99-2.02 (2H, m), 2.76-2.83 (2H, m), 2.99-3.03 (3H, m), 3.32 (3H, s), 3.56-3.59 (2H, m), 3.89-3.92 (2H, m), 4.51 (1H, brs), 5.49 (2H, s), 7.19 (1H, d, J = 9.0 Hz), 7.34-7.37 (1H, m), 7.42 (1H, dd, J = 9.0, 2.7 Hz), 7.77 (1H, brs), 7.90-7.93 (1H, m), 8.18 (1H, d, J = 2.7 Hz), 9.73 (1H, s). |
| 171 | 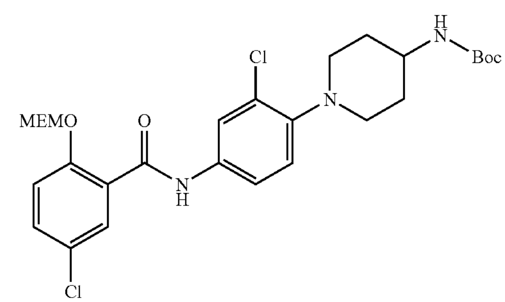 | Yield: 94%<br>¹H-NMR (CDCl₃) δ: 1.47 (9H, s), 1.59-1.68 (2H, m), 2.04-2.07 (2H, m), 2.71-2.78 (2H, m), 3.28-3.32 (3H, m), 3.34 (3H, s), 3.56-3.59 (2H, m), 3.88-3.91 (2H, m), 4.51 (1H, brs), 5.48 (2H, s), 7.03 (1H, d, J = 8.8 Hz), 7.18 (1H, d, J = 8.8 Hz), 7.40 (1H, dd, J = 8.8, 2.7 Hz), 7.52-7.55 (1H, m), 7.69-7.70 (1H, m), 8.18 (1H, d, J = 2.7 Hz), 9.60 (1H, s). |
| 172 | 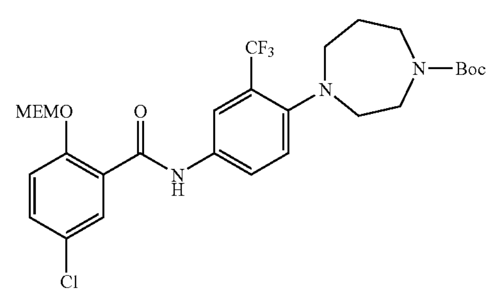 | Yield: 57%<br>¹H-NMR (CDCl₃) δ: 1.49 (9H, s), 1.87-1.93 (2H, m), 3.04 (4H, brs), 3.33 (3H, s), 3.53-3.61 (6H, m), 3.89-3.92 (2H, m), 5.49 (2H, s), 7.17-7.21 (1H, m), 7.31-7.34 (1H, m), 7.41-7.45 (1H, m), 7.74-7.77 (1H, m), 7.91-7.94 (1H, m), 8.18 (1H, d, J = 2.7 Hz), 9.74 (1H, s). |
| 173 | 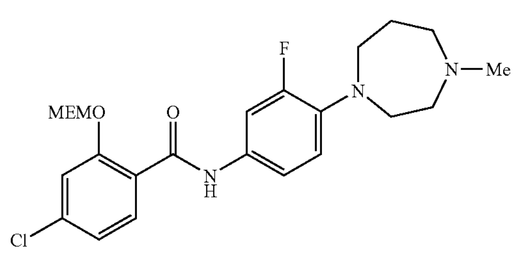 | Yield: 56%<br>¹H-NMR (CDCl₃) δ: 2.40 (3H, s), 2.65-2.78 (4H, m), 3.38-3.46 (9H, m), 3.57-3.61 (2H, m), 3.90-3.93 (2H, m), 5.48 (2H, s), 6.79-6.86 (1H, m), 7.13-7.30 (3H, m), 7.48-7.53 (1H, m), 8.16 (1H, d, J = 8.4 Hz), 9.50 (1H, s). |

TABLE 14-continued

| Reference Example | Structure | NMR |
|---|---|---|
| 174 | 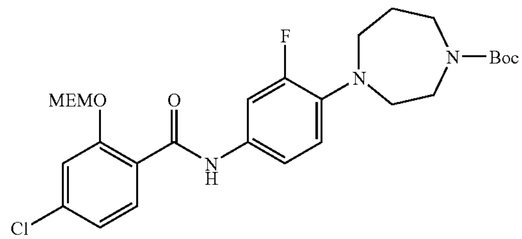 | Yield Quantitative<br>$^1$H-NMR(CDCl$_3$) δ: 1.42-1.46 (9H, m), 1.93-1.98 (2H, m), 3.31-3.50 (9H, m), 3.56-3.59 (4H, m), 3.89-3.92 (2H, m), 5.47 (2H, s), 6.83 (1H, t, J = 9.0 Hz), 7.08 (1H, dd, J = 9.0, 2.1 Hz), 7.16-7.22 (2H, m), 7.56 (1H, d, J = 14.7 Hz), 8.06 (1H, d, J = 9.0 Hz), 9.55 (1H, brs). |
| 175 | 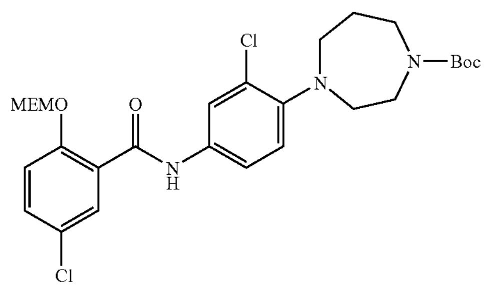 | Yield: 74%<br>$^1$H-NMR (CDCl$_3$) δ: 1.49 (9H, s), 2.00-2.06 (2H, m), 3.12-3.22 (4H, m), 3.35 (3H, s), 3.56-3.64 (6H, m), 3.89-3.92 (2H, m), 5.49 (2H, s), 7.06-7.09 (1H, m), 7.18-7.21 (1H, m), 7.40-7.44 (1H, m), 7.48-7.58 (1H, m), 7.67-7.71 (1H, m), 8.19 (1H, d, J = 2.7 Hz), 9.61 (1H, brs). |
| 176 | 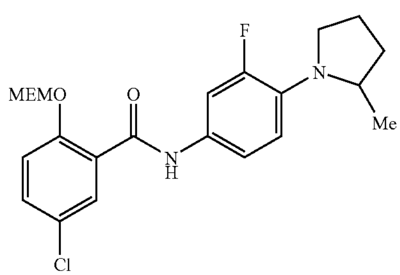 | Yield: 77%<br>$^1$H-NMR (CDCl$_3$) δ: 1.10 (3H, d, J = 6.0 Hz), 1.51-1.70 (1H, m), 1.78-2.22 (3H, m), 3.11-3.24 (1H, m), 3.34 (3H, s), 3.50-3.66 (3H, m), 3.81-4.05 (3H, m), 5.47 (2H, s), 6.70 (1H, t, J = 9.3 Hz), 7.12-7.29 (2H, m), 7.39 (1H, dd, J = 9.0, 3.0 Hz), 7.48 (1H, dd, J = 15.3, 2.4 Hz), 8.20 (1H, d, J = 3.0 Hz), 9.52 (1H, s). |
| 177(a) | 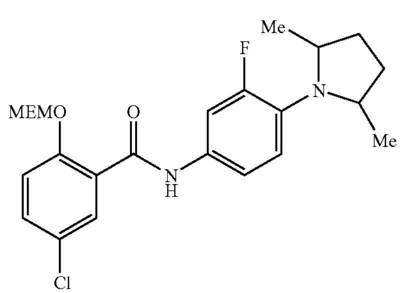 | This compound was isolated as a single diastereomer.<br>Yield: 35%<br>$^1$H-NMR (CDCl$_3$) δ: 1.18 (6H, d, J = 6.0 Hz), 1.55-1.74 (2H, m), 1.90-2.10 (2H, m), 3.33 (3H, s), 3.50-3.70 (4H, m), 3.83-3.94 (2H, m), 5.46 (2H, s), 6.86 (1H, t, J = 9.0 Hz), 7.16 (1H, d, J = 8.7 Hz), 7.18-7.28 (1H, m), 7.37 (1H, dd, J = 8.7, 2.7 Hz), 7.52 (1H, dd, J = 14.7, 2.4 Hz), 8.16 (1H, d, J = 2.7 Hz), 9.58 (1H, s). |
| 177(b) | 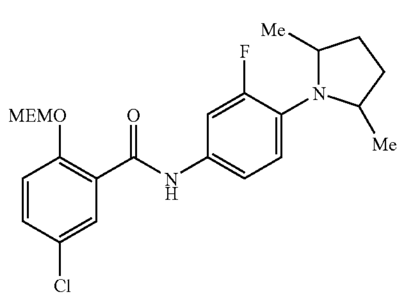 | This compound was a diastereomeric isomer of the compound of Reference Example 177(a).<br>Yield: 5%<br>$^1$H-NMR (CDCl$_3$) δ: 1.01 (6H, d, J = 6.3 Hz), 1.44-1.65 (2H, m), 2.10-2.28 (2H, m), 3.34 (3H, s), 3.52-3.62 (2H, m), 3.84-3.93 (2H, m), 3.98-4.14 (2H, m), 5.47 (2H, s), 6.76 (1H, t, J = 9.0 Hz), 7.18 (1H, d, J = 9.0 Hz), 7.20-7.29 (1H, m), 7.39 (1H, dd, J = 9.0, 2.7 Hz), 7.47 (1H, dd, J = 14.7, 2.4 Hz), 8.19 (1H, d, J = 2.7 Hz), 9.54 (1H, s). |

TABLE 14-continued

| Reference Example | Structure | NMR |
|---|---|---|
| 178 | 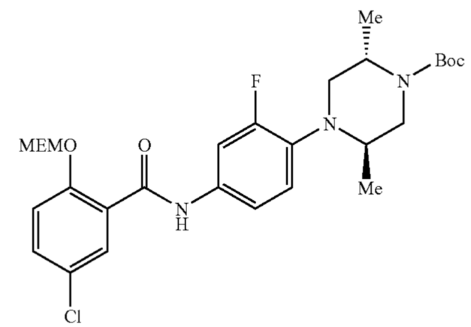 | Yield 79%<br>$^1$H-NMR (CDCl$_3$) δ: 0.97 (3H, d, J = 6.0 Hz), 1.30 (3H, d, J = 6.5 Hz), 1.48 (9H, s), 2.74 (1H, d, J = 11.5 Hz), 3.33 (3H, s), 3.48 (2H, td, J = 11.0, 3.5 Hz), 3.56-3.58 (2H, m), 3.68-3.80 (2H, m), 3.88-3.91 (2H, m), 4.41 (1H, brs), 5.47 (2H, s), 6.80 (1H, t, J = 9.0 Hz), 7.18 (1H, d, J = 9.0 Hz), 7.24 (1H, dd, J = 9.0, 2.0 Hz), 7.40 (1H, dd, J = 9.0, 2.5 Hz), 7.54 (1H, dd, J = 14.0, 2.0 Hz), 8.18 (1H, d, J = 2.5 Hz), 9.61 (1H, s). |
| 179 | 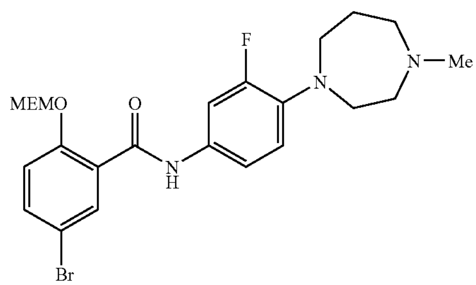 | Yield: 63%<br>$^1$H-NMR (CDCl$_3$) δ: 1.96-2.03 (2H, m), 2.40 (3H, s), 2.66-2.78 (8H, m), 3.24-3.58 (5H, m), 3.88-3.91 (2H, m), 5.47 (2H, s), 6.37-6.44 (1H, m), 6.59-6.88 (1H, m), 7.10-7.25 (2H, m), 7.50-7.58 (1H, m), 8.32 (1H, d, J = 2.7 Hz), 9.52 (1H, brs). |
| 180 | 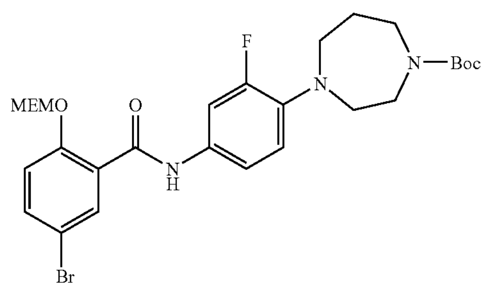 | Yield: 95%<br>$^1$H-NMR (CDCl$_3$) δ: 1.43-1.46 (9H, m), 1.92-2.00 (2H, m), 3.33 (3H, s), 3.34-3.59 (10H, m), 3.88-3.91 (2H, m), 5.47 (2H, s), 6.86 (1H, t, J = 9.0 Hz), 7.12 (1H, d, J = 9.0 Hz), 7.17-7.21 (1H, m), 7.50-7.55 (2H, m), 8.31 (1H, d, J = 2.7 Hz), 9.56 (1H, brs). |
| 181 | 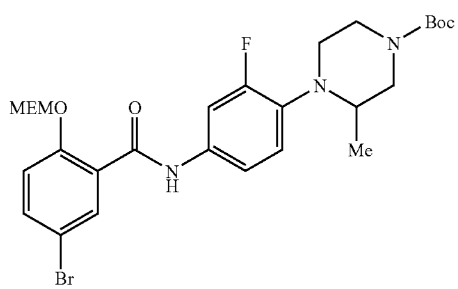 | Yield: 45%<br>$^1$H-NMR (CDCl$_3$) δ: 0.92 (3H, d, J = 6.4 Hz), 1.49 (9H, s), 2.85-2.88 (1H, m), 3.12 (1H, brs), 3.33 (3H, s), 3.36-3.61 (7H, m), 3.88-3.92 (2H, m), 5.48 (2H, s), 7.00 (1H, t, J = 9.0 Hz), 7.16-7.19 (1H, m), 7.28 (1H, brs), 7.41 (1H, dd, J = 9.0, 2.7 Hz), 7.54-7.60 (1H, m), 8.18 (1H, d, J = 2.7 Hz), 9.67 (1H, brs). |
| 182 | 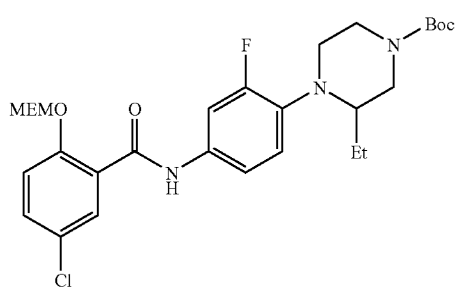 | Yield: 38%<br>$^1$H-NMR (CDCl$_3$) δ: 0.83 (3H, t, J = 7.4 Hz), 1.32 (2H, brs), 1.49 (9H, s), 2.86-2.91 (1H, m), 3.23-3.27 (1H, m), 3.33 (3H, s), 3.51-3.91 (9H, m), 5.48 (2H, s), 6.94 (1H, brs), 7.15-7.28 (2H, m), 7.41 (1H, dd, J = 8.8, 2.7 Hz), 7.53-7.59 (1H, m), 8.18 (1H, d, J = 2.7 Hz), 9.64 (1H, brs). |

Reference Example 183

Preparation of {1-[4-(5-bromo-2-hydroxybenzoylamino)-2-fluorophenyl]piperidin-4-yl}carbamic acid tert-butyl ester

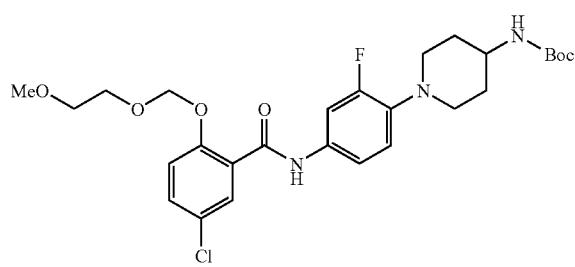

A mixture of 5-bromosalicylic acid (326 mg, 1.5 mmol), [1-(4-amino-2-fluorophenyl)piperidin-4-yl]carbamic acid tert-butyl ester (compound of Reference Example 90; 309 mg, 1.0 mmol), 1-ethyl-3-(3-dimethylaminopropyl)carbodiimide hydrochloride (287 mg, 1.5 mmol), 1-hydroxybenzotriazole (202 mg, 1.5 mmol), triethylamine (210% 1, 1.5 mmol) and N,N-dimethylformamide (5 ml) was stirred at room temperature for 3 hours. Saturated aqueous sodium hydrogen carbonate and water was added to the reaction mixture and the mixture was carried out ultrasound irradiation. The precipitated solid was collected by filtration and washed with water. The solid was suspended in methanol and carried out ultrasound irradiation. The solid was collected by filtration and dried under reduced pressure to give the title compound (224 mg, 47%) as a white solid.

$^1$H-NMR (DMSO-d$_6$) δ: 1.40 (9H, s), 1.46-1.62 (2H, m), 1.75-1.87 (2H, m), 2.61-2.75 (2H, m), 3.15-3.45 (3H, m), 6.87 (1H, d, J=6.6 Hz), 6.96 (1H, d, J=8.7 Hz), 7.04 (1H, t, J=9.3 Hz), 7.37 (1H, d, J=8.7 Hz), 7.54-7.66 (2H, m), 8.05 (1H, d, J=2.7 Hz), 10.39 (1H, s), 11.83 (1H, brs).

The compound described in Reference Example 184 was obtained in the same manner as the method of Reference Example 183, except that 4-chlorosalicylic acid was used instead of 5-bromosalicylic acid.

Reference Example 185

Preparation of N-(4-bromo-3-fluorophenyl)-5-chloro-2-hydroxybenzamide

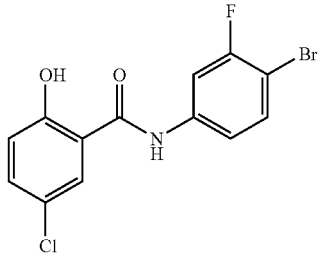

4-Bromo-3-fluoroaniline (0.570 g, 3.00 mmol) and phosphorus trichloride (0.176 ml, 2.0 mmol) were added to a solution of 5-chlorosalicylic acid (0.690 g, 4.00 mmol) in toluene (30 ml), and the mixture was refluxed for 2 hours. Saturated aqueous sodium hydrogencarbonate was added to the reaction mixture, and the mixture was concentrated under reduced pressure and extracted with tetrahydrofuran. The organic layer was washed with saturated aqueous sodium hydrogencarbonate and dried over anhydrous sodium sulfate. The solvent was evaporated under reduced pressure to give the title compound (0.930 g, 90%) as a white solid.

$^1$H-NMR (DMSO-d$_6$) δ: 6.83 (1H, d, J=9.0 Hz), 7.27 (1H, dd, J=9.0, 3.0 Hz), 7.35 (1H, dd, J=9.3, 2.4 Hz), 7.64 (1H, t, J=8.1 Hz), 7.77 (1H, d, J=3.0 Hz), 7.93 (1H, dd, J=12.0, 2.4 Hz), 12.57 (2H, brs).

Reference Example 186

Preparation of 5-chloro-N-[3-fluoro-4-(pyridin-4-yl)phenyl]-2-hydroxybenzamide

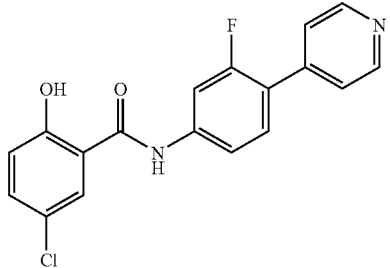

TABLE 15

| Reference Example | Structure | NMR |
|---|---|---|
| 184 | ![structure] | Yield: 32%<br>$^1$H-NMR (DMSO-d$_6$) δ: 1.40 (9H, s), 1.42-1.64 (2H, m), 1.74-1.89 (2H, m), 2.60-2.77 (2H, m), 3.16-3.44 (3H, m), 6.8 1-6.94 (1H, m), 6.98-7.14 (2H, m), 7.32-7.43 (1H, m), 7.55-7.69 (1H, m), 7.91 (1H, d, J = 9.1 Hz), 10.3 (1H, s), 12.0 (1H, brs). |

4-Pyridineboronic acid (0.185 mg, 1.51 mmol), potassium carbonate (0.240 g, 1.74 mmol), [1,1'-bis(diphenylphosphino)ferrocene]dichloropalladium(II), complex with dichloromethane (1:1) (0.189 g, 0.232 mmol) and water (0.5 ml) were added to a solution of N-(4-bromo-3-fluorophenyl)-5-chloro-2-hydroxybenzamide (compound of Reference Example 185; 0.400 g, 1.16 mmol) in dioxane (5 ml), and the mixture was stirred at 80° C. for 2 hours. Water was added to the reaction mixture, and the precipitated solid was collected by filtration and washed with acetone and dichloromethane to give the title compound (0.286 g, 72%) as a light grey solid.

$^{1}$H-NMR (DMSO-$d_6$) δ: 7.10 (1H, d, J=8.7 Hz), 7.49 (1H, dd, J=9.0, 2.7 Hz), 7.73 (1H, dd, J=8.4, 1.5 Hz), 7.85-7.93 (2H, m), 7.98 (1H, d, J=14.1 Hz), 8.19 (2H, d, J=6.0 Hz), 8.94 (2H, d, J=6.6 Hz), 10.80 (1H, s), 11.62 (1H, brs).

Reference Example 187

Preparation of 5-(trifluoromethyl)salicylic acid

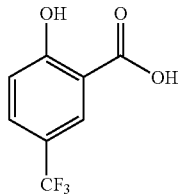

This compound was obtained in the same manner as the method described in the following document.

Chem. Pharm. Bull., vol. 44, No. 4, pp. 734-745 (1996).

Reference Example 188

Preparation of 5-cyanosalicylic acid

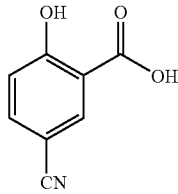

This compound was obtained in the same manner as the method described in the following document.

EP 1510207 A1, pp. 124-125

Example 1

Preparation of 5-chloro-N-(3-fluoro-4-morpholinophenyl)-2-hydroxybenzamide (Compound No. 1)

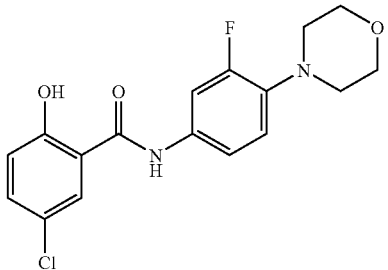

A mixture of 5-chlorosalicylic acid (0.30 g, 1.738 mmol), 3-fluoro-4-morpholinoaniline (compound of Reference Example 74; 0.34 g, 1.738 mmol), phosphorus trichloride (0.08 ml, 0.869 mmol) and toluene (6 ml) was refluxed for 1.5 hours. The reaction mixture was cooled to the room temperature, and extracted with ethyl acetate after addition of water. The ethyl acetate layer was washed with water and saturated brine, and dried over anhydrous sodium sulfate. The residue obtained by evaporation of the solvent under reduced pressure was washed with diisopropyl ether to give the title compound (0.30 g, 49%) as a colorless crystal.

$^{1}$H-NMR (DMSO-$d_6$) δ: 2.98 (4H, t, J=4.5 Hz), 3.74 (4H, t, J=4.5 Hz), 7.02 (1H, d, J=9.0 Hz), 7.05 (1H, t, J=9.0 Hz), 7.40 (1H, dd, J=9.0, 2.0 Hz), 7.45 (1H, dd, J=9.0, 2.5 Hz), 7.64 (1H, dd, J=15.0, 2.0 Hz), 7.91 (1H, d, J=2.5 Hz), 10.49 (1H, brs), 11.83 (1H, brs).

The compounds described in Examples 2 to 39 were obtained in the same manner as the method of Example 1, by reacting the appropriate aniline derivative with the carboxylic acid derivative.

TABLE 16

| Example | NMR |
|---|---|
| 2 (Compound No. 2) | $^{1}$H-NMR (DMSO-$d_6$) δ: 1.45-1.55 (2H, m), 1.60-1.70 (4H, m), 2.85-3.00 (4H, m), 6.98 (1H, d, J = 9.0 Hz), 7.04 (1H, t, J = 9.0 Hz), 7.40 (1H, dd, J = 9.0, 2.0 Hz), 7.43 (1H, dd, J = 9.0, 2.5 Hz), 7.62 (1H, dd, J = 15.0, 2.0 Hz), 7.91 (1H, d, J = 2.5 Hz), 10.65 (1H, brs), 11.80 (1H, brs). |
| 3 (Compound No. 3) | $^{1}$H-NMR (DMSO-$d_6$) δ: 2.84 (4H, t, J = 5.0 Hz), 3.71 (4H, t, J = 4.5 Hz), 7.00 (1H, d, J = 9.0 Hz), 7.45 (1H, dd, J = 9.0, 3.0 Hz), 7.61 (1H, d, J = 8.5 Hz), 7.90 (1H, d, J = 2.5 Hz), 7.93 (1H, dd, J = 8.5, 2.0 Hz), 8.11 (1H, d, J = 3.0 Hz), 10.85 (1H, brs), 11.50 (1H, brs). |
| 4 (Compound No. 4) | Yield: 51% $^{1}$H-NMR (DMSO-$d_6$) δ: 1.45-1.57 (2H, m), 1.57-1.68 (4H, m), 2.74-2.84 (4H, m), 7.01 (1H, d, J = 8.7 Hz), 7.47 (1H, dd, J = 9.0, 2.7 Hz), 7.54 (1H, d, J = 8.7 Hz), 7.88-7.96 (2H, m), 8.08 (1H, d, J = 2.4 Hz), 10.60 (1H, brs), 11.69 (1H, brs). |

TABLE 16-continued

| Example | NMR |
|---|---|
| 5 (Compound No. 5) | Yield: 62%<br>$^1$H-NMR (DMSO-$d_6$) δ: 1.26-1.60 (6H, m), 1.63-1.76 (2H, m), 1.81-1.93 (2H, m), 4.53-4.63 (1H, m), 7.00 (1H, d, J = 8.7 Hz), 7.32 (1H, d, J = 9.3 Hz), 7.17 (1H, dd, J = 9.0, 2.7 Hz), 7.85 (1H, dd, J = 9.0, 2.4 Hz), 7.95 (1H, d, J = 2.7 Hz), 8.02 (1H, d, J = 2.4 Hz), 10.53 (1H, s), 11.77 (1H, brs). |
| 6 (Compound No. 6) | Yield: 67%<br>$^1$H-NMR (DMSO-$d_6$) δ: 1.86-1.93 (4H, m), 3.25-3.36 (4H, m), 6.74 (1H, dd, J = 9.9, 9.0 Hz), 7.00 (1H, d, J = 8.7 Hz), 7.29 (1H, dd, J = 8.7, 2.1 Hz), 7.46 (1H, dd, J = 8.7, 2.7 Hz), 7.56 (1H, dd, J = 15.9, 2.7 Hz), 7.97 (1H, d, J = 3.0 Hz), 10.30 (1H, s), 11.98 (1H, brs). |
| 7 (Compound No. 7) | Yield: 52%<br>$^1$H-NMR (DMSO-$d_6$) δ: 1.52-1.60 (4H, m), 1.69-1.82 (4H, m), 3.26-3.36 (4H, m), 6.91 (1H, dd, J = 9.9, 9.3 Hz), 7.00 (1H, d, J = 8.7 Hz), 7.29 (1H, dd, J = 9.0, 2.7 Hz), 7.46 (1H, dd, J = 8.7, 2.7 Hz), 7.56 (1H, dd, J = 16.2, 2.4 Hz), 7.96 (1H, d, J = 2.4 Hz), 10.32 (1H, s), 11.94 (1H, brs). |
| 8 (Compound No. 8) | Yield: 66%<br>$^1$H-NMR (DMSO-$d_6$) δ: 1.48-1.59 (2H, m), 1.60-1.72 (4H, m), 2.85-2.93 (4H, m), 7.01 (1H, d, J = 9.0 Hz), 7.15 (1H, d, J = 8.7 Hz), 7.47 (1H, dd, J = 8.7, 2.7 Hz), 7.56 (1H, dd, J = 8.4, 2.4 Hz), 7.86 (1H, d, J = 2.4 Hz), 7.93 (1H, d, J = 2.7 Hz), 10.39 (1H, s), 11.78 (1H, brs). |
| 9 (Compound No. 9) | Yield: 30%<br>$^1$H-NMR (DMSO-$d_6$) δ: 1.47-1.58 (2H, m), 1.59-1.71 (4H, m), 2.25 (3H, s), 2.73-2.82 (4H, m), 6.98-7.02 (2H, m), 7.43-7.49 (3H, m), 8.00 (1H, d, J = 2.4 Hz), 10.28 (1H, s), 12.00 (1H, brs). |
| 10 (Compound No. 10) | Yield: 56%<br>$^1$H-NMR (DMSO-$d_6$) δ: 1.20-1.57 (6H, m), 1.65-1.78 (2H, m), 1.85-1.96 (2H, m), 4.25-4.36 (1H, m), 7.01 (1H, d, J = 8.7 Hz), 7.20 (1H, t, J = 9.3 Hz), 7.30-7.52 (2H, m), 7.67 (1H, dd, J = 13.5, 2.1 Hz), 7.92 (1H, d, J = 2.1 Hz), 10.39 (1H, s), 11.77 (1H, brs). |
| 11 (Compound No. 11) | Yield: 40%<br>$^1$H-NMR (DMSO-$d_6$) δ: 2.04 (3H, s), 2.90-3.03 (4H, m), 3.55-3.63 (4H, m), 6.98-7.12 (2H, m), 7.36-7.43 (1H, m), 7.43-7.50 (1H, m), 7.62-7.71 (1H, m), 7.92 (1H, d, J = 2.7 Hz), 10.44 (1H, s), 11.76 (1H, brs). |
| 12 (Compound No. 12) | Yield: 10%<br>$^1$H-NMR (DMSO-$d_6$) δ: 2.29 (3H, s), 2.48-2.52 (4H, m), 2.94-3.07 (4H, m), 6.94 (1H, d, J = 9.0 Hz), 7.04 (1H, t, J = 9.0 Hz), 7.20-7.40 (2H, m), 7.65 (1H, dd, J = 14.7, 2.4 Hz), 7.89 (1H, d, J = 2.7 Hz), 10.97 (2H, brs). |
| 13 (Compound No. 13) | Yield: 63%<br>$^1$H-NMR (DMSO-$d_6$) δ: 1.47-1.57 (2H, m), 1.57-1.70 (4H, m), 2.83-2.94 (4H, m), 3.79 (3H, s), 6.87 (1H, d, J = 8.4 Hz), 6.99 (1H, d, J = 8.7 Hz), 7.22 (1H, dd, J = 8.7, 2.4 Hz), 7.34 (1H, d, J = 2.4 Hz), 7.46 (1H, dd, J = 8.7, 2.4 Hz), 7.99 (1H, d, J = 2.4 Hz), 10.30 (1H, s), 12.02 (1H, s). |
| 14 (Compound No. 14) | Yield: 8%<br>$^1$H-NMR (DMSO-$d_6$) δ: 1.37 (3H, t, J = 6.9 Hz), 1.45-1.57 (2H, m), 1.57-1.72 (4H, m), 2.85-2.96 (4H, m), 4.01 (2H, q, J = 6.9 Hz), 6.86 (1H, d, J = 8.4 Hz), 7.00 (1H, d, J = 9.0 Hz), 7.19 (1H, dd, J = 8.4, 2.4 Hz), 7.33 (1H, d, J = 2.4 Hz), 7.46 (1H, dd, J = 9.0, 2.7 Hz), 7.99 (1H, d, J = 2.7 Hz), 10.28 (1H, s), 12.03 (1H, brs). |
| 15 (Compound No. 15) | Yield: 39%<br>$^1$H-NMR (DMSO-$d_6$) δ: 1.80-2.06 (6H, m), 2.09-2.20 (2H, m), 2.61-2.75 (2H, m), 2.98-3.14 (2H, m), 3.14-3.28 (1H, m), 3.38-3.58 (4H, m), 7.04 (1H, d, J = 8.7 Hz), 7.09-7.41 (2H, m), 7.47 (1H, dd, J = 8.7, 2.4 Hz), 7.66 (1H, dd, J = 14.7, 2.4 Hz), 7.94 (1H, d, J = 2.7 Hz), 10.45 (1H, s), 10.92 (1H, brs), 11.85 (1H, brs). |
| 16 (Compound No. 16) | This compound was obtained as a hydrochloride.<br>Yield: 7%<br>$^1$H-NMR (DMSO-$d_6$) δ: 2.81-2.87 (3H, m), 3.02-3.28 (4H, m), 3.35-3.43 (2H, m), 3.46-3.56 (2H, m), 7.05 (1H, d, J = 8.7 Hz), 7.25 (1H, d, J = 8.7 Hz), 7.47 (1H, dd, J = 8.7, 2.7 Hz), 7.63 (1H, dd, J = 9.0, 2.7 Hz), 7.93 (1H, d, J = 2.7 Hz), 7.94 (1H, d, J = 2.7 Hz), 10.47 (1H, s), 10.68 (1H, brs), 11.77 (1H, brs). |

TABLE 16-continued

| Example | NMR |
|---|---|
| 17 (Compound No. 17) | This compound was obtained as a hydrochloride. Yield: 47% $^1$H-NMR (DMSO-$d_6$) δ: 2.85 (3H, s), 3.00-3.55 (8H, m), 7.05 (1H, d, J = 3.3 Hz), 7.48 (1H, dd, J = 8.7, 2.1 Hz), 7.59 (1H, d, J = 8.7 Hz), 7.92 (1H, d, J = 2.7 Hz), 8.00 (1H, d, J = 8.7 Hz), 8.16 (1H, d, J = 2.1 Hz), 10.51 (1H, brs), 10.62 (1H, s), 11.66 (1H, brs). |
| 18 (Compound No. 18) | This compound was obtained as a hydrochloride. Yield: 48% $^1$H-NMR (DMSO-$d_6$) δ: 2.28 (3H, s), 2.78-2.85 (3H, m), 3.00-2.87 (6H, m), 3.41-3.51 (2H, m), 7.07 (2H, d, J = 8.7 Hz), 7.47 (1H, dd, J = 9.0, 2.7 Hz), 7.50-7.57 (2H, m), 8.00 (1H, d, J = 2.7 Hz), 10.37 (1H, s), 10.98 (1H, brs), 12.05 (1H, brs). |
| 19 (Compound No. 19) | Yield: 11% $^1$H-NMR (DMSO-$d_6$) δ: 1.32 (6H, d, J = 6.3 Hz), 3.11-3.29 (4H, m), 3.38-3.60 (4H, m), 5.44 (1H, brs), 7.05 (1H, d, J = 8.7 Hz), 7.13 (1H, t, J = 9.0 Hz), 7.47 (1H, dd, J = 8.7, 2.7 Hz), 7.45 (1H, dt, J = 9.0, 2.7 Hz), 7.71 (1H, dd, J = 14.4, 2.7 Hz), 7.93 (1H, d, J = 2.7 Hz), 10.47 (1H, s), 10.61 (1H, brs), 11.81 (1H, brs). |
| 20 (Compound No. 20) | Yield: 85% $^1$H-NMR (CD$_3$OD) δ: 1.41 (3H, t, J = 7.5 Hz), 3.10-3.32 (10H, m), 6.70 (1H, d, J = 9.0 Hz), 7.11 (1H, t, J = 9.0 Hz), 7.37 (1H, brs), 7.41 (1H, dd, J = 2.5 Hz), 7.67 (1H, dd, J = 9.0, 2.5 Hz), 7.97 (1H, d, J = 2.5 Hz). |
| 21 (Compound No. 21) | This compound was obtained as a dihydrochloride. Yield: Quantitative $^1$H-NMR (CD$_3$OD) δ: 1.29 (3H, t, J = 9.0 Hz), 2.33 (3H, s), 2.89 (2H, q, J = 7.5 Hz), 3.07 (8H, brs), 6.88 (1H, d, J = 9.0 Hz), 7.09 (1H, d, J = 9.0 Hz), 7.30 (1H, dd, J = 9.0, 3.0 Hz), 7.46-7.52 (2H, m), 7.91 (2H, s), 7.93 (1H, d, J = 3.0 Hz). |
| 22 (Compound No. 24) | Yield: 6% $^1$H-NMR (CD$_3$OD) δ: 1.80-1.93 (2H, m), 1.95-2.05 (2H, m), 2.35 (3H, s), 2.40-2.50 (2H, m), 2.75-2.85 (2H, m), 4.31-4.38 (1H, m), 6.71 (1H, d, J = 9.0 Hz), 7.07 (1H, t, J = 3.0 Hz), 7.12 (1H, dd, J = 9.0, 3.0 Hz) 7.22 (1H, ddd, J = 9.0, 3.0, 1.0 Hz), 7.72 (1H, dd, J = 13.0, 3.0 Hz), 7.82 (1H, d, J = 3.0 Hz). |
| 23 (Compound No. 25) | Yield: 16% $^1$H-NMR (CD$_3$OD) δ: 1.88-2.00 (2H, m), 2.02-2.13 (2H, m), 2.24 (3H, s), 2.49 (3H, s), 2.63-2.72 (2H, m), 2.86-2.95 (2H, m), 4.45-4.54 (1H, m), 6.87 (1H, d, J = 9.0 Hz), 6.93 (1H, d, J = 9.0 Hz), 7.30 (1H, dd, J = 9.0, 3.0 Hz), 7.42 (1H, s), 7.46 (1H, dd, J = 11.0, 2.5 Hz), 7.92 (1H, d, J = 3.0 Hz). |
| 24 (Compound No. 26) | Yield: 63% $^1$H-NMR (DMSO-$d_6$) δ: 2.72-2.78 (4H, m), 3.19-3.26 (4H, m), 7.01 (1H, d, J = 9.0 Hz), 7.09 (1H, t, J = 9.3 Hz), 7.25-7.35 (1H, m), 7.46 (1H, dd, J = 9.0, 2.7 Hz), 7.64 (1H, dd, J = 14.4, 2.7 Hz), 7.92 (1H, d, J = 3.0 Hz), 10.41 (1H, s), 11.77 (1H, s). |
| 25 (Compound No. 30) | Yield: 23% $^1$H-NMR (DMSO-$d_6$) δ: 2.83 (3H, brs), 3.02-3.30 (4H, m), 3.40-3.58 (4H, m), 6.93-7.02 (2H, m), 7.13 (1H, t, J = 9.0 Hz), 7.41-7.49 (2H, m), 7.72 (1H, dd, J = 14.7, 2.1 Hz), 7.92-7.98 (1H, m), 10.44 (1H, s), 10.63 (1H, brs), 11.73 (1H, s). |
| 26 (Compound No. 33) | Yield: 48% $^1$H-NMR (CD$_3$OD) δ: 1.14 (3H, t, J = 7.5 Hz), 2.46 (2H, q, J = 7.5 Hz), 3.03 (2H, t, J = 5.5 Hz), 3.08 (2H, t, J = 5.0 Hz), 3.70 (2H, t, J = 5.0 Hz), 3.75 (2H, t, J = 5.0 Hz), 6.95 (1H, d, J = 9.0 Hz), 7.04 (1H, t, J = 9.0 Hz), 7.33 (1H, dd, J = 9.0, 1.0 Hz), 7.40 (1H, dd, J = 9.0, 2.5 Hz), 7.62 (1H, dd, J = 15.0, 2.5 Hz), 7.96 (1H, d, J = 3.0 Hz). |
| 27 (Compound No. 34) | Yield: 33% $^1$H-NMR (CD$_3$OD) δ: 2.14 (2H, q, J = 6.0 Hz), 2.70 (3H, s), 3.14 (2H, t, J = 5.5 Hz), 3.18 (2H, t, J = 5.0 Hz), 3.37 (2H, t, J = 5.0 Hz), 3.45 (2H, t, J = 5.0 Hz), 6.81 (1H, d, J = 9.0 Hz), 6.97 (1H, t, J = 9.0 Hz), 7.23 (1H, dd, J = 9.0, 3.0 Hz), 7.21-7.25 (1H, m), 7.63 (1H, dd, J = 15.0, 2.5 Hz), 7.87 (1H, d, J = 3.0 Hz). |

TABLE 16-continued

| Example | NMR |
|---|---|
| 28 (Compound No. 35) | Yield: 21% $^1$H-NMR (CD$_3$OD) δ: 1.50-1.58 (2H, m), 1.64-1.73 (4H, m), 2.62-2.75 (6H, m), 2.86 (2H, t, J = 7.5 Hz), 3.01-3.10 (4H, m), 3.68 (2H, t, J = 5.0 Hz), 3.74 (2H, t, J = 5.0 Hz), 6.72 (1H, d, J = 9.0 Hz), 7.00 (1H, t, J = 9.0 Hz), 7.13 (1H, dd, J = 9.0, 3.0 Hz), 7.26 (1H, d, J = 9.0 Hz), 7.69 (1H, dd, J = 15.0, 2.5 Hz), 7.83 (1H, d, J = 3.0 Hz). |
| 29 (Compound No. 37) | Yield: 21% $^1$H-NMR (DMSO-d$_6$) δ: 1.38-1.59 (2H, m), 1.73-1.98 (2H, m), 2.26 (3H, s), 2.59-2.63 (2H, m), 2.91-2.94 (2H, m), 4.32-4.37 (1H, m), 6.93 (1H, t, J = 8.7 Hz), 7.22 (1H, t, J = 8.7 Hz), 7.34-7.41 (2H, m), 7.71 (1H, dd, J = 13.8, 2.7 Hz), 7.87 (1H, d, J = 2.7 Hz). |
| 30 (Compound No. 57) | Yield: 5% $^1$H-NMR (DMSO-d$_6$) δ: 2.28 (3H, s), 2.80-2.82 (3H, m), 3.10-3.23 (4H, m), 3.43-3.49 (4H, m), 6.90 (1H, d, J = 8.4 Hz), 7.12 (1H, t, J = 9.0 Hz), 7.20-7.26 (1H, m), 7.42-7.45 (1H, m), 7.72 (1H, dd, J = 14.7, 2.1 Hz), 7.78 (1H, s), 10.43 (1H, s), 11.02 (1H, brs), 11.58 (1H, brs). |
| 31 (Compound No. 58) | Yield: 5% $^1$H-NMR (DMSO-d$_6$) δ: 2.82 (3H, s), 3.06-3.51 (8H, m), 6.79-6.85 (2H, m), 7.12 (1H, d, J = 9.0 Hz), 7.40-7.45 (1H, m), 7.69 (1H, dd, J = 14.7, 2.1 Hz), 8.01-8.06 (1H, m), 10.40 (1H, s), 10.69 (1H, brs), 12.26 (1H, brs). |
| 32 (Compound No. 59) | Yield: 8% $^1$H-NMR (DMSO-d$_6$) δ: 2.84 (3H, s), 3.06-3.28 (4H, m), 3.40-3.52 (4H, m), 7.00-7.07 (1H, m), 7.14 (1H, t, J = 8.7 Hz), 7.28-7.36 (1H, m), 7.41-7.47 (1H, m), 7.68-7.76 (2H, m), 10.46 (2H, brs), 11.55 (1H, brs). |
| 33 (Compound No. 60) | Yield: 19% $^1$H-NMR (DMSO-d$_6$) δ: 2.84 (3H, s), 3.06-3.28 (4H, m), 3.40-3.52 (4H, m), 7.00 (1H, t, J = 8.1 Hz), 7.15 (1H, t, J = 9.3 Hz), 7.44-7.48 (1H, m), 7.62-7.68 (2H, m), 8.01 (1H, d, J = 8.1 Hz), 10.37 (1H, brs), 10.64 (1H, s), 12.66 (1H, brs). |
| 34 (Compound No. 61) | Yield: 7% $^1$H-NMR (DMSO-d$_6$) δ: 2.84 (3H, s), 3.06-3.52 (8H, m), 7.02-7.16 (3H, m), 7.41-7.44 (1H, m), 7.70 (1H, dd, J = 15.0, 2.7 Hz), 9.72 (1H, d, J = 2.7 Hz), 10.39 (1H, s), 10.47 (1H, brs), 12.01 (1H, brs). |
| 35 (Compound No. 62) | Yield: 6% $^1$H-NMR (DMSO-d$_6$) δ: 2.84 (3H, s), 3.06-3.52 (8H, m), 7.06-7.16 (2H, m), 7.43-7.46 (1H, m), 7.67-7.72 (1H, m), 7.97 (1H, dd, J = 8.4, 2.4 Hz), 8.50 (1H, d, J = 2.4 Hz), 10.38 (1H, brs), 10.54 (1H, s), 12.81 (1H, brs). |
| 36 (Compound No. 64) | Yield: 5% $^1$H-NMR (DMSO-d$_6$) δ: 2.81 (3H, s), 3.16-3.30 (8H, m), 6.37 (1H, d, J = 9.6 Hz), 7.07 (1H, t, J = 9.6 Hz), 7.21 (1H, dd, J = 8.7, 2.1 Hz), 7.78-7.88 (2H, m), 8.70 (1H, d, J = 3.3 Hz), 9.71 (1H, brs), 13.95 (1H, s). |
| 37 (Compound No. 69) | Yield: 34% $^1$H-NMR (DMSO-d$_6$) δ: 2.29 (3H, s), 2.53-2.60 (4H, m), 2.98-3.05 (4H, m), 6.88 (1H, d, J = 9.0 Hz), 7.03 (1H, t, J = 9.0 Hz), 7.32-7.40 (1H, m), 7.51 (1H, dd, J = 9.0, 2.1 Hz), 7.65 (1H, dd, J = 14.7, 2.1 Hz), 8.01 (1H, d, J = 2.4 Hz), 11.00 (1H, brs). |
| 38 (Compound No. 79) | Yield: 16% $^1$H-NMR (DMSO-d$_6$) δ: 2.31 (3H, s), 2.58-2.61 (4H, m), 3.12-3.15 (4H, m), 6.97 (1H, d, J = 9.0 Hz), 7.21 (1H, d, J = 8.7 Hz), 7.04-7.44 (1H, m), 7.82-7.89 (2H, m), 8.08-8.09 (1H, m), 10.98 (1H, brs). |
| 39 (Compound No. 90) | This compound was obtained as a hydrochloride. Yield: 7% $^1$H-NMR (DMSO-d$_6$) δ: 2.80-2.86 (3H, m), 3.01-3.13 (2H, m), 3.15-3.29 (2H, m), 3.40-3.55 (4H, m), 7.10-7.18 (2H, m), 7.40-7.47 (1H, m), 7.69 (1H, dd, J = 14.7, 2.1 Hz), 7.85 (1H, dd, J = 8.7, 2.1 Hz), 8.27 (1H, d, J = 2.1 Hz), 10.42 (1H, brs), 10.48 (1H, brs), 12.40 (1H, brs). |

Example 40

Preparation of N-[4-(4-aminopiperidin-1-yl)-3-fluorophenyl]-5-chloro-2-hydroxybenzamide hydrochloride (Compound No. 27)

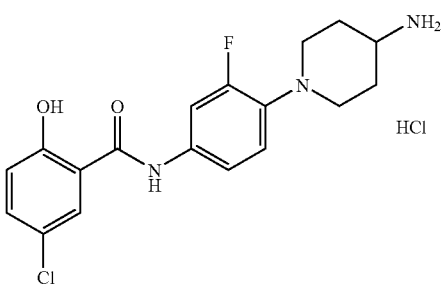

4N Hydrogen chloride/ethyl acetate solution (10.0 ml, 40.0 mmol) was added to a solution of (1-{4-[5-chloro-2-(2-methoxyethoxymethoxy)benzoylamino]-2-fluorophenyl}piperidin-4-yl)carbamic acid tert-butyl ester (compound of Reference Example 143; 0.15 g, 0.271 mmol) in ethyl acetate (2 ml) under ice cooling, and the mixture was stirred at room temperature for 3 hours. The precipitated crystal was collected by filtration and washed with ethyl acetate to give the title compound (0.10 g, 93%) as a colorless crystal.

$^1$H-NMR (DMSO-$d_6$) δ: 1.64-1.81 (2H, m), 1.96-2.07 (2H, m), 2.68-2.82 (2H, m), 3.09-3.23 (1H, m), 3.30-3.43 (2H, m), 7.05 (1H, d, J=3.0 Hz), 7.08 (1H, t, J=9.0 Hz), 7.40 (1H, dd, J=1.8, 8.4 Hz), 7.47 (1H, dd, J=2.7, 9.0 Hz), 7.65 (1H, dd, J=2.1, 14.1 Hz), 7.94 (1H, d, J=2.7 Hz), 8.19 (3H, brs), 10.44 (1H, s), 11.85 (1H, brs).

The compounds described in Examples 41 to 83 were obtained in the same manner as the method of Example 40, by deprotection reaction of the amide derivative having the appropriate protecting group(s).

TABLE 17

| Example | NMR |
|---|---|
| 41 (Compound No. 28) | Yield: 57% <br> $^1$H-NMR (DMSO-$d_6$) δ: 2.10 (3H, s), 2.55-2.63 (4H, m), 2.97-3.06 (4H, m), 3.26 (2H, brs), 6.97-7.11 (2H, m), 7.37 (1H, dd, J = 8.1, 2.4 Hz), 7.46 (1H, dd, J = 8.7, 2.7 Hz), 7.63 (1H, dd, J = 14.7, 2.1 Hz), 7.92 (1H, d, J = 2.7 Hz), 10.46 (1H, s), 11.79 (1H, s). |
| 42 (Compound No. 31) | Yield: 81% <br> $^1$H-NMR (DMSO-$d_6$) δ: 1.70-1.85 (2H, m), 1.97-2.10 (2H, m), 2.92-3.03 (2H, m), 3.14-3.26 (2H, m), 4.41-4.51 (1H, m), 6.49 (1H, d, J = 9.0 Hz), 7.02 (1H, dd, J = 3.0, 8.7 Hz), 7.15-7.22 (2H, m), 7.56 (1H, d, J = 3.0 Hz), 7.83 (1H, dd, J = 1.5, 13.8 Hz). |
| 43 (Compound No. 32) | This compound was obtained by conversion of the compound of Compound No. 31 into the hydrochloride thereof. <br> Yield: 91% <br> $^1$H-NMR (DMSO-$d_6$) δ: 1.78-1.96 (2H, m), 2.04-2.18 (2H, m), 3.02-3.14 (2H, brs), 3.17-3.29 (2H, brs), 4.55-4.65 (1H, m), 7.05 (1H, d, J = 9.0 Hz), 7.28 (1H, t, J = 9.0 Hz), 7.40-7.46 (1H, m), 7.46 (1H, dd, J = 3.0, 9.0 Hz), 7.74 (1H, dd, J = 2.4, 13.5 Hz), 7.93 (1H, d, J = 3.0 Hz), 8.92 (2H, brs), 10.46 (1H, s), 11.79 (1H, s). |
| 44 (Compound No. 36) | Yield: 54% <br> $^1$H-NMR (DMSO-$d_6$) δ: 3.20-3.32 (4H, m), 3.35 (2H, brs), 7.02 (1H, d, J = 8.7 Hz), 7.07 (1H, t, J = 9.6 Hz), 7.41 (1H, dd, J = 8.7, 1.8 Hz), 7.47 (1H, dd, J = 8.7, 2.7 Hz), 7.67 (1H, dd, J = 14.7, 2.1 Hz), 7.93 (1H, d, J = 3.0 Hz), 7.98 (1H, s), 10.41 (1H, s), 11.78 (1H, s). |
| 45 (Compound No. 38) | Yield: 73% <br> $^1$H-NMR (DMSO-$d_6$) δ: 1.81-1.91 (1H, m), 2.28-2.35 (1H, m), 2.38 (3H, s), 2.43-2.53 (2H, m), 2.79-2.93 (2H, m), 4.90-4.96 (1H, m), 6.91 (1H, d, J = 9.0 Hz), 7.10 (1H, t, J = 9.0 Hz), 7.32-7.39 (2H, m), 7.72 (1H, dd, J = 13.8, 2.7 Hz), 7.87 (1H, d, J = 2.7 Hz), 11.24 (1H, brs). |
| 46 (Compound No. 39) | Yield: 38% <br> $^1$H-NMR (DMSO-$d_6$) δ: 2.64 (4H, t, J = 6.0 Hz), 3.41 (4H, t, J = 6.0 Hz), 6.96-7.03 (2H, m), 7.18-7.22 (1H, m), 7.40 (1H, dd, J = 8.7, 2.4 Hz), 7.48-7.55 (2H, m), 8.00 (1H, brs), 11.79 (1H, brs). |
| 47 (Compound No. 40) | Yield: 68% <br> $^1$H-NMR (DMSO-$d_6$) δ: 1.41-1.57 (2H, m), 1.82-1.94 (2H, m), 2.03-2.17 (2H, m), 2.76-2.87 (2H, m), 3.20-3.44 (1H, m), 3.50 (2H, s), 4.98 (1H, m), 6.76 (1H, t, J = 9.3 Hz), 6.93 (1H, d, J = 8.7 Hz), 7.19 (1H, d, J = 8.4 Hz), 7.22-7.36 (5H, m), 7.39 (1H, dd, J = 9.0, 2.7 Hz), 7.53 (1H, dd, J = 14.1, 2.1 Hz), 7.93 (1H, d, J = 2.7 Hz), 10.78 (2H, brs). |
| 48 (Compound No. 42) | Yield: 50% <br> $^1$H-NMR (DMSO-$d_6$) δ: 1.85-1.99 (1H, m), 2.19-2.33 (1H, m), 3.23-3.37 (2H, m), 3.43-3.59 (2H, m), 3.77-3.88 (1H, m), 6.54 (1H, d, J = 8.7 Hz), 6.62 (1H, t, J = 9.0 Hz), 7.00-7.08 (2H, m), 7.69 (1H, d, J = 3.0 Hz), 7.74 (1H, dd, J = 16.2, 2.4 Hz), 7.98 (2H, brs), 14.05 (2H, brs). |

TABLE 17-continued

| Example | NMR |
|---|---|
| 49 (Compound No. 44) | Yield: 68%<br>$^1$H-NMR (DMSO-d$_6$) δ: 1.98-2.02 (2H, m), 3.13-3.21 (4H, m), 3.29 (2H, t, J = 5.7 Hz), 3.37-3.40 (2H, m), 6.51 (1H, d, J = 9.0 Hz), 6.59 (1H, t, J = 9.0 Hz), 7.02 (1H, dd, J = 9.0, 3.0 Hz), 7.10-7.13 (1H, m), 7.67 (1H, d, J = 3.0 Hz), 7.74 (1H, dd, J = 15.6, 2.1 Hz). |
| 50 (Compound No. 45) | Yield: 97%<br>$^1$H-NMR (DMSO-d$_6$) δ: 1.49-1.59 (2H, m), 1.89-1.94 (2H, m), 2.02-2.14 (1H, m), 2.82-2.96 (2H, m), 3.27-3.32 (2H, m), 3.94 (2H, d, J = 6.3 Hz), 7.06 (1H, d, J = 9.0 Hz), 7.20 (1H, t, J = 9.0 Hz), 7.40-7.49 (2H, m), 7.70 (1H, dd, J = 15.0, 2.7 Hz), 7.95 (1H, d, J = 2.7 Hz), 8.63-8.66 (1H, m), 8.97-8.99 (1H, m), 10.44 (1H, s), 11.86 (1H, s). |
| 51 (Compound No. 46) | Yield: 84%<br>$^1$H-NMR (DMSO-d$_6$) δ: 1.67-1.84 (1H, m), 1.84-2.05 (2H, m), 2.08-2.20 (1H, m), 3.15-3.28 (2H, m), 3.94 (1H, brs), 4.24 (1H, dd, J = 10.8, 8.1 Hz), 4.32 (1H, dd, J = 10.8, 3.9 Hz), 7.07 (1H, d, J = 8.7 Hz), 7.25 (1H, t, J = 9.3 Hz), 7.45 (1H, dd, J = 9.0, 1.2 Hz), 7.47 (1H, dd, J = 8.7, 2.7 Hz), 7.76 (1H, dd, J = 13.5, 2.7 Hz), 7.95 (1H, d, J = 3.0 Hz), 9.13 (1H, brs), 9.60 (1H, brs), 10.47 (1H, s), 11.84 (1H, s). |
| 52 (Compound No. 47) | Yield: 83%<br>$^1$H-NMR (DMSO-d$_6$) δ: 1.41-1.60 (2H, m), 1.74-1.98 (3H, m), 2.70-2.94 (4H, m), 3.36-3.49 (2H, m), 7.09 (1H, d, J = 8.7 Hz), 7.29 (1H, t, J = 9.0 Hz), 7.45 (1H, dd, J = 8.7, 1.8 Hz), 7.47 (1H, dd, J = 9.0, 3.0 Hz), 7.73 (1H, dd, J = 14.4, 2.1 Hz), 7.95 (1H, d, J = 2.7 Hz), 8.15 (3H, brs), 10.53 (1H, s), 11.86 (1H, s). |
| 53 (Compound No. 48) | Yield: 34%<br>$^1$H-NMR (DMSO-d$_6$) δ: 1.45-1.63 (1H, m), 1.68-2.00 (3H, m), 2.66-2.80 (1H, m), 2.85-3.10 (2H, m), 3.35-3.49 (2H, m), 6.98 (1H, brs), 7.09 (1H, d, J = 8.7 Hz), 7.36-7.58 (4H, m), 7.77 (1H, d, J = 14.7 Hz), 7.94 (1H, d, J = 2.4 Hz), 10.57 (1H, s), 11.83 (1H, brs). |
| 54 (Compound No. 49) | Yield: 66%<br>$^1$H-NMR (DMSO-d$_6$) δ: 1.28-1.42 (1H, m), 1.65-1.85 (3H, m), 2.25-2.32 (1H, m), 2.70-2.81 (2H, m), 3.22-3.39 (2H, m), 3.91-4.06 (2H, m), 7.07 (1H, d, J = 9.0 Hz), 7.20 (1H, t, J = 9.0 Hz), 7.40-7.49 (2H, m), 7.70 (1H, dd, J = 15.0, 2.7 Hz), 7.95 (1H, d, J = 2.7 Hz), 8.63-8.66 (1H, m), 8.97-8.99 (1H, m), 10.44 (1H, s), 11.86 (1H, s). |
| 55 (Compound No. 50) | Yield: 30%<br>$^1$H-NMR (DMSO-d$_6$) δ: 1.45-1.60 (2H, m), 1.69-1.75 (2H, m), 2.01-2.23 (3H, m), 2.35 (3H, s), 2.83-3.02 (2H, m), 3.86-3.97 (2H, m), 6.84 (1H, d, J = 9.0 Hz), 7.14 (1H, t, J = 8.7 Hz), 7.28-7.32 (2H, m), 7.73 (1H, dd, J = 14.1, 2.7 Hz), 7.83 (1H, d, J = 2.7 Hz), 11.83 (1H, brs). |
| 56 (Compound No. 51) | Yield: 7%<br>$^1$H-NMR (DMSO-d$_6$) δ: 1.32-1.45 (2H, m), 1.79-1.84 (3H, m), 2.20-2.30 (2H, m), 2.37 (3H, s), 2.98-3.03 (2H, m), 3.90 (2H, d, J = 6.3 Hz), 6.77 (1H, d, J = 9.0 Hz), 7.13 (1H, t, J = 9.0 Hz), 7.24-7.30 (2H, m), 7.73 (1H, dd, J = 14.1, 3.0 Hz), 7.80 (1H, d, J = 3.0 Hz), 12.22 (1H, brs). |
| 57 (Compound No. 52) | Yield: 17%<br>$^1$H-NMR (DMSO-d$_6$) δ: 1.88-1.92 (2H, m), 2.56-2.69 (2H, m), 2.75-2.78 (2H, m), 3.34-3.38 (4H, m), 3.68 (2H, s), 6.91-6.98 (2H, m), 7.23-7.34 (6H, m), 7.43 (1H, dd, J = 8.7, 2.7 Hz), 7.58 (1H, dd, J = 15.9, 2.7 Hz), 7.94 (1H, d, J = 2.7 Hz), 10.62 (1H, brs). |
| 58 (Compound No. 53) | Yield: 28%<br>$^1$H-NMR (DMSO-d$_6$) δ: 1.87 (3H, t, J = 7.5 Hz), 1.92-1.99 (2H, m), 2.72 (2H, q, J = 7.5 Hz), 2.83-2.87 (2H, m), 2.91-2.94 (2H, m), 3.29-3.33 (2H, m), 3.56-3.58 (2H, m), 6.83 (1H, d, J = 9.0 Hz), 6.94 (1H, t, J = 9.0 Hz), 7.22 (1H, dd, J = 9.0, 2.1 Hz), 7.29 (1H, dd, J = 9.0, 3.0 Hz), 7.64 (1H, dd, J = 15.9, 2.1 Hz), 7.84 (1H, d, J = 3.0 Hz), 11.80 (1H, brs). |
| 59 (Compound No. 54) | Yield: 87%<br>$^1$H-NMR (DMSO-d$_6$) δ: 1.08-1.24 (1H, m), 1.55-1.89 (3H, m), 2.05 (1H, brs), 2.50-2.60 (1H, m), 2.65-2.81 (3H, m), 3.18-3.27 (1H, m), 3.31-3.39 (1H, m), 7.05 (1H, d, J = 9.0 Hz), 7.15 (1H, t, J = 9.0 Hz), 7.40 (1H, dd, J = 9.0, 2.1 Hz), 7.44 (1H, dd, J = 8.7, 2.1 Hz), 7.66 (1H, dd, J = 14.7, 2.1 Hz), 7.93 (1H, d, J = 2.7 Hz), 8.07 (3H, s), 10.46 (1H, s), 11.85 (1H, brs). |

TABLE 17-continued

| Example | NMR |
|---|---|
| 60 (Compound No. 55) | Yield: 85%<br>$^1$H-NMR (DMSO-$d_6$) δ: 2.13-2.21 (2H, m), 3.20-3.55 (4H, m), 5.10-5.16 (1H, m), 7.06 (1H, d, J = 8.7 Hz), 7.26 (1H, t, J = 9.0 Hz), 7.42-7.50 (2H, m), 7.76 (1H, dd, J = 13.5, 2.4 Hz), 7.93 (1H, d, J = 2.4 Hz), 9.38 (1H, brs), 9.56 (1H, brs), 10.48 (1H, s), 11.80 (1H, s). |
| 61 (Compound No. 56) | Yield: 14%<br>$^1$H-NMR (DMSO-$d_6$) δ: 1.71-1.99 (4H, m), 3.06-3.45 (4H, m), 4.58-4.62 (1H, m), 7.05 (1H, d, J = 9.0 Hz), 7.31 (1H, t, J = 9.0 Hz), 7.42-7.49 (2H, m), 7.66 (1H, dd, J = 13.2, 2.4 Hz), 7.92 (1H, d, J = 2.4 Hz), 8.81 (1H, brs), 9.25 (1H, brs), 10.47 (1H, s), 11.78 (1H, s). |
| 62 (Compound No. 63) | Yield: 90%<br>$^1$H-NMR (DMSO-$d_6$) δ: 1.35-1.65 (5H, m), 1.73-1.86 (2H, m), 2.73-2.93 (4H, m), 3.33-3.46 (2H, m), 7.06 (1H, d, J = 9.0 Hz), 7.27 (1H, brs), 7.41-7.46 (1H, m), 7.47 (1H, dd, J = 9.0, 2.7 Hz), 7.72 (1H, dd, J = 15.0, 2.7 Hz), 7.89-8.01 (4H, m), 10.49 (1H, s), 11.83 (1H, brs). |
| 63 (Compound No. 65) | Yield: 79%<br>$^1$H-NMR (DMSO-$d_6$) δ: 1.45-1.52 (4H, m), 1.99-2.11 (4H, m), 3.39 (1H, brs), 4.22-4.25 (1H, m), 7.06 (1H, d, J = 9.0 Hz), 7.26 (1H, t, J = 9.0 Hz), 7.39-7.48 (2H, m), 7.70 (1H, dd, J = 13.8, 2.4 Hz), 7.95 (1H, d, J = 2.7 Hz), 8.13-8.16 (2H, m), 10.45 (2H, brs), 11.86 (1H, s). |
| 64 (Compound No. 66) | Yield: 93%<br>$^1$H-NMR (DMSO-$d_6$) δ: 1.58-1.74 (2H, m), 1.90-2.01 (2H, m), 2.63-2.76 (2H, m), 3.07-3.19 (2H, m), 3.25-3.55 (3H, m), 6.40 (1H, d, J = 8.7 Hz), 6.91-7.00 (2H, m), 7.13 (1H, dd, J = 8.7, 1.8 Hz), 7.62 (1H, d, J = 3.0 Hz), 7.75 (1H, dd, J = 15.0, 2.4 Hz). |
| 65 (Compound No. 67) | Yield: 32%<br>$^1$H-NMR (DMSO-$d_6$) δ: 1.60-1.79 (2H, m), 1.93-2.07 (2H, m), 2.68-2.81 (2H, m), 3.16 (1H, brs), 3.31-3.42 (2H, m), 6.98 (1H, d, J = 8.7 Hz), 7.07 (1H, t, J = 9.0 Hz), 7.40 (1H, d, J = 8.4 Hz), 7.57 (1H, dd, J = 8.7, 2.7 Hz), 7.64 (1H, dd, J = 15.0, 2.4 Hz), 8.05 (1H, d, J = 2.4 Hz), 8.10 (3H, brs), 10.41 (1H, s), 11.84 (1H, brs). |
| 66 (Compound No. 68) | Yield: 84%<br>$^1$H-NMR (DMSO-$d_6$) δ: 1.58-1.69 (2H, m), 2.01-2.05 (2H, m), 2.44-2.66 (6H, m), 2.90-2.97 (1H, m), 3.26-3.30 (2H, m), 6.48 (1H, d, J = 9.0 Hz), 6.81 (1H, t, J = 9.0 Hz), 7.02 (1H, dd, J = 9.0, 3.0 Hz), 7.11-7.15 (1H, m), 7.67 (1H, d, J = 3.0 Hz), 7.78 (1H, dd, J = 15.0, 2.1 Hz), 14.31 (1H, brs). |
| 67 (Compound No. 71) | Yield: 56%<br>$^1$H-NMR (DMSO-$d_6$) δ: 1.61-1.85 (2H, m), 1.94-2.10 (2H, m), 2.65-2.87 (2H, m), 3.15 (1H, brs), 3.28-3.48 (2H, m), 6.98-7.18 (3H, m), 7.40 (1H, d, J = 8.0 Hz), 7.67 (1H, dd, J = 14.8, 2.2 Hz), 7.95 (1H, d, J = 8.5 Hz), 8.10-8.35 (3H, m), 10.40 (1H, s), 12.13 (1H, brs). |
| 68 (Compound No. 72) | Yield: 60%<br>$^1$H-NMR (DMSO-$d_6$) δ: 0.99 (3H, t, J = 7.5 Hz), 1.63-1.73 (2H, m), 2.80-2.87 (1H, m), 3.03-3.45 (6H, m), 7.05 (1H, d, J = 8.8 Hz), 7.15 (1H, t, J = 8.8 Hz), 7.41-7.45 (1H, m), 7.48 (1H, dd, J = 8.8, 2.7 Hz), 7.70 (1H, dd, J = 8.8, 2.7 Hz), 7.93 (1H, d, J = 2.7 Hz), 9.29 (2H, brs), 10.46 (1H, s), 11.81 (1H, brs). |
| 69 (Compound No. 73) | Yield: 78%<br>$^1$H-NMR (DMSO-$d_6$) δ: 1.30 (3H, d, J = 6.4 Hz), 2.80-2.88 (1H, m), 2.99-3.17 (2H, m), 3.34-3.41 (4H, m), 7.05 (1H, d, J = 8.8 Hz), 7.13 (1H, t, J = 9.3 Hz), 7.41-7.49 (2H, m), 7.67-7.73 (1H, m), 7.93 (1H, d, J = 2.6 Hz), 9.19-9.41 (2H, m), 10.47 (1H, s), 11.82 (1H, brs). |
| 70 (Compound No. 74) | Yield: 87%<br>$^1$H-NMR (DMSO-$d_6$) δ: 1.64-1.75 (2H, m), 1.99-2.02 (2H, m), 2.78-2.86 (2H, m), 2.95-2.99 (2H, m), 3.15 (1H, brs), 7.07 (1H, d, J = 8.8 Hz), 7.47 (1H, dd, J = 9.0, 2.7 Hz), 7.58 (1H, d, J = 8.8 Hz), 7.93-7.96 (2H, m), 8.11-8.17 (4H, m), 10.62 (1H, s), 11.75 (1H, brs). |
| 71 (Compound No. 75) | Yield: 70%<br>$^1$H-NMR (DMSO-$d_6$) δ: 1.68-1.79 (2H, m), 1.99-2.09 (2H, m), 2.68-2.75 (2H, m), 3.15 (1H, brs), 3.26-3.30 (2H, m), 7.07 (1H, d, J = 8.8 Hz), 7.18 (1H, d, J = 8.8 Hz), 7.45-7.49 (1H, m), 7.60 (1H, dd, J = 8.8, 2.4 Hz), 7.90 (1H, d, J = 2.4 Hz), 7.95-7.96 (1H, m), 8.28 (3H, brs), 10.47 (1H, s), 11.87 (1H, brs). |

TABLE 17-continued

| Example | NMR |
| --- | --- |
| 72 (Compound No. 76) | Yield: 52%<br>$^1$H-NMR (DMSO-$d_6$) δ: 2.03 (2H, quint, J = 6.0 Hz), 3.05 (2H, t, J = 6.0 Hz), 3.16-3.27 (4H, m), 3.42 (2H, brs), 7.07 (1H, d, J = 8.8 Hz), 7.47 (1H, dd, J = 8.8, 2.6 Hz), 7.62 (1H, d, J = 8.6 Hz), 7.93 (1H, d, J = 2.6 Hz), 7.95-7.99 (1H, m), 8.11-8.13 (1H, m), 9.21 (2H, brs), 10.62 (1H, s), 11.72 (1H, s). |
| 73 (Compound No. 77) | Yield: 54%<br>$^1$H-NMR (DMSO-$d_6$) δ: 1.97-2.03 (2H, m), 2.53 (3H, s), 2.89-2.93 (2H, m), 2.96-2.99 (2H, m), 3.28-3.32 (2H, m), 3.36-3.38 (2H, m), 6.59-6.62 (2H, m), 6.73 (1H, s), 6.93 (1H, t, J = 9.0 Hz), 7.17-7.21 (1H, m), 7.67 (1H, dd, J = 15.9, 2.4 Hz), 7.80 (1H, d, J = 8.4 Hz), 12.47 (1H, brs). |
| 74 (Compound No. 80) | Yield: 68%<br>$^1$H-NMR (DMSO-$d_6$) δ: 2.01-2.04 (2H, m), 3.17-3.30 (6H, m), 3.38-3.40 (2H, m), 6.26 (1H, dd, J = 8.4, 2.1 Hz), 6.46 (1H, d, J = 2.1 Hz), 6.92 (1H, t, J = 9.0 Hz), 7.07 (1H, dd, J = 9.0, 2.1 Hz), 7.69 (1H, d, J = 8.4 Hz), 7.77 (1H, dd, J = 15.9, 2.1 Hz), 14.26 (1H, brs). |
| 75 (Compound No. 81) | Yield: 85%<br>$^1$H-NMR (DMSO-$d_6$) δ: 2.07-2.13 (2H, m), 3.19-3.38 (8H, m), 7.07 (1H, d, J = 8.8 Hz), 7.24-7.28 (1H, m), 7.46 (1H, dd, J = 8.8, 2.7 Hz), 7.58 (1H, dd, J = 8.8, 2.6 Hz), 7.91 (1H, d, J = 2.6 Hz), 7.95 (1H, d, J = 2.7 Hz), 9.31 (2H, brs), 10.47 (1H, s), 11.85 (1H, brs). |
| 76 (Compound No. 82) | Yield: 71%<br>$^1$H-NMR (DMSO-$d_6$) δ: 0.96-1.20 (3H, m), 1.56-1.74 (1H, m), 1.83-2.06 (2H, m), 2.09-2.25 (1H, m), 3.16-3.37 (1H, m), 3.51-3.72 (1H, m), 3.86-4.03 (1H, m), 6.38 (1H, brs), 7.04 (1H, d, J = 9.0 Hz), 7.28-7.50 (1H, m), 7.46 (1H, dd, J = 9.0, 2.7 Hz), 7.58-7.82 (1H, m), 7.95 (1H, d, J = 2.7 Hz), 10.44 (1H, brs), 11.88 (1H, brs). |
| 77 (Compound No. 83) | This compound was obtained from the compound of Reference Example 177(a) as a law material.<br>Yield: 62%<br>$^1$H-NMR (DMSO-$d_6$) δ: 1.52 (6H, d, J = 6.6 Hz), 2.29-2.52 (4H, m), 4.02-4.24 (2H, m), 7.12 (1H, d, J = 9.0 Hz), 7.37 (1H, dd, J = 9.0, 2.4 Hz), 7.56 (1H, d, J = 9.3 Hz), 8.33-8.51 (3H, m), 10.52 (1H, s), 11.68 (1H, s), 12.57 (1H, brs). |
| 78 (Compound No. 84) | This compound was obtained from the compound of Reference Example 177(b) as a law material.<br>Yield: 63%<br>$^1$H-NMR (DMSO-$d_6$) δ: 0.96-1.38 (3H, m), 1.38-1.77 (4H, m), 1.77-2.19 (1H, m), 2.19-2.58 (2H, m), 3.92-4.65 (2H, m), 7.07 (1H, d, J = 8.7 Hz), 7.29-7.60 (1H, m), 7.37 (1H, d, J = 8.7 Hz), 7.82-7.62 (3H, m), 10.41 (1H, brs), 11.72 (1H, brs). |
| 79 (Compound No. 85) | Yield: 73%<br>$^1$H-NMR (DMSO-$d_6$) δ: 0.87 (3H, d, J = 6.0 Hz), 1.24 (3H, d, J = 6.5 Hz), 2.69-2.81 (1H, m), 2.94 (1H, t, J = 9.5 Hz), 3.11 (1H, dd, J = 12.5, 3.0 Hz), 3.33-3.36 (3H, m), 7.08 (1H, d, J = 9.0 Hz), 7.27 (1H, t, J = 9.0 Hz), 7.46 (2H, dd, J = 9.0, 2.5 Hz), 7.73 (1H, dd, J = 13.5, 2.0 Hz), 7.90 (1H, d, J = 2.5 Hz), 9.30-9.40 (1H, m), 9.53-9.63 (1H, m), 10.54 (1H, s), 11.75 (1H, brs). |
| 80 (Compound No. 86) | Yield: 43%<br>$^1$H-NMR (DMSO-$d_6$) δ: 1.94-1.98 (2H, m), 2.45 (3H, s), 2.77-2.81 (2H, m), 2.85-2.88 (2H, m), 3.29-3.33 (2H, m), 3.35-3.37 (2H, m), 6.74 (1H, d, J = 8.7 Hz), 6.93 (1H, t, J = 9.0 Hz), 7.21 (1H, dd, J = 8.7, 2.1 Hz), 7.37 (1H, dd, J = 9.0, 2.7 Hz), 7.64 (1H, dd, J = 15.6, 2.1 Hz), 7.94 (1H, d, J = 2.7 Hz), 11.96 (1H, brs). |
| 81 (Compound No. 87) | Yield: 39%<br>$^1$H-NMR (DMSO-$d_6$) δ: 1.99-2.03 (2H, m), 3.14-3.18 (2H, m), 3.19-3.23 (2H, m), 3.27-3.31 (2H, m), 3.37-3.39 (2H, m), 6.44 (1H, d, J = 9.0 Hz), 6.94 (1H, t, J = 8.7 Hz), 7.09-7.12 (2H, m), 7.72-7.78 (2H, m), 14.29 (1H, brs). |
| 82 (Compound No. 88) | Yield: 70%<br>$^1$H-NMR (DMSO-$d_6$) δ: 0.93 (3H, d, J = 6.4 Hz), 2.81-2.90 (1H, m), 3.11-3.33 (5H, m), 3.51-3.56 (1H, m), 7.08 (1H, d, J = 8.8 Hz), 7.22 (1H, t, J = 9.1 Hz), 7.44-7.48 (2H, m), 7.69-7.75 (1H, m), 7.92 (1H, d, J = 2.7 Hz), 9.32 (1H, brs), 9.42 (1H, brs), 10.53 (1H, s), 11.78 (1H, brs). |
| 83 (Compound No. 89) | Yield: 50%<br>$^1$H-NMR (DMSO-$d_6$) δ: 0.75 (3H, t, J = 7.4 Hz), 1.37-1.56 (2H, m), 3.00-3.41 (7H, m), 7.07 (1H, d, J = 8.8 Hz), 7.21 (1H, t, J = 9.1 Hz), 7.43-7.49 (2H, m), 7.68-7.73 (1H, m), 7.92 (1H, d, J = 2.6 Hz), 9.26 (1H, brs), 9.33 (1H, brs), 10.51 (1H, s), 11.77 (1H, brs). |

Example 84

Preparation of 5-chloro-N-[3-fluoro-4-(piperazin-1-yl)phenyl]-2-hydroxybenzamide (Compound No. 22)

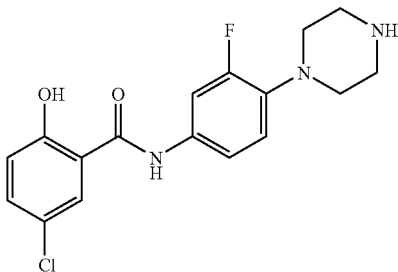

2-Acetoxy-5-chlorobenzoic acid (0.257 g, 1.20 mmol), phosphorus oxychloride (0.184 g, 1.20 mmol) and pyridine (0.095 g, 1.20 mmol) were added to a solution of 1-[4-(4-amino-2-fluorophenyl)piperazin-1-yl]ethanone (compound of Reference Example 85; 0.237 g, 1.00 mmol) in tetrahydrofuran (3 ml) under ice cooling, and the mixture was stirred under ice cooling for 3 hours. The reaction mixture was neutralized by addition of saturated aqueous sodium hydrogencarbonate, diluted with water, and extracted with ethyl acetate. The organic layer was washed with saturated brine and dried over sodium sulfate. 6N Hydrochloric acid (6 ml) was added to the residue obtained by evaporation of the solvent under reduced pressure, and the mixture was refluxed for 5 hours. The reaction mixture was cooled to room temperature and neutralized by addition of 2N aqueous sodium hydroxide. The precipitated solid was collected by filtration, washed with water, and purified by column chromatography on silica gel (methanol:chloroform=1:10) to give the title compound (0.017 g, 5%) as a yellow solid.

$^1$H-NMR (CD$_3$OD) δ: 3.32 (4H, t, J=6.0 Hz), 3.40 (4H, t, J=6.0 Hz), 6.96 (1H, d, J=9.0 Hz), 7.10 (1H, t, J=9.0 Hz), 7.32-7.42 (1H, m), 7.40 (1H, dd, J=9.0, 2.5 Hz), 7.66 (1H, dd, J=14.0, 2.5 Hz), 7.96 (1H, d, J=2.5 Hz).

The compound described in Example 85 was obtained in the same manner as the method of Example 84, except that the compound of Reference Examples 86 was used instead of the compound of Reference Examples 85.

TABLE 18

| Example | NMR |
|---|---|
| 85 (Compound No. 23) | Yield: 10% <br> $^1$H-NMR (CD$_3$OD) δ: 2.35 (3H, s), 3.14 (4H, t, J = 5.0 Hz), 3.39 (4H, t, J = 5.0 Hz), 6.96 (1H, d, J = 9.0 Hz), 7.12 (1H, d, J = 8.5 Hz), 7.40 (1H, dd, J = 8.5, 3.0 Hz), 7.50-7.54 (2H, m), 7.97 (1H, d, J = 2.5 Hz). |

Example 86

Preparation of 5-chloro-N-{3-fluoro-4-[4-(2-hydroxypropan-1-yl)piperazin-1-yl]phenyl}-2-hydroxybenzamide hydrochloride (Compound No. 29)

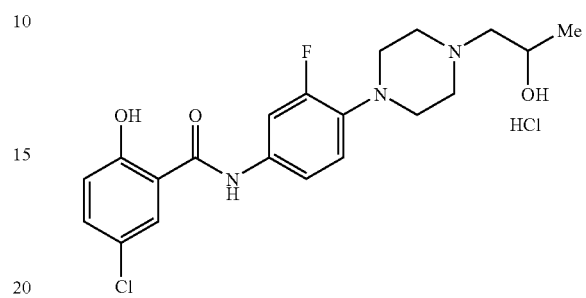

Sodium borohydride (0.038 g, 1.00 mmol) was added to a solution of 5-chloro-N-{3-fluoro-4-[4-(2-oxopropan-1-yl)piperazin-1-yl]phenyl}-2-(2-methoxyethoxy methoxy)benzamide (compound of Reference Example 144; 0.134 g, 0.272 mmol) in methanol (1 ml) under ice cooling, and the mixture was stirred at room temperature for 1 hour. 0.5N Hydrochloric acid was added to the reaction mixture, and the mixture was concentrated under reduced pressure. The precipitated solid was collected by filtration and washed with water. 2N Hydrochloric acid was added to the obtained solid, and the mixture was refluxed for 1 hour. The reaction mixture was cooled to room temperature, and the precipitated solid was collected by filtration and washed with acetone to give the title compound (0.113 g, 93%) as a white solid.

$^1$H-NMR (DMSO-d$_6$) δ: 1.11 (3H, d, J=6.3 Hz), 2.90-3.68 (10H, m), 4.14 (1H, brs), 5.49 (1H, brs), 7.02 (1H, d, J=8.7 Hz), 7.10 (1H, t, J=9.3 Hz), 7.45 (1H, dd, J=8.7, 2.7 Hz), 7.38-7.44 (1H, m), 7.68 (1H, dd, J=14.7, 2.1 Hz), 7.91 (1H, d, J=2.7 Hz), 9.93 (1H, brs), 10.44 (1H, s), 11.78 (1H, brs).

The compound described in Example 87 was obtained in the same manner as the method of Example 86, except that the compound of compound No. 39 was used instead of the compound of Reference Examples 144.

TABLE 19

| Example | NMR |
|---|---|
| 87 (Compound No. 43) | Yield: 59% <br> $^1$H-NMR (DMSO-d$_6$) δ: 1.63-1.70 (2H, m), 1.90-1.99 (2H, m), 2.94-2.98 (2H, m), 3.32-3.38 (2H, m), 3.66-3.72 (1H, m), 4.47 (1H, brs), 7.04 (1H, d, J = 8.7 Hz), 7.31-7.48 (3H, m), 7.69-7.75 (1H, m), 7.92 (1H, d, J = 2.4 Hz), 10.49 (1H, s), 11.79 (1H, brs). |

Example 88

Preparation of 5-chloro-N-[3-fluoro-4-(piperidin-4-yl)phenyl]-2-hydroxybenzamide hydrochloride (Compound No. 41)

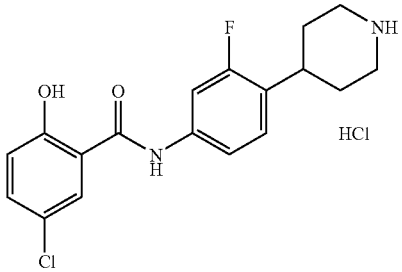

A mixture of 5-chloro-N-[3-fluoro-4-(pyridin-4-yl)phenyl]-2-hydroxybenzamide (compound of Reference Example 186; 0.104 g, 0.303 mmol), platinum(IV) oxide (0.100 g, 0.440 mmol) and methanol (10 ml) was stirred under ice cooling for 5 hours under hydrogen atmosphere. The reaction mixture was filtered, and the residue obtained by evaporation of the solvent of the filtrate under reduced pressure was purified by column chromatography on silica gel. 2N Hydrochloric acid was added to the obtained purified substance, and the mixture was refluxed for 1 hour. The solvent was evaporated under reduced pressure to give the title compound (0.021 g, 18%) as a colorless solid.

$^1$H-NMR (DMSO-$d_6$) δ: 1.84-1.97 (4H, m), 2.94-3.18 (4H, m), 3.38 (1H, brs), 7.07 (1H, d, J=8.7 Hz), 7.27 (1H, t, J=8.7 Hz), 7.44-7.52 (2H, m), 7.69 (1H, dd, J=12.8, 1.8 Hz), 7.92 (1H, d, J=3.0 Hz), 8.83 (1H, brs), 8.97 (1H, brs), 10.54 (1H, s), 11.75 (1H, s).

Reference Example 189

Preparation of 4-{[4-(5-chloro-2-hydroxybenzoylamino)-2-fluorophenyl]amino}piperidine-1-carboxylic acid ethyl ester

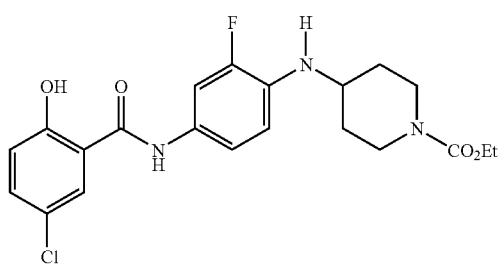

The title compound was obtained in the same manner as Example 40 using the following raw material.

Raw Material:

4-({4-[5-chloro-2-(2-methoxyethoxymethoxy)benzoylamino]-2-fluorophenyl}amino)piperidine-1-carboxylic acid ethyl ester (compound of Reference Example 167)

Yield: Quantitative $^1$H-NMR (DMSO-$d_6$) δ: 1.19 (3H, t, J=6.9 Hz), 1.26-1.42 (2H, m), 1.83-1.94 (2H, m), 2.85-3.02 (2H, m), 3.44-3.53 (1H, m), 3.95 (2H, brs), 4.03 (2H, q, J=7.2 Hz), 5.12 (1H, d, J=7.5 Hz), 6.82 (1H, t, J=9.0 Hz), 6.99 (1H, d, J=8.7 Hz), 7.24 (1H, d, J=8.7 Hz), 7.46 (1H, dd, J=8.7, 2.4 Hz), 7.52 (1H, dd, J=13.8, 2.4 Hz), 7.97 (1H, d, J=2.7 Hz), 10.27 (1H, s), 12.01 (1H, brs).

Example 89

Preparation of 5-chloro-N-[3-fluoro-4-(piperidin-4-ylamino)phenyl]-2-hydroxybenzamide (Compound No. 70)

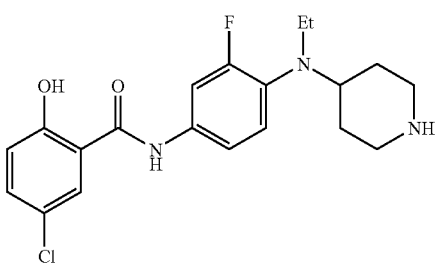

Hydrazine monohydrate (0.227 ml, 5.70 mmol) and potassium hydroxide (0.641 g, 11.4 mmol) were added to a solution of 4-{[4-(5-chloro-2-hydroxybenzoylamino)-2-fluorophenyl]amino}piperidine-1-carboxylic acid ethyl ester (compound of Reference Example 189; 0.500 g, 1.14 mmol) in ethyleneglycol (10 ml), and the mixture was refluxed for 1 hour. The reaction mixture was cooled to room temperature, and saturated aqueous ammonium chloride and water were added. The precipitated solid was collected by filtration and washed with water to give the title compound (0.267 g, 64%) as an ivory solid.

$^1$H-NMR (DMSO-$d_6$) δ: 1.47-1.66 (2H, m), 1.92-2.09 (2H, m), 2.84-3.00 (2H, m), 3.18-3.34 (2H, m), 3.47 (1H, brs), 5.06 (1H, d, J=7.2 Hz), 6.49 (1H, d, J=9.0 Hz), 6.77 (1H, t, J=9.0 Hz), 7.01 (1H, d, J=9.0, 3.0 Hz), 7.06 (1H, d, J=8.4, 1.5 Hz), 7.64-7.74 (2H, m).

Example 90

Preparation of 5-chloro-N-[4-(4-dimethylaminopiperidin-1-yl)-3-fluorophenyl]-2-hydroxybenzamide hydrochloride (Compound No. 78)

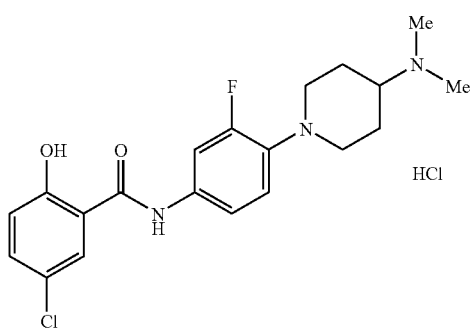

The title compound was obtained in the same manner as Reference Example 61 using the following raw material.

Raw Material:

5-chloro-N-[3-fluoro-4-(4-methylaminopiperidin-1-yl)phenyl]-2-hydroxybenzamide (Compound No. 68).

Yield: 82% (white solid)

$^1$H-NMR (DMSO-$d_6$) δ: 1.82-1.90 (2H, m), 2.09-2.18 (2H, m), 2.69-2.76 (8H, m), 3.24-3.31 (1H, m), 3.44-3.48 (2H, m), 7.05-7.14 (2H, m), 7.39-7.48 (2H, m), 7.67 (1H, dd, J=14.7, 2.7 Hz), 7.95 (1H, d, J=2.7 Hz), 10.46 (1H, brs), 10.92 (1H, brs), 11.89 (1H, brs).

Test Example 1

STAT6 Inhibition Test (1) Construction of a STAT6 Reporter Plasmid

The Oligonucleotides (SEQ ID: 1, 2) containing two copies of STAT6 binding sequences (refer to J. Biol. Chem., vol. 276, No. 9, pp. 6675-6688 (2001).) were synthesized, and integrated into the enhancer region of the reporter plasmid pTA-Luc Vector (CLONTECH Laboratories, Inc.) at the restriction enzyme BglII site.

When the oligonucleotide is integrated in positive direction into the plasmid, the upstream BglII site is not reconstructed. Therefore, STAT6 binding sequences can be increased by repeating integration of the oligonucleotide at the restriction enzyme BglII site.

In the present test, a plasmid including eight integrated STAT6 binding sequences was constructed and provided for the reporter assay as (GLS)x8/pTA-Luc. Confirmation of the sequences was carried out using an automated fluorescence sequencer (Model 310 (Applied Biosystems)).

```
                                                      SEQ ID:1
5'-GATCCGACTTCCCAAGAACAGACGACTTCCCAAGAACAGA-3'

SEQ ID:2
5'-GATCTCTGTTCTTGGGAAGTCGTCTGTTCTTGGGAAGTCG-3'
```

(2) Transfection into U2-OS Cells and Inhibition Test for STAT6 Activation

U2-OS cells were seeded to at $2 \times 10^4$ cells/well in 96-well culture plates, and transfection was carried out using FuGENE 6 Transfection Reagent (Roche Diagnostics GmbH). The procedures of the transfection are shown below.

11 µg of reporter plasmid ((GLS)x8/pTA-Luc) and 1.1 µg of pCMV β (CLONTECH Laboratories, Inc.) were mixed in 1.1 mL of OPTI-MEM I medium (GIBCO BRL) (solution (A)).

33 µL of FuGENE 6 Transfection Reagent was mixed in 1.1 mL of OPTI-MEM I medium (solution (B)).

The above solution (A) and solution (B) were mixed, let them stand for 15 minutes at room temperature, then, 8.8 mL of OPTI-MEM I medium was added and diluted.

To this transfection solution, U2-OS cell suspension (11 mL) in McCoy's 5A medium (GIBCO BRL) containing 10% Fetal Bovine Serum (FBS; GIBCO BRL) at $2 \times 10^5$ cells/mL was added and well mixed.

0.2 mL of the above solution was dispensed into each well of 96-well culture plates, and incubated for 24 hours (37° C., 5% $CO_2$).

After removal of 50 µL of medium from each well, 50 µL of McCoy's 5A medium (serum-free) containing compound of the present application was added to a final concentration of 0.01~2 µM (0.001, 0.01, 0.1, 0.5, 1 or 2 µM), and the plates were incubated for 2 hours (37° C., 5% $CO_2$).

10 µL of the McCoy's 5A medium (serum-free) containing human IL-4 (R&D Systems, Inc) was added to each well to achieve a final concentration of 40 ng/mL, and incubated for 8 hours (37° C., 5% $CO_2$).

Medium was completely removed and plates were preserved at −80° C. until measurements.

(3) Luciferase Assay

Cell lysates were prepared by adding 40 µL of Passive Lysis Buffer (Promega Corporation) to each well.

10 µL of each lysate was transferred to 96-well white plates. 50 µL of PicaGene L.T.2.0 (TOYO INK MFG. CO., LTD.) was added to each well, then, luminescence was measured after leaving for 10 minutes at room temperature.

10 µL of each lysate was transferred to 96-well black plates. 100 µL of Z Buffer (preparation method will be explained later) was added to each well, and fluorescence was measured immediately.

10 µL of each lysate was transferred to 96-well clear plates. 200 µL of protein assay reagent prepared from the BCA Protein Assay Kit (Pierce Biotechnology, Inc.) was added to each well, and, absorbance was measured after incubation for 30 minutes at 37° C.

For measurements of luminescence, fluorescence, and absorbance, microplate reader GENios (TECAN G.M.B.H.) was used.

[Z Buffer Preparation]

Z Buffer $Na_2HPO_4$ (8.8 g), $NaH_2PO_4.2H_2O$ (5.9 g), KCl (0.75 g) and $MgSO_4.7H_2O$ (246 mg) were dissolved in $H_2O$ and made up to 1 L. Just before use, after 32.4 µL of 2-mercaptoethanol per 11.8 mL of the solution was added, further 0.2 mL of MUG working solution (its preparation is described below) was added to provide for experiments.

MUG Working Solution (Freshly Prepared Before Use)

4-Methylumbelliferyl-β-D-galactopyranoside (MUG, 1 mg; SIGMA-ALDRICH Corporation) was dissolved in DMSO (200 µL).

(4) Calculation of Inhibition Rate

Luminescence values that show the degree of activation by IL-4 stimulation were normalized by β-gal values that show transfection efficiency. Using the normalized values, the following calculations were carried out using the luminescence values increased by IL-4 stimulation.

Inhibition Rate(%)=$E/C \times 100$

E: In the presence of the compound of the present application, increased luminescence value by IL-4 stimulation C: Without the presence of the compound of the present application, increased luminescence value by IL-4 stimulation The values of protein assay by BCA reagent were used for a simple assessment of cytotoxicity, and not used for the calculation of inhibition rates.

STAT6 Inhibition Rates are shown below. The values in parentheses in the table represent the concentration of the compound of the present application.

TABLE 20

| Compound Number | Inhibition Rate of STAT6 (%) |
|---|---|
| 2 | 90 (2 µM) |
| 3 | 67 (2 µM) |
| 4 | 71 (2 µM) |
| 5 | 88 (2 µM) |
| 7 | 84 (2 µM) |
| 8 | 93 (2 µM) |
| 9 | 53 (2 µM) |
| 10 | 76 (2 µM) |
| 11 | 40 (2 µM) |
| 12 | 94 (2 µM) |
| 14 | 56 (2 µM) |
| 15 | 59 (2 µM) |

TABLE 20-continued

| Compound Number | Inhibition Rate of STAT6 (%) |
|---|---|
| 16 | 92 (2 μM) |
| 17 | 96 (2 μM) |
| 18 | 79 (2 μM) |
| 22 | 85 (2 μM) |
| 23 | 24 (2 μM) |
| 24 | 93 (2 μM) |
| 25 | 80 (2 μM) |
| 26 | 95 (2 μM) |
| 27 | 98 (2 μM) |
| 30 | 19 (2 μM) |
| 31 | 93 (2 μM) |
| 32 | 92 (2 μM) |
| 34 | 94 (2 μM) |
| 35 | 26 (2 μM) |
| 38 | 77 (2 μM) |
| 39 | 46 (2 μM) |
| 41 | 78 (2 μM) |
| 42 | 41 (2 μM) |
| 43 | 46 (2 μM) |
| 44 | 94 (2 μM) |
| 45 | 76 (2 μM) |
| 46 | 24 (2 μM) |
| 47 | 96 (2 μM) |
| 48 | 42 (2 μM) |
| 49 | 84 (2 μM) |
| 50 | 43 (2 μM) |
| 51 | 83 (2 μM) |
| 52 | 55 (2 μM) |
| 53 | 57 (2 μM) |
| 54 | 89 (2 μM) |
| 55 | 35 (2 μM) |
| 56 | 19 (2 μM) |
| 57 | 75 (2 μM) |
| 58 | 70 (2 μM) |
| 59 | 60 (2 μM) |
| 60 | 26 (2 μM) |
| 61 | 86 (2 μM) |
| 62 | 96 (2 μM) |
| 63 | 94 (2 μM) |
| 64 | 44 (2 μM) |
| 65 | 42 (2 μM) |
| 66 | 85 (2 μM) |
| 67 | 94 (2 μM) |
| 68 | 74 (2 μM) |
| 69 | 79 (2 μM) |
| 70 | 19 (2 μM) |
| 71 | 92 (2 μM) |
| 72 | 37 (2 μM) |
| 73 | 20 (2 μM) |
| 74 | 80 (2 μM) |
| 75 | 76 (2 μM) |
| 76 | 95 (2 μM) |
| 77 | 90 (2 μM) |
| 78 | 46 (2 μM) |
| 79 | 59 (2 μM) |
| 80 | 91 (2 μM) |
| 81 | 92 (2 μM) |
| 82 | 38 (2 μM) |
| 83 | 80 (2 μM) |
| 84 | 83 (2 μM) |
| 85 | 72 (2 μM) |
| 86 | 93 (2 μM) |
| 87 | 91 (2 μM) |
| 88 | 90 (2 μM) |
| 89 | 62 (2 μM) |
| 90 | 11 (2 μM) |

STAT6 inhibition rates where the concentrations of the compound of the present application were 1, 0.1, 0.01 and 0.001 μM were calculated, and the 50% inhibitory concentrations ($IC_{50}$) of the compounds of the present application against activation of STAT6 were evaluated. The results are shown in the following table.

TABLE 21

| Compound Number | $IC_{50}$ (nM) |
|---|---|
| 2 | 58.1 |
| 12 | 15.0 |
| 16 | 82.2 |
| 17 | 82.9 |
| 18 | 91.9 |
| 22 | 82.3 |
| 24 | 36.8 |
| 27 | 3.22 |
| 31 | 6.37 |
| 32 | 5.88 |
| 34 | 3.22 |
| 44 | 7.51 |
| 47 | 7.98 |
| 49 | 14.8 |
| 51 | 9.00 |
| 54 | 15.0 |
| 63 | 5.62 |
| 66 | 3.79 |
| 67 | 5.32 |
| 68 | 40.4 |
| 69 | 10.6 |
| 71 | 3.36 |
| 74 | 105 |
| 75 | 76.0 |
| 76 | 32.9 |
| 77 | 7.29 |
| 80 | 2.23 |
| 81 | 10.9 |
| 86 | 10.8 |
| 87 | 18.3 |
| 88 | 25.5 |

Test Example 2

NF-κB Inhibition Test (1) Transfection to U2-OS Cells and Inhibition Test of Activation U2-OS cells were seeded at $2 \times 10^4$ cells/well in 96-well culture plate, and transfection was carried out using FuGENE 6 Transfection Reagent (Roche Diagnostics GmbH). The procedures of the transfection are shown below.

11 μg of reporter plasmid (pNFκB-Luc; Stratagene Corporation) and 1.1 μg of pCMV β (CLONTECH Laboratories, Inc.) were mixed in 1.1 mL of OPTI-MEM I medium (GIBCO BRL) (solution (A)).

33 μg L of FuGENE 6 Transfection Reagent was mixed in 1.1 mL of OPTI-MEM I medium (solution (B)).

The above solution (A) and solution (B) were mixed, let them stand for 15 minutes at room temperature, then, 8.8 mL of OPTI-MEM I medium was added and diluted.

To this transfection solution, U2-OS cell suspension (11 mL) in McCoy's 5A medium (GIBCO BRL) containing 10% Fetal Bovine Serum (FBS; GIBCO BRL) at $2 \times 10^5$ mL was added and well mixed.

0.2 mL of the above solution was dispensed into each well of 96-well culture plates, and incubated for 24 hours (37° C., 5% $CO_2$).

After removal of 50 μL of medium from each well, 50 μL of McCoy's 5A medium (serum-free) containing compound of the present application was added to a final concentration of 0.01~2 μM (0.001, 0.01, 0.1, 0.5, 1 or 2 μM), and the plates were incubated for 2 hours (37° C., 5% $CO_2$).

10 μL of the McCoy's 5A medium (serum-free) containing human TNF α (PEPROTECH EC Ltd.) was added to each well to achieve a final concentration of 10 ng/mL, and incubated for 8 hours (37° C., 5% $CO_2$).

Medium was completely removed and plates were preserved at −80° C. until measurements.

(2) Luciferase Assay

Cell lysates were prepared by adding 40 μL of Passive Lysis Buffer (Promega Corporation) to each well.

10 μL of each lysate was transferred to 96-well white plates. 50 μL of PicaGene L.T.2.0 (TOYO INK MFG. CO., LTD.) was added to each well, then, luminescence was measured after leaving for 10 minutes at room temperature.

10 μL of each lysate was transferred to 96-well black plates. 100 μL of Z Buffer (preparation method will be explained later) was added to each well, and fluorescence was measured immediately.

10 μL of each lysate was transferred to 96-well clear plates. 200 μL of protein assay reagent prepared from the BCA Protein Assay Kit (Pierce Biotechnology, Inc.) was added to each well, and, absorbance was measured after incubation for 30 minutes at 37° C.

For measurements of luminescence, fluorescence, and absorbance, microplate reader GENios (TECAN G.M.B.H.) was used.

[Z Buffer Preparation]

Z Buffer $Na_2HPO_4$ (8.8 g), $NaH_2PO_4.2H_2O$ (5.9 g), KCl (0.75 g) and $MgSO_4$-$7H_2O$ (246 mg) were dissolved in $H_2O$ and made up to 1 L. Just before use, after 32.4 μL of 2-mercaptoethanol per 11.8 mL of the solution was added, further 0.2 mL of MUG working solution (its preparation is described below) was added to provide for experiments.

4-Methylumbelliferyl-β-D-galactopyranoside (MUG, 1 mg; SIGMA-ALDRICH Corporation) was dissolved in DMSO (200 μL).

(3) Calculation of Inhibition Rate

Luminescence values that show the degree of activation by TNF α stimulation were normalized by β-gal values that show transfection efficiency. Using the normalized values, the following calculation was carried out using the luminescence values that increased by TNF α stimulation.

Inhibition Rate(%)=$E/C$×100

E: In the presence of the compound of the present application, increased luminescence values by TNF α stimulation C: Without the presence of the compound of the present application, increased luminescence values by TNF α, stimulation The values of protein assay by BCA reagent were used for a simple assessment of cytotoxicity, and not used for the calculation of inhibition rates.

NF-κB Inhibition Rates are shown below. The values in parentheses in the table represent the concentration of the compound of the present application.

TABLE 22

| Compound Number | Inhibition Rate of NF·κB (%) |
|---|---|
| 2 | 77 (2 μM) |
| 3 | 30 (2 μM) |
| 4 | 28 (2 μM) |
| 5 | 63 (2 μM) |

TABLE 22-continued

| Compound Number | Inhibition Rate of NF·κB (%) |
|---|---|
| 7 | 46 (2 μM) |
| 8 | 61 (2 μM) |
| 10 | 45 (2 μM) |
| 11 | 22 (2 μM) |
| 12 | 91 (2 μM) |
| 14 | 60 (2 μM) |
| 15 | 53 (2 μM) |
| 16 | 86 (2 μM) |
| 17 | 90 (2 μM) |
| 18 | 67 (2 μM) |
| 22 | 82 (2 μM) |
| 23 | 11 (2 μM) |
| 24 | 91 (2 μM) |
| 25 | 60 (2 μM) |
| 26 | 68 (2 μM) |
| 27 | 95 (2 μM) |
| 31 | 92 (2 μM) |
| 32 | 91 (2 μM) |
| 34 | 95 (2 μM) |
| 35 | 24 (2 μM) |
| 38 | 64 (2 μM) |
| 39 | 16 (2 μM) |
| 41 | 74 (2 μM) |
| 42 | 24 (2 μM) |
| 43 | 32 (2 μM) |
| 44 | 94 (2 μM) |
| 45 | 68 (2 μM) |
| 46 | 16 (2 μM) |
| 47 | 95 (2 μM) |
| 48 | 40 (2 μM) |
| 49 | 87 (2 μM) |
| 50 | 45 (2 μM) |
| 51 | 86 (2 μM) |
| 52 | 27 (2 μM) |
| 53 | 45 (2 μM) |
| 54 | 84 (2 μM) |
| 55 | 16 (2 μM) |
| 57 | 62 (2 μM) |
| 58 | 59 (2 μM) |
| 59 | 43 (2 μM) |
| 60 | 16 (2 μM) |
| 61 | 80 (2 μM) |
| 62 | 89 (2 μM) |
| 63 | 94 (2 μM) |
| 64 | 50 (2 μM) |
| 65 | 20 (2 μM) |
| 66 | 92 (2 μM) |
| 67 | 93 (2 μM) |
| 68 | 71 (2 μM) |
| 69 | 76 (2 μM) |
| 70 | 26 (2 μM) |
| 71 | 94 (2 μM) |
| 72 | 41 (2 μM) |
| 74 | 84 (2 μM) |
| 75 | 78 (2 μM) |
| 76 | 94 (2 μM) |
| 77 | 89 (2 μM) |
| 78 | 49 (2 μM) |
| 79 | 59 (2 μM) |
| 80 | 89 (2 μM) |
| 81 | 90 (2 μM) |
| 83 | 59 (2 μM) |
| 84 | 61 (2 μM) |
| 85 | 79 (2 μM) |
| 86 | 93 (2 μM) |
| 87 | 93 (2 μM) |
| 88 | 90 (2 μM) |
| 89 | 62 (2 μM) |
| 90 | 18 (2 μM) |

NF-κB inhibition rates where the concentrations of the compound of the present application were 1, 0.1, 0.01 and 0.001 μM were calculated, and the 50% inhibitory concentrations ($IC_{50}$) of the compounds of the present application against activation of NF-κB were evaluated. The results are shown in the following table.

TABLE 23

| Compound Number | $IC_{50}$ (nM) |
| --- | --- |
| 2 | 39.4 |
| 12 | 25.2 |
| 16 | 89.1 |
| 17 | 113 |
| 18 | 147 |
| 22 | 80.8 |
| 24 | 43.3 |
| 27 | 6.79 |
| 31 | 12.2 |
| 32 | 13.7 |
| 34 | 7.04 |
| 44 | 15.7 |
| 47 | 14.0 |
| 49 | 28.4 |
| 51 | 17.9 |
| 54 | 43.5 |
| 63 | 16.7 |
| 66 | 9.74 |
| 67 | 16.0 |
| 68 | 63.6 |
| 69 | 30.3 |
| 71 | 8.41 |
| 74 | 66.5 |
| 75 | 35.8 |
| 76 | 20.0 |
| 77 | 8.44 |

TABLE 23-continued

| Compound Number | $IC_{50}$ (nM) |
| --- | --- |
| 80 | 8.11 |
| 81 | 17.8 |
| 86 | 7.62 |
| 87 | 11.7 |
| 88 | 21.9 |

N-[3,5-Bis(trifluoromethyl)phenyl]-5-chloro-2-hydroxybenzamide is a typical compound among the compounds disclosed in the Patent Documents 17 and 18. The 50% inhibitory concentration of the compound was found to be 385 nM. From these results, it is clearly understood that the compounds of the present invention have a superior pharmacological activity as compared with the aforementioned compound.

INDUSTRIAL APPLICABILITY

The compounds of the present invention have an inhibitory activity against activation of STAT6. Furthermore, a number of compounds of the present invention have also an inhibitory activity against activation of NF-κB. Therefore, the compounds of the present invention are useful as STAT6 and/or NF-κB activation inhibitors and useful for prophylactic and/or therapeutic treatment of diseases caused by an activation of STAT6 and/or NF-κB.

What is claimed is:

1. A compound represented by the following formula (I) or a salt thereof:

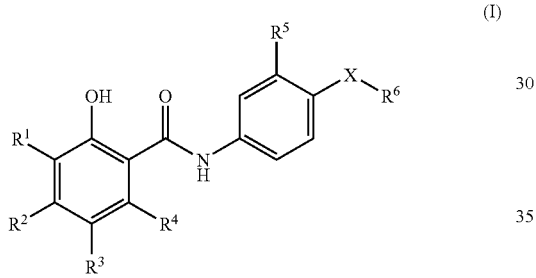

wherein one of $R^1$, $R^2$, $R^3$, and $R^4$ represents a hydrogen atom, a halogen atom, a cyano group, a nitro group, a $C_{1-4}$ alkyl group, a halogenated $C_{1-4}$ alkyl group, or a $C_{1-4}$ alkoxy group, and all of the others represent hydrogen atoms;

$R^5$ represents a halogen atom, a cyano group, a $C_{1-4}$ alkyl group, a halogenated $C_{1-4}$ alkyl group, or a $C_{1-4}$ alkoxy group;

$R^6$ represents a piperazinyl group which may be substituted with one or more groups selected from
    a hydroxy group,
    a $C_{1-6}$ alkyl group,
    a substituted $C_{1-6}$ alkyl group,
    a $C_{2-7}$ alkanoyl group,
    a substituted $C_{2-7}$ alkanoyl group,
    a carboxy group,
    a carbamoyl group,
    a $C_{2-5}$ alkoxycarbonyl group,
    an amino group,
    a $C_{1-6}$ alkylamino group,
    a di-$C_{1-6}$ alkylamino group,
    an oxo group, and
    a 3 to 7-membered completely saturated heterocyclic group;

X represents a single bond, an oxygen atom, a sulfur atom, $NR^7$, —O—$CH_2$—, or —N($R^8$)—$CH_2$—, wherein $R^7$ represents a hydrogen atom or a $C_{1-4}$ alkyl group; or $R^7$ is combined with a substituent of $R^6$ to represent a single bond, a methylene group, or an ethylene group, and wherein $R^8$ represents a hydrogen atom, a $C_{1-4}$ alkyl group, or a $C_{7-12}$ aralkyl group.

2. The compound according to claim 1 or a salt thereof, wherein X is a single bond.

3. The compound according to claim 1 or a salt thereof, wherein $R^1$, $R^2$, and $R^4$ are independently a hydrogen atom;

$R^6$ is a piperazinyl group which may be substituted with one or more groups selected from
    a hydroxy group,
    a $C_{1-6}$ alkyl group,
    a $C_{7-12}$ aralkyl group,
    a $C_{2-7}$ alkanoyl group,
    a carbamoyl group,
    an amino group,
    a $C_{1-6}$ alkylamino group,
    a di-$C_{1-6}$ alkylamino group,
    an oxo group,
    a pyrrolidinyl group,
    an amino substituted $C_{1-6}$ alkyl group, and
    a piperidinyl substituted $C_{2-7}$ alkanoyl group;

X is a single bond, an oxygen atom, $NR^7$, or —O—$CH_2$—; and $R^7$ is a hydrogen atom.

4. A medicament which comprises as an active ingredient a compound according to claim 1 or a pharmacologically acceptable salt thereof.

5. The compound according to claim 3 or a salt thereof, wherein $R^6$ is any one of the following groups:

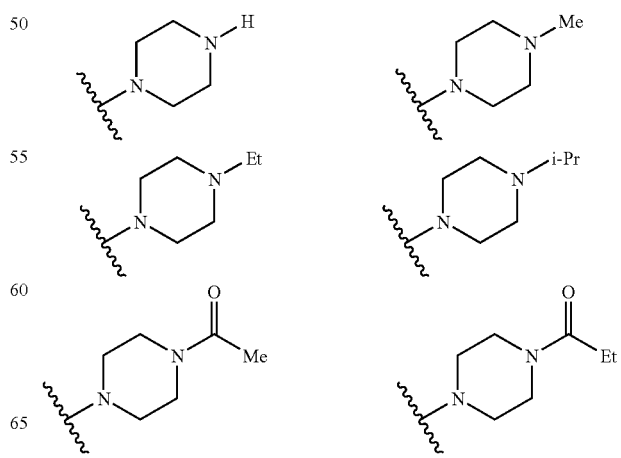

151
-continued
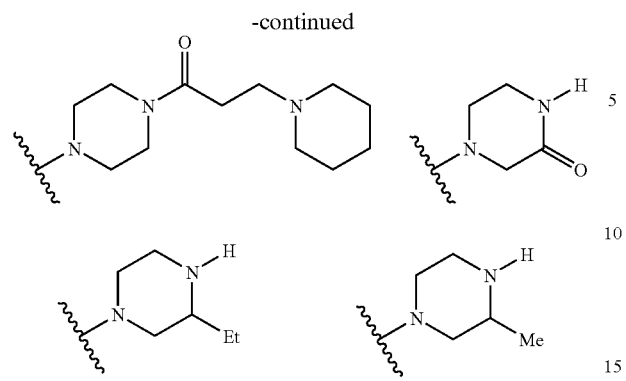
152
-continued
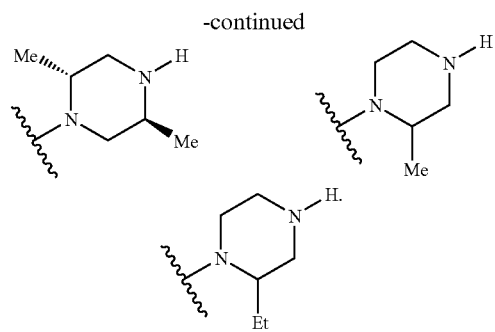
* * * * *

SEQUENCE LISTING

```
<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatccgactt cccaagaaca gacgacttcc caagaacaga                          40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatctctgtt cttgggaagt cgtctgttct tgggaagtcg                          40

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
-continued
<220> FEATURE:
<221> NAME/KEY: MOD_RES
<222> LOCATION: (4)
<223> OTHER INFORMATION: Variable amino acid

<400> SEQUENCE: 3

Gly Tyr Lys Xaa Phe
1               5

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttcccaagaa                                                            10
```